US012454563B2

(12) United States Patent
Winter et al.

(10) Patent No.: US 12,454,563 B2
(45) Date of Patent: Oct. 28, 2025

(54) IMMUNE CELL FUNCTION

(71) Applicant: Kite Pharma, Inc., Santa Monica, CA (US)

(72) Inventors: Ruth E. Winter, Oakland, CA (US); Saikat Banerjee, Oakland, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 241 days.

(21) Appl. No.: 17/690,968

(22) Filed: Mar. 9, 2022

(65) Prior Publication Data

US 2022/0289815 A1 Sep. 15, 2022

Related U.S. Application Data

(60) Provisional application No. 63/210,300, filed on Jun. 14, 2021, provisional application No. 63/159,610, filed on Mar. 11, 2021.

(51) Int. Cl.

| | |
|---|---|
| ***C07K 14/705*** | (2006.01) |
| ***A61K 40/11*** | (2025.01) |
| ***A61K 40/31*** | (2025.01) |
| ***A61K 40/42*** | (2025.01) |
| ***C07K 14/725*** | (2006.01) |
| ***C07K 16/30*** | (2006.01) |
| ***C12N 5/0783*** | (2010.01) |

(52) U.S. Cl.

CPC .......... *C07K 14/7051* (2013.01); *A61K 40/11* (2025.01); *A61K 40/31* (2025.01); *A61K 40/4211* (2025.01); *A61K 40/4261* (2025.01); *C07K 14/70521* (2013.01); *C07K 16/30* (2013.01); *C12N 5/0636* (2013.01); *A61K 2239/31* (2023.05); *A61K 2239/38* (2023.05); *A61K 2239/48* (2023.05); *C07K 2317/622* (2013.01); *C07K 2319/03* (2013.01); *C07K 2319/33* (2013.01); *C12N 2510/00* (2013.01)

(58) Field of Classification Search

CPC .......... C07K 14/7051; C07K 14/70521; C07K 16/30; C07K 2317/622; C07K 2319/03; C07K 2319/33; C07K 14/5443; C07K 14/7155; A61K 35/17; A61K 39/4631; A61K 2239/48; A61K 39/4611; C12N 5/0636; C12N 2510/00; C12N 5/0646; A61P 35/00

See application file for complete search history.

(56) References Cited

U.S. PATENT DOCUMENTS

| | | | | |
|---|---|---|---|---|
| 11,708,401 | B2 * | 7/2023 | Emtage .............. | A61K 39/4611 424/93.2 |
| 2016/0158285 | A1 | 6/2016 | Cooper et al. | |
| 2020/0002402 | A1 | 1/2020 | Emtage et al. | |
| 2020/0147137 | A1 | 5/2020 | McKearn et al. | |
| 2020/0172879 | A1 * | 6/2020 | Suri .................. | A61K 39/4644 |
| 2021/0024959 | A1 | 1/2021 | Valamehr et al. | |

FOREIGN PATENT DOCUMENTS

| | | | | |
|---|---|---|---|---|
| WO | WO-2018038945 | A1 * | 3/2018 | ............. A61K 35/12 |
| WO | WO-2019002633 | A1 * | 1/2019 | ............. A61K 35/17 |
| WO | WO-2022/006451 | A2 | 1/2022 | |

OTHER PUBLICATIONS

Itoh, N et. al. "The Polypeptide Encoded by the cDNA for Human Cell Surface Antigen Fas Can Mediate Apoptosis", 1991, Cell, 66, 233-243. (Year: 1991).*
Berraondo, P. et al. (2019) "Cytokines in clinical cancer immunotherapy" British Journal of Cancer 120:6-15.
Fu, Q. et al. (2016) "Structural Basis and Functional Role of Intramembrane Trimerization of the Fas/CD95 Death Receptor" Molecular Cell 61:602-613.
Guo, Y. et al. (2017) "Immunobiology of the IL-15/IL-15R[alpha] complex as an antitumor and antiviral agent" Cytokine and Growth Factor Reviews 38:10-21.
Intl. Search Report-Written Opinion dated Jul. 15, 2022 for Intl. Appl. No. PCT/US2022/019607.
Office Action dated May 22, 2023 for Taiwanese Appl. No. 111108782.
Office Action dated May 24, 2024 for Australian Appl. No. 2022234333.
Office Action dated Nov. 19, 2024 for Japanese Appl. No. 2023-554784.
Office Action dated Dec. 4, 2024 for Australian Appl. No. 2022234333.

* cited by examiner

*Primary Examiner* — Nelson B Moseley, II
*Assistant Examiner* — Alyssa Rae Stonebraker

(57) ABSTRACT

The present disclosure relates to the field of cell therapy, and more specifically, to improving CAR and/or TCR function through improvement of cytokine signaling. Disclosed are embodiments of a membrane bound interleukin 15 (IL-15)-IL-15Ralpha sushi domain chimeric receptor. The chimeric receptor may comprise a FAS transmembrane domain or an IL-7 transmembrane domain. Different embodiments of the chimeric receptor have different polypeptide lengths between the IL-15 region and the transmembrane domain.

12 Claims, No Drawings

Specification includes a Sequence Listing.

IMMUNE CELL FUNCTION

CROSS REFERENCE TO RELATED APPLICATIONS

This application claims priority to U.S. Provisional Application No. 63/159,610, filed Mar. 11, 2021, and U.S. Provisional Application No. 63/210,300, filed Jun. 14, 2021 which are incorporated herein in their entireties for all purposes.

SEQUENCE LISTING

The instant application contains a Sequence Listing which has been submitted electronically in ASCII format and is hereby incorporated by reference in its entirety. Said ASCII copy, created on Apr. 14, 2022, is named K-1103-US-NP_SL.txt and is 93,064 bytes in size.

TECHNICAL FIELD

The present disclosure relates to the fields of immunology and cell therapy, and more specifically, to improving T cell and Natural Killer (NK) cell based immunotherapies comprising a chimeric antigen receptor (CAR) and/or T cell receptor (TCR) by modulating cytokine signaling.

BACKGROUND

The immune system provides an innate defense against cancer through its ability to search, seek and destroy malignant cells throughout the body. However, a caveat to this defense mechanism is that certain cancers may induce an immunosuppressive microenvironment that reduces the robustness of an antitumor immune response. (Beatty et al., Clin Cancer Res, (21)(4): 687-632 (2015)). These immune escape mechanisms present challenges for the implementation and effectiveness of cellular immunotherapies, including the use of engineered cell therapy technologies such as chimeric antigen receptor (CAR) T cell therapy and T cell receptor (TCR) T cell therapy and/or Natural Killer cell based immunotherapy.

Since overall T cell function and proliferation are dependent on cytokine signaling, it is theorized that the use of cytokines may improve the overall quality and potency of T cell based therapies. Past studies have demonstrated the successful use of IL-2 as a means of T-cell based therapy expansion, although drawbacks included both T-cell exhaustion and diminished T-cell persistence. (Gattinoni et al., J Clin Invest, (115): 1616-1626 (2005)). Other studies show an improved potency of CAR-T cells with the use of IL-7 and IL-15 together (Xu et al., Blood, (123): 3750-3759 (2014). CAR-T potency was also reported to improve with the use of IL-21 (Singh et al., Cancer Res, (71) 3516-3527 (2011)). Similarly, IL-2 has been found to enhance the cytotoxicity of NK cells (Hu et al., Front. Immunol., (20) 1205 (2019)).

Accordingly, there is a need to exploit the use of cytokine signaling as a means for improving the efficacy of immune cell based immunotherapies.

SUMMARY

Disclosed is a membrane bound interleukin 15 (IL-15)-IL-15Rα sushi domain chimeric receptor. In embodiments, the membrane bound IL-15-IL-15Rα sushi domain chimeric receptor comprises an IL-15 polypeptide comprising the amino acid sequence according to SEQ ID NO: 6, a first linker linking the IL-15 domain to a IL-15Rα sushi domain polypeptide according to SEQ ID NO: 7 or SEQ ID NO: 95, and a transmembrane domain comprising a FAS transmembrane domain or a dimerization domain, such as an IL-7 transmembrane domain.

In embodiments, the first linker linking the IL-15 polypeptide and the IL-15Rα sushi domain comprises the amino acid sequence according to SEQ ID NO: 8. In embodiments, the first linker comprises the amino acid sequence according to SEQ ID NO: 10.

In embodiments, the IL-15Rα sushi domain polypeptide is linked to the transmembrane domain by a second linker. In embodiments, the second linker comprises the amino acid sequence according to SEQ ID NO: 24. In embodiments, the second linker comprises the amino acid sequence according to SEQ ID NO: 26.

In embodiments, the transmembrane domain is a FAS transmembrane domain comprising the amino acid sequence according to SEQ ID NO: 22. In embodiments, the transmembrane domain is a FAS transmembrane domain comprising the amino acid sequence according to SEQ ID NO: 42. In embodiments, the IL-7 transmembrane domain comprises the amino acid sequence according to SEQ ID NO: 23.

In embodiments, the membrane bound IL-15-IL-15Rα sushi domain chimeric receptor comprises an amino acid sequence selected from the group consisting of SEQ ID NO: 27, SEQ ID NO: 28 and 94. In embodiments, the membrane bound IL-15-IL-15Rα sushi domain chimeric receptor comprises the amino acid according to SEQ ID NO: 30.

In embodiments, the membrane bound IL-15-IL-15Rα sushi domain chimeric receptor comprises further comprises a signaling sequence. In embodiments, the signaling sequence comprises an amino acid sequence according to one of SEQ ID NOS: 12-20. In embodiments, the signaling sequence comprises an amino acid sequence according to SEQ ID NO: 12.

Disclosed is a nucleic acid encoding a membrane bound IL-15-IL-15Rα sushi domain chimeric receptor described herein. In embodiments, a nucleic acid encoding a membrane bound IL-15-IL-15Rα sushi domain chimeric receptor comprises the nucleic acid sequence according to a sequence selected from the group consisting of SEQ ID NO: 31, SEQ ID NO: 32, SEQ ID NO: 96, SEQ ID NO: 97, and SEQ ID NO: 100.

Disclosed is a recombinant vector comprising a nucleic acid encoding a membrane bound IL-15-IL-15Rα sushi domain chimeric receptor described herein.

In embodiments, the recombinant vector or nucleic acid further comprises a nucleic acid encoding a chimeric antigen receptor (CAR) or a T cell receptor (TCR). In embodiments, the CAR or TCR binds a tumor antigen. In embodiments, the tumor antigen is selected from the group consisting of 2B4 (CD244), 4-1BB, 5T4, A33 antigen, adenocarcinoma antigen, adrenoceptor beta 3 (ADRB3), A kinase anchor protein 4 (AKAP-4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl)), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-0-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PD-L1, B7H1), CD279 (PD-1), CD352, CD358, CD300 molecule-like family member f (CD300LF), Carcinoembryonic antigen (CEA), claudin 6 (CLDN6), C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1, CRACC, CD319, and 19A24), CTLA-4, Cyclin B 1, chromosome X open reading frame 61 (CXORF61), Cytochrome P450 1B 1 (CYP1B1), DNAM-1 (CD226), desmoglein 4, DR3, DR5, E-cadherin neoepitope, epidermal growth factor receptor (EGFR), EGF1R, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FcRL5), fetal acetylcholine receptor (AChR), fibronectin extra domain-B, Fms-Like Tyrosine Kinase 3 (FLT3), folate-binding protein (FBP), folate receptor 1, folate receptor β, Folate receptor γ, Fos-related antigen 1, Fucosyl, Fucosyl GM1; GM2, ganglioside G2 (GD2), ganglioside GD3 (aNeu5Ac(2-8)aNeu5Ac(2-3)bDGalp(l-4) bDGlcp(l-l)Cer), o-acetyl-GD2 ganglioside (OAcGD2), GITR (TNFRSF 18), GM1, ganglioside GM3, hexasaccharide portion of globoH glycoceramide (GloboH), glycoprotein 75, Glypican-3 (GPC3), glycoprotein 100 (gpl00), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papilloma virus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-llRα), IL-13, Interleukin-13 receptor subunit alpha-2 (IL-13Rα2 or CD213A2), insulin-like growth factor I receptor (IGF1-R), integrin α5β1, integrin αvβ3, intestinal carboxyl esterase, κ-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2 (LILRA2), legumain, Leukocyte-associated immunoglobulin-like receptor 1 (LAIR1), Lewis(Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MARTl, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUC5AC, MUC5b, MUC7, MUC16, mucin CanAg, Mullerian inhibitory substance (MIS) receptor type IL, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma X breakpoint 2 (SSX2), Survivin, Tumor-associated glycoprotein 72 (TAG72), TCR5β, TCRα, TCRβ, TCRδ, TCRγ. Alternate Reading Frame Protein (TARP), telomerase, TIGIT, TNF-α precursor, tumor endothelial marker 1 (TEM1/CD248), tumor endothelial marker 7-related (TEM7R), tenascin C, TGF-β1, TGF-β2, transglutaminase 5 (TGS5), angiopoietin-binding cell surface receptor 2 (Tie 2), TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, uroplakin 2 (UPK2), VEGF-A, VEGFR-1, vascular endothelial growth factor receptor 2 (VEGFR2), and vimentin, TACI, Wilms tumor protein (WT1), or X Antigen Family Member 1A (XAGE1).

Disclosed is an immune cell comprising a membrane bound IL-15-IL-15Rα sushi domain chimeric receptor, recombinant vector or nucleic acid described herein. In embodiments, the immune cell is a T cell or a Natural Killer (NK) cell. Disclosed is a pharmaceutical composition comprising an immune cell described herein.

Disclosed is a method of treating a cancer associated with expression of a tumor antigen in a subject comprising: administering to the subject an effective amount of immune cell or pharmaceutical composition disclosed herein.

Disclosed is a method of inducing an immune response in a subject or immunizing a subject against a cancer, the method comprising administering to the subject an effective amount of an immune cell or the pharmaceutical composition described herein.

Disclosed is a method for improving immune cell function, comprising engineering the immune cell to express the membrane bound interleukin 15 (IL-15)-IL-15Rα sushi domain chimeric receptor.

DETAILED DESCRIPTION

Terms

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "e.g.," as used herein, is used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", $2^{nd}$ ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"Administering" refers to the physical introduction of an agent to a subject, such as a modified T cell or NK cell disclosed herein, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms, "activated" and "activation" refer to the state of a T cell or NK cell that has been sufficiently stimulated to induce detectable cellular proliferation. In one embodiment, activation may also be associated with induced cytokine production, and detectable effector functions. The term "activated T cells" refers to, among other things, T cells that are proliferating. The term "activated NK cells" refers to, among other things, NK cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

The term "agent" may refer to a molecule or entity of any class comprising, or a plurality of molecules or entities, any of which may be, for example, a polypeptide, nucleic acid, saccharide, lipid, small molecule, metal, cell (such as a T cell or NK cell or progenitor of such cells), or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

The term "allogeneic" refers to any material derived from one individual which is then introduced to another individual of the same species, e.g., allogeneic T cell transplantation.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Transbodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. “Isotype” refers to the Ab class or subclass (e.g., IgM or IgG1) that is encoded by the heavy chain constant region genes. The term “antibody” includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term “antibody” also includes an antigen binding fragment or an antigen-binding portion of any of the aforementioned immunoglobulins, and includes a monovalent and a divalent fragment or portion, and a single chain Ab.

An “antigen binding molecule,” “antigen binding portion,” “antigen binding fragment,” or “antibody fragment” or “antigen binding domain” refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, an antigen binding molecule is a chimeric antigen receptor (CAR) or an engineered T cell receptor (TCR). In certain embodiments, the antigen binding molecule or domain is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule or domain comprises or consists of avimers.

In some instances, a CDR is substantially identical to one found in a reference antibody (e.g., an antibody of the present disclosure) and/or the sequence of a CDR provided in the present disclosure. In some embodiments, a CDR is substantially identical to a reference CDR in that it is either identical in sequence or contains between 1, 2, 3, 4, or 5 (e.g., 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g., 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody. In various embodiments, an antigen binding fragment cross-competes with the reference antibody, for example, binding to substantially the same or identical epitope as the reference antibody An antigen binding fragment may be produced by any means. For example, in some embodiments, an antigen binding fragment may be enzymatically or chemically produced by fragmentation of an intact antibody. In some embodiments, an antigen binding fragment may be recombinantly produced (such as by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term “variable region” or “variable domain” is used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In embodiments, the variable region is a primate (e.g., non-human primate) variable region. In certain embodiments, the variable region comprises rodent or murine CDRs and primate (e.g., non-human primate) framework regions (FRs).

The terms “VL” and “VL domain” are used interchangeably to refer to the light chain variable region of an antibody or an antigen-binding molecule thereof.

The terms “VH” and “VH domain” are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| CDR Numbering | | | | |
|---|---|---|---|---|
| Loop | Rabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha ($\alpha$), delta ($\beta$), epsilon ($\varepsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

An "antigen" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a TCR or CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. A "target" is any molecule bound by a binding motif, CAR, TCR or antigen binding agent, e.g., an antibody.

"Antigen-specific targeting region" (ASTR) refers to the region of the CAR or TCR which targets specific antigens. The targeting regions on the CAR or TCR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of this disclosure. In fact, almost any molecule that binds a given antigen with high affinity can be used as an antigen-specific targeting region, as will be appreciated by those of skill in the art.

"Antigen presenting cell" or "APC" refers to cells that process and present antigens to T cells. Exemplary APCs comprise dendritic cells, macrophages, B cells, certain activated epithelial cells, and other cell types capable of TCR stimulation and appropriate T cell costimulation.

An "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

"Binding affinity" generally refers to the strength of the sum total of non-covalent interactions between a single binding site of a molecule (e.g., an antibody) and its binding partner (e.g., an antigen). Unless indicated otherwise "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

The term "KD" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec−1 or 1/s) refers to the dissociation rate constant of a particular antibody-antigen interaction, or the dissociation rate constant of an antibody or antibody-binding fragment. Said value is also referred to as the $k_{oi}$r value.

The term "$k_a$" (M−1×sec−1 or 1/M) refers to the association rate constant of a particular antibody-antigen interaction, or the association rate constant of an antibody or antibody-binding fragment.

The term "$K_A$" (M−1 or 1/M) refers to the association equilibrium constant of a particular antibody-antigen interaction, or the association equilibrium constant of an antibody or antibody binding fragment. The association equilibrium constant is obtained by dividing the $k_a$ by the $k_d$.

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding motif, antibody, or antigen binding system with a target of the binding motif, antibody, or antigen binding system as compared to association of the binding motif, antibody, or antigen binding system with an entity that is not the target (i.e. non-target). In some embodiments, a binding motif, antibody, or antigen binding system selectively binds a target if binding between the binding motif, antibody, or antigen binding system and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding motif, antibody, or antigen binding system and a non-target. In some embodiments, a binding motif, antibody, or antigen binding system selectively binds a target if the binding affinity is less than about $10^{-5}$ M, less than about $10^{-6}$ M, less than about $10^{-7}$ M, less than about $10^{-8}$ M, or less than about $10^{-9}$ M.

In another embodiment, molecules that specifically bind to an antigen bind with a dissociation constant ($K_d$) of about $1\times10^{-7}$ M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{-5}$.

In certain embodiments, provided herein is an antibody or an antigen binding molecule thereof that binds to the target human antigen, e.g., In certain embodiments, the antigen binding molecule binds to a target antigen with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

The term "cancer" relates generally to a class of diseases or conditions in which abnormal cells divide without control and may invade nearby tissues. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time. Cancer further includes relapsed or refractory large B-cell lymphoma after two or more lines of systemic therapy, including diffuse large B-cell lymphoma (DLBCL) not otherwise specified, primary mediastinal large B-cell lymphoma after two or more lines of systemic therapy, high grade B-cell lymphoma, and DLBCL arising from follicular lymphoma.

The term "cancerous cell," "cancer cell," "tumor cell" or variant thereof refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which may be measured as the number, volume, or weight of the tumor.

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

"Chimeric antigen receptor" or "CAR" refers to a molecule engineered to comprise a binding motif and a means of activating immune cells (for example T cells such as naive T cells, central memory T cells, effector memory T cells, NK cells or combination thereof) upon antigen binding. CARs are also known as artificial T cell receptors, chimeric T cell receptors or chimeric immunoreceptors. In some embodiments, a CAR comprises a binding motif, an extracellular domain, a transmembrane domain, one or more co-stimulatory domains, and an intracellular signaling domain. A T cell that has been genetically engineered to express a chimeric antigen receptor may be referred to as a CAR T cell. Similarly an NK cell that has been genetically engineered to express a chimeric antigen receptor may be referred to as a CAR NK cell.

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include an decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition.

"Extracellular domain" (or "ECD") refers to a portion of a polypeptide that, when the polypeptide is present in a cell membrane, is understood to reside outside of the cell membrane, in the extracellular space.

The term "extracellular ligand-binding domain," as used herein, refers to an oligo- or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6: 412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a costimulatory manner may contain signaling motifs which are known as immunoreceptor tyrosine-based activation motif or ITAMs.

Examples of ITAM containing primary cytoplasmic signaling sequences that are of particular use in the disclosure include those derived from DAP10, DAP12, TCRzeta, FcR-gamma, FcRbeta, CD3gamma, CD3delta, CD3epsilon, CD5, CD22, CD79a, CD79b and CD66d.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1 BB (CD137), 0X40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from 4-1 BB, other costimulatory domains are contemplated. The inclusion of one or more co stimulatory signaling domains may enhance the efficacy and expansion of T cells expressing CAR receptors. The intracellular signaling and costimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain derived from CD3zeta or FcRgamma together with one or more costimulatory signaling domains (e.g., intracellular costimulatory domains derived from 4-1BB, CD28, CD137, CD134 and CD278) may more effectively direct antitumor activity as well as increased cytokine secretion, lytic activity, survival and proliferation in CAR expressing T cells in vitro, and in animal models and cancer patients (Milone et al., Molecular Therapy, 2009: 17: 1453-1464; Zhong et al., Molecular Therapy, 2010; 18: 413-420; Carpenito et al., PNAS, 2009; 106:3360-3365).

A "costimulatory signal" refers to a signal, which in combination with a primary signal, such as TCR/CD3 ligation, leads to a T cell response, such as, but not limited to, proliferation and/or upregulation or down regulation of key molecules.

A "costimulatory ligand" includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-4BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-4BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A “costimulatory molecule” is a cognate binding partner on a T cell that specifically binds with a costimulatory ligand, thereby mediating a costimulatory response by the T cell, such as, but not limited to, proliferation. Costimulatory molecules include, but are not limited to, A “costimulatory molecule” is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CDl-1a, CDl-1b, CDl-lc, CDl-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGBl, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CDl 1a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Lyl08), SLAMF7, SLP-76, TNF, TNFr, TNFR2, Toll ligand receptor, TRANCE/RANKL, VLA1, or VLA-6, or fragments, truncations, or combinations thereof.

A “conservative amino acid substitution” is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be “substantially similar” if they contain a conservative amino acid substitution in corresponding positions. For example, certain amino acids are generally classified as “hydrophobic” or “hydrophilic” amino acids, and/or as having “polar” or “non-polar” side chains. Substitution of one amino acid for another of the same type may be considered a conservative substitution. Exemplary amino acid categorizations are summarized in Tables 2 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 3

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

“Combination therapy” refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all “doses” of a first regimen are administered prior to administration of any doses of a second regimen); in some embodiments, such agents are administered in overlapping dosing regimens. In some embodiments, “administration” of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

“Corresponding to” may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as “corresponding to” a residue in an appropriate reference polymer. For example, for purposes of simplicity, residues in a polypeptide may be designated using a canonical numbering system based on a reference related polypeptide, so that an amino acid “corresponding to” a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

An antigen binding molecule, such as an antibody, an antigen binding fragment thereof, CAR or TCR, "cross-competes" with a reference binding molecule, such as an antibody or an antigen binding fragment thereof, if the interaction between an antigen and the first antigen binding molecule blocks, limits, inhibits, or otherwise reduces the ability of the reference binding molecule to interact with the antigen. Cross competition can be complete, e.g., binding of the antigen binding molecule to the antigen completely blocks the ability of the reference binding molecule to bind the antigen, or it can be partial, e.g., binding of the antigen binding molecule to the antigen reduces the ability of the reference antigen binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137: 3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

A "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include an decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition.

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence motif, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target.

In some embodiments, the CAR is engineered such that the costimulatory domain is expressed as a separate polypeptide chain. Example CAR T cell therapies and constructs are described in U.S. Patent Publication Nos. 2013/0287748, 2014/0227237, 2014/0099309, and 2014/0050708, which are incorporated by reference in their entirety. "Adoptive cell therapy" or "ACT" involves transfer of immune cells with anti-tumor activity into a subject, e.g., a cancer patient. In some embodiments, ACT is a treatment approach that involves the use of lymphocytes (e.g., engineered lymphocytes) with anti-tumor activity.

The terms "enhance" or "promote," or "increase" or "expand" refers generally to the ability of a composition contemplated herein to produce, elicit, or cause a greater physiological response (e.g., downstream effects) compared to the response caused by either vehicle or a control molecule/composition. A measurable physiological response may include an increase in T cell expansion, activation, persistence, and/or an increase in cancer cell death killing ability, among others apparent from the understanding in the art and the description herein. An "increased" or "enhanced" amount is typically a "statistically significant" amount, and may include an increase that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7, 1.8, etc.) the response produced by vehicle or a control composition.

An "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

"Endogenous" with reference to a gene, protein, and/or nucleic acid refers to the natural presence of that gene, protein, and/or nucleic acid in a cell, such as an immune cell.

"Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g. without introduction of the exogenous nucleic acid.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

As used herein, "expansion" refers to expanding a population of transduced immune cells for a particular time to produce a population of engineered immune cells. The predetermined time for expansion can be any suitable time which allows for the production of (i) a sufficient number of cells in the population of engineered immune cells for at least one dose for administering to a patient, (ii) a population of engineered immune cells with a favorable proportion of juvenile cells compared to a typical longer process, or (iii) both (i) and (ii). This time will depend on the cell surface receptor expressed by the immune cells, the vector used, the dose that is needed to have a therapeutic effect, and other variables. Thus, in some embodiments, the predetermined time for expansion can be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or more than 21 days.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of man. In embodiments, a CAR is a fusion protein. In an embodiment, a membrane-bound IL-15-IL-15Rα sushi domain chimeric polypeptide is a fusion protein.

The term "gene product" or "expression product" generally refers to an RNA transcribed from the gene (pre- and/or post-processing) or a polypeptide (pre- and/or post-modification) encoded by an RNA transcribed from the gene.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or NK cell, which can either be obtained from a patient or a donor. The cell can be modified to express an exogenous construct, such as, e.g., a membrane bound interleukin 15 (IL-15)-IL-15Rα sushi domain chimeric receptor, a chimeric antigen receptor (CAR) or a T cell receptor (TCR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, or other mechanism, or previously present genetic material is altered or removed, for example by substitution or deletion mutation, or by other protocols). An engineered cell may be modified to express an exogenous construct, such as, e.g., a membrane bound interleukin 15 (IL-15)-IL-15Rα sushi domain chimeric receptor, a chimeric antigen receptor (CAR) or a T cell receptor (TCR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents.

A "T cell receptor" or "TCR" refers to antigen-recognition molecules present on the surface of T cells. During normal T cell development, each of the four TCR genes, α, β, γ, and δ, may rearrange leading to highly diverse TCR proteins.

The term "heterologous" means from any source other than naturally occurring sequences. For example, a heterologous sequence included as a part of a costimulatory protein is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, such as at least about 95%, 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even at least 98% or 99% sequence identity. Typically, the residue positions which are not identical differ by conservative amino acid substitutions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, NK cells and T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells or NK cells of the immunotherapy can come from any source known in the art. For example, T cells and NK cells can be differentiated in vitro from a hematopoietic stem cell population or can be obtained from a subject. T cells and NK cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. An in vitro cell can include a T cell or an NK cell. The term "in vivo" refers to events that occur within a multi-cellular organism, such as a human or a non-human animal.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Linker" (L) or "linker domain" or "linker region" refers to an oligo- or polypeptide region from about 1 to 100 amino acids in length, for example linking together any of the domains/regions of a membrane-bound IL-15-IL-15Rα sushi domain chimeric polypeptide, a chimeric antigen receptor, and/or scFv, or ever one of more of those polypeptides together. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL (SEQ ID NO: 1) sequences of porcine teschovirus (P2A), virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ motif (SEQ ID NO: 2), which results in cleavage between the 2A glycine and the 2B proline. Other linkers include non-cleavable linkers. A number of linkers are employed to realize the subject disclosure including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167. In some embodiments, the linker is a synthetic linker. In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS (SEQ ID NO: 104)), e.g., 1, 2, 3, 4, 5, 6, 7, 8, 9, or 10 or more GS pairs ("GS" disclosed as SEQ ID NO: 104). In an embodiment, a linker has the amino acid sequence AGS (SEQ ID NO: 3). In an embodiment, a linker has the amino acid sequence GGGSGGGGSGGGGSGGGGSGGGS (SEQ ID NO: 4). In an embodiment, a linker has the amino acid sequence GGGGSGGGGS (SEQ ID NO: 5)

A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. A linker may connect or link together any of the domains/regions of a membrane-bound IL-15-IL-15Rα sushi domain chimeric polypeptide, a chimeric antigen receptor, and/or scFv. In some embodiments, a polypeptide linker is at least 2, 3,4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In one example, a liker is used to connect or link the C-terminal end of an IL-15 polypeptide to the N-terminal end of an IL-15Rα sushi domain polypeptide. In another example a linker is used to link the C-terminal end of an IL-15Rα sushi domain polypeptide to a transmembrane domain. In some embodiments, a linker is characterized in that it tends not to adopt a rigid three-dimensional structure, and instead provides flexibility to the polypeptide. In another example it may be used to connect to or more polypeptides to be expressed, such as a CAR, TCR and/or membrane-bound IL-15-IL-15Rα sushi domain chimeric polypeptide, as disclosed herein. In some examples, the CAR or TCR and membrane-bound IL-15-IL-15Rα sushi domain chimeric polypeptide are connected by a cleavable linker, for example so that they can be expressed as a single peptide and then cleaved in the cell.

The term "lymphocyte" includes natural killer (NK) cells, T cells, or B cells. NK cells are a type of cytotoxic (cell toxic) lymphocyte that represent a component of the inherent immune system. NK cells reject tumors and cells infected by viruses. It works through the process of apoptosis or programmed cell death. They were termed "natural killers" because they do not require activation in order to kill cells. T cells play a role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element.

A "patient" includes any human who is afflicted with a cancer. The terms "subject" and "patient" are used interchangeably herein.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions;

polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "proliferation" refers to an increase in cell division, either symmetric or asymmetric division of cells. In some embodiments, "proliferation" refers to the symmetric or asymmetric division of T cells. "Increased proliferation" occurs when there is an increase in the number of cells in a treated sample compared to cells in a non-treated sample.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+ T lymphocytes that participate in controlling certain immune activities, e.g., autoimmunity, allergy, and response to infection. Regulatory T cells may regulate the activities of T cell populations, and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+ T lymphocytes. However, Treg cells within a tumor microenvironment (i.e. tumor-infiltrating Treg cells), Treg cells may make up as much as 20-30% of the total CD4+ T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

"Single chain variable fragment", "single-chain antibody variable fragments" or "scFv" antibodies refer to forms of antibodies comprising the variable regions of only the heavy and light chains, connected by a linker peptide.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

"Stimulation," refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

A "therapeutically effective amount," "effective dose," "effective amount," or "therapeutically effective dosage" of a therapeutic agent, e.g., engineered CAR T cells or NK cell, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., Molecular Cloning: A Laboratory Manual (2d ed., Cold Spring Harbor Laboratory Press, Cold Spring Harbor, N.Y. (1989)), which is incorporated herein by reference.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity.

A "transmembrane domain" is a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. A transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space. In one example the IL-15 and IL-15Rα portions of a membrane-bound IL-15-IL-15Rα sushi domain chimeric polypeptide are displayed in the extracellular side of the plasma membrane.

By "signal sequence" is meant a peptide sequence generally present at the N-terminus of newly synthesized proteins that directs their entry into the secretory pathway.

By "a membrane-bound IL-15-IL-15Rα sushi domain chimeric polypeptide", it is meant an IL-15 polypeptide is linked to the IL-15Rα sushi domain. The membrane-bound IL-15-IL-15Rα sushi domain chimeric polypeptide is further tethered to the cellular membrane (and not secreted) by linking to a transmembrane domain as described herein.

The term "persistence" refers to the ability of, e.g., one or more transplanted immune cells administered to a subject or their progenies (e.g., NK cells or differentiated or matured T cells) to remain in the subject at a detectable level for a period of time. As used herein, increasing the persistence of one or more transplanted immune cells or their progenies (e.g., NK cells or differentiated or matured T cells) refers to increasing the amount of time the transplanted immune cells are detectable in a subject after administration. For example, the in vivo persistence of one or more transplanted immune cells may be increased by at least about at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 1 month, at least about 2 months, at least about 3 months, at least about 4 months, at least about 5 months, or at least about 6 months. In addition, the in vivo persistence of one or more transplanted immune cells may be increased by at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold compared to the one or more transplanted immune cells that were not prepared by the present methods disclosed herein.

The disclosure may employ, unless indicated specifically to the contrary, methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology.*

Other features, objects, and advantages of the present disclosure are apparent in the detailed description that follows. It should be understood, however, that the detailed description, while indicating embodiments of the present disclosure, is given by way of illustration only, not limitation.

Disclosed is a membrane-bound interleukin-15 (IL-15)-IL-15Rα sushi domain chimeric polypeptide. In embodiments, the membrane-bound IL-15-IL-15Rα sushi domain chimeric polypeptide includes a signal peptide, such that when expressed from its corresponding nucleic acid, is believed to be directed to the cell membrane by virtue of its signal sequence. In embodiments, the signal sequence is cleave off, such that the displayed membrane-bound IL-15-IL-15Rα sushi domain chimeric polypeptide does not include the signal sequence. In embodiments, the membrane-bound IL-15-IL-15Rα sushi domain chimeric polypeptide includes as transmembrane domain to anchor the membrane-bound IL-15-IL-15Rα sushi domain chimeric polypeptide to the cell membrane.

Interleukin 15 (IL-15) is a is a cytokine with structural similarity to Interleukin-2 (IL-2). Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following infection by virus(es). This cytokine induces the proliferation of natural killer cells, i.e. cells of the innate immune system whose principal role is to kill virally infected cells. The protein encoded by this gene is a cytokine that regulates T and natural killer cell activation and proliferation. This cytokine and interleukin 2 share many biological activities. They are found to bind common hematopoietin receptor subunits, and may compete for the same receptor, and thus negatively regulate each other's activity. The number of CD8+ memory cells is shown to be controlled by a balance between this cytokine and IL2. This cytokine induces the activation of JAK kinases, as well as the phosphorylation and activation of transcription activators STAT3, STAT5, and STAT6. As used herein, unless expressly stated otherwise, the term "IL-15" refers to the mature form of IL-15 (i.e., without a signal peptide) or an active fragment thereof. The protein product of IL-15 can have any amino acid sequence known in the art, for example as available in the NCBI Gene ID: 3600, updated on 6 Feb. 2021, which is specifically incorporated herein by reference.

In certain embodiments, a IL-15 polypeptide refers to a polypeptide which has at least 75% sequence identity (such as, at least 75%, at least 80%, at least 90%, at least 95%, or 100% identity; e.g., 85-90%, 85-95%, 85-100%, 90-95%, 90-100%, or 95-100%) to the mature form of IL-15, or a fragment thereof that has activity similar to a full-length mature form. In embodiments, a IL-15 polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 6.

(SEQ ID NO: 6)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Interleukin 15 receptor subunit alpha (also known as CD125 or IL-15Rα) is a cytokine receptor that specifically binds interleukin 15 (IL-15) with high affinity. The receptors of IL-15 and IL-2 share two subunits, IL2R beta and IL2R gamma. IL-15Rα is structurally related to IL2R alpha, an additional IL2-specific alpha subunit for high affinity IL2 binding. Unlike IL2RA, IL-15Rα is capable of binding IL-15 with high affinity independent of other subunits, which suggests distinct roles between IL-15 and IL2. This receptor is reported to enhance cell proliferation and expression of apoptosis inhibitor BCL2L1/BCL2-XL and BCL2. As used herein, unless expressly stated otherwise, the term "IL-15Rα" refers to the mature form of IL-15Rα (i.e., without a signal peptide). The protein product of IL-15Rα can have any amino acid sequence known in the art, for example as available in the NCBI Gene ID: 3601, updated on 3 Feb. 2021, which is specifically incorporated herein by reference. Furthermore, unless stated otherwise IL-15Rα sushi domain refers to the sushi domain of IL-15Rα for example comprising or consisting of amino acid residues 49 to 162 of the full length IL-15Rα polypeptide.

In certain embodiments, a IL-15Rα polypeptide refers to a polypeptide which has at least 75% sequence identity (such as, at least 75%, at least 80%, at least 90%, at least 95%, or 100% identity; e.g., 85-90%, 85-95%, 85-100%, 90-95%, 90-100%, or 95-100%) to the mature form of IL-15Rα, or a fragment thereof that has activity similar to a full-length mature form. In embodiments, the IL-15Rα polypeptide comprises active form of IL-15Rα polypeptide from amino acid 49 to 162. In embodiments, a IL-15Rα sushi domain subunit has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 7 ITCPPPMSVEHADIWVKSYSLYSRERYICNSGFKRKAGTSSLTECVLNKATNVAHWTTP SLKCIRD (SEQ ID NO: 7). In further embodiments, a IL-15Rα sushi domain subunit has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 95

(SEQ ID NO: 95)
ITCPPPMSVEHADIWVKSYSLYSRERYICNSGFKRKAGTSSLTECVLNKAT

NVAHWTTPSLKCIRDPALVHQRPAPPSTVTTAGVTPQPESLSPSGKEPAAS

SPSSNNTAATTAAIVPGSQLMPSKSPSTGTTEISSHESSHGTPSQTTAKNW

ELTASASHQPPG.

In certain embodiments, the IL-15 and IL-15Rα sushi domain subunit can be linked as described herein. In particular embodiments, the linker sequence comprises sets of glycine and serine repeats such as Ser(Gly$_4$Ser)n (SEQ ID NO: 8), where n is a positive integer equal to or greater than 1 and less than 10. In one embodiment, the linker comprises Ser(Gly$_4$Ser)$_3$ (SEQ ID NO: 9) or Ser(Gly$_3$Ser)$_1$(Gly$_4$Ser)$_n$ (Gly$_3$Ser)$_1$ (SEQ ID NO: 10). In embodiments, the linker sequence comprises or consists of SGGGSGGGGSGGGGSGGGGSGGGS (SEQ ID NO: 11). Additional sequences can be used as linker sequences.

In embodiments, the polypeptides disclosed herein comprise a signal sequence, such as a heterologous signal sequence, for example, the IgE signal sequence, the kappa signal sequence, the CD38 signal sequence or any peptide with essentially equivalent activity.

Exemplary signal sequences are provided in Table 4 below

TABLE 4

Representative signal sequences

| Source | Sequence | SEQ ID NO: |
|---|---|---|
| IgE | MDWTWILFLVAAATRVHS | 12 |
| IL-2 (human) | MYRMQLLSCIALSLALVTNS | 13 |
| IL-2 (mouse) | MYSMQLASCVTLTLVLLVNS | 14 |
| Kappa (human) | METPAQLLFLLLLWLPDTTG | 15 |
| Kappa (mouse) | METDTLLLWVLLLWVPGSTG | 16 |
| CD8 (human) | MALPVTALLLPLALLLHAARP | 17 |

TABLE 4-continued

| Representative signal sequences | | |
|---|---|---|
| Source | Sequence | SEQ ID NO: |
| Albumin (human) | MKWVTFISLLFSSAYS | 18 |
| IL-15 | MRISKPHLRSISIQCYLCLLLNSHFLTEAGIHVFILGCFSAGLPKTEA | 19 |
| Prolactin (human) | MDSKGSSQKGSRLLLLLVVSNLLLCQGVVS | 20 |

In embodiments, the signal sequence is linked to the IL-15 subunit with a linker, such as one linkers described here. In one embodiment, the linker is the AGS (SEQ ID NO: 3) linker. In embodiments, a Myc sequence is used alone or in combination with either of the above linkers. In some embodiments, the amino acid sequence of the Myc sequence is EQKLISEEDL (SEQ ID NO: 21).

In embodiments, the polypeptides disclosed herein comprise a transmembrane domain sequence, such as a heterologous transmembrane domain, for example, a FAS transmembrane domain sequence, or an IL-7 transmembrane domain sequence, or a peptide with essentially equivalent activity.

In embodiments, the membrane-bound IL-15-IL-15Rα sushi domain chimeric polypeptide comprises a FAS transmembrane domain sequence. It is believed that this sequence results in the surface expression of a monomer membrane-bound IL-15-IL-15Rα sushi domain chimeric polypeptide. In embodiments, the FAS transmembrane domain sequence comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 22: LGWLCLLLLPIPLIVWV (SEQ ID NO: 22).

In embodiments, the FAS transmembrane domain sequence comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 42: RSNLGWLCLLLLPIPLIVWVKRKEVQKT (SEQ ID NO: 42).

In embodiments, the membrane-bound IL-15-IL-15Rα sushi domain chimeric polypeptide comprises a heterologous dimerization domain such that when expressed the membrane-bound IL-15-IL-15Rα sushi domain chimeric polypeptide forms a homodimer. In n embodiments the membrane-bound IL-15-IL-15Rα sushi domain chimeric polypeptide comprises an IL-7 transmembrane domain sequence. In embodiments, the IL-7 transmembrane domain sequence comprises a CPT sequence motif. It is believed that this sequence results in the surface expression of a homodimer membrane-bound IL-15-IL-15Rα sushi domain chimeric polypeptide that forms a stable homodimer by virtue of disulfide formation. In embodiment, the IL-7 transmembrane domain sequence comprises an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to SEQ ID NO: 23:

(SEQ ID NO: 23)
PILLTCPTISILSFFSVALLVILACVLW.

In certain embodiments, the IL-15Rα sushi domain subunit can be linked to the transmembrane anchoring domain as described herein. In particular embodiments, the linker sequence comprises sets of glycine and serine repeats such as $(Gly_4Ser)n$(SEQ ID NO: 24), where n is a positive integer equal to or greater than 1 and less than 10. In one embodiment, the linker can be $(Gly_4Ser)_1$ (SEQ ID NO: 25) or $(Gly_4Ser)_2$ (SEQ ID NO: 26) or $(Gly_4Ser)_3$ (SEQ ID NO: 102). In an embodiment, the linker sequence comprises or consists of GGGGSGGGGS (SEQ ID NO: 26).

In one embodiment, a membrane-bound IL-15-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 27.

(SEQ ID NO: 27)
MDWTWILFLVAAATRVHSEQKLISEEDLAGSNWVNVISDLKKIEDLIQSMH

IDATLYTESDVHPSCKVTAMKCFLLELQVISLESGDASIHDTVENLIILAN

NSLSSNGNVTESGCKECEELEEKNIKEFLQSFVHIVQMFINTSSGGGSGGG

GSGGGGSGGGGSGGGSITCPPPMSVEHADIWVKSYSLYSRERYICNSGFKR

KAGTSSLTECVLNKATNVAHWTTPSLKCIRDGGGGSGGGGSRSNLGWLCLL

LLPIPLIVWVKRKEVQKT.

In one embodiment, a membrane-bound IL-15-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 43.

(SEQ ID NO: 43)
MDWTWILFLVAAATRVHSAGSNWVNVISDLKKIEDLIQSMHIDATLYTESD

VHPSCKVTAMKCFLLELQVISLESGDASIHDTVENLIILANNSLSSNGNVT

ESGCKECEELEEKNIKEFLQSFVHIVQMFINTSSGGGSGGGGSGGGGSGGG

GSGGGSITCPPPMSVEHADIWVKSYSLYSRERYICNSGFKRKAGTSSLTEC

VLNKATNVAHWTTPSLKCIRDGGGGSGGGGSRSNLGWLCLLLLPIPLIVWV

KRKEVQKT.

In one embodiment, a membrane-bound IL-15-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 28.

(SEQ ID NO: 28)
NWVNVISDLKKIEDLIQSMHIDATLYTESDVHPSCKVTAMKCFLLELQVIS
LESGDASIHDTVENLIILANNSLSSNGNVTESGCKECEELEEKNIKEFLQS
FVHIVQMFINTSSGGGSGGGGSGGGGSGGGGSGGGSITCPPPMSVEHADIW
VKSYSLYSRERYICNSGFKRKAGTSSLTECVLNKATNVAHWTTPSLKCIRD
GGGGSGGGGSRSNLGWLCLLLLPIPLIVWVKRKEVQKT.

In one embodiment, a membrane-bound IL-15-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 44.

(SEQ ID NO: 44)
MDWTWILFLVAAATRVHSAGSNWVNVISDLKKIEDLIQSMHIDATLYTESD
VHPSCKVTAMKCFLLELQVISLESGDASIHDTVENLIILANNSLSSNGNVT
ESGCKECEELEEKNIKEFLQSFVHIVQMFINTSSGGGSGGGGSGGGGSGGG
GSGGGSITCPPPMSVEHADIWVKSYSLYSRERYICNSGFKRKAGTSSLTEC
VLNKATNVAHWTTPSLKCIRDGGGGSGGGGSPILLTCPTISILSFFSVALL
VILACVLW.

In one embodiment, a membrane-bound IL-15-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 29.

(SEQ ID NO: 29)
MDWTWILFLVAAATRVHSEQKLISEEDLAGSNWVNVISDLKKIEDLIQSMH
IDATLYTESDVHPSCKVTAMKCFLLELQVISLESGDASIHDTVENLIILAN
NSLSSNGNVTESGCKECEELEEKNIKEFLQSFVHIVQMFINTSSGGGSGGG
GSGGGGSGGGGSGGGSITCPPPMSVEHADIWVKSYSLYSRERYICNSGFKR
KAGTSSLTECVLNKATNVAHWTTPSLKCIRDGGGGSGGGGSPILLTCPTIS
ILSFFSVALLVILACVLW.

In one embodiment, a membrane-bound interleukin-15 (IL-15)-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 30.

(SEQ ID NO: 30)
NWVNVISDLKKIEDLIQSMHIDATLYTESDVHPSCKVTAMKCFLLELQVIS
LESGDASIHDTVENLIILANNSLSSNGNVTESGCKECEELEEKNIKEFLQS
FVHIVQMFINTSSGGGSGGGGSGGGGSGGGGSGGGSITCPPPMSVEHADIW

-continued

VKSYSLYSRERYICNSGFKRKAGTSSLTECVLNKATNVAHWTTPSLKCIRD
GGGGSGGGGSPILLTCPTISILSFFSVALLVILACVLW.

In one embodiment, a membrane-bound interleukin-15 (IL-15)-IL-15Rα sushi domain chimeric polypeptide has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 94.

(SEQ ID NO: 94)
MDWTWILFLVAAATRVHSEQKLISEEDLAGSNWVNVISDLKKIEDLIQSMH
IDATLYTESDVHPSCKVTAMKCFLLELQVISLESGDASIHDTVENLIILAN
NSLSSNGNVTESGCKECEELEEKNIKEFLQSFVHIVQMFINTSSGGGSGGG
GSGGGGSGGGGSGGGSITCPPPMSVEHADIWVKSYSLYSRERYICNSGFKR
KAGTSSLTECVLNKATNVAHWTTPSLKCIRDPALVHQRPAPPSTVTTAGVT
PQPESLSPSGKEPAASSPSSNNTAATTAAIVPGSQLMPSKSPSTGTTEISS
HESSHGTPSQTTAKNWELTASASHQPPGGGGGSGGGGSRSNLGWLCLLLLP
IPLIVWVKRKEVQKT.

The present disclosure provides for nucleic acids the encode a membrane-bound interleukin-15 (IL-15)-IL-15Rα sushi domain chimeric polypeptide described herein. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 6. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 7. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 8. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 9. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 10. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 11. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 12. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 13. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 14. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 15. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 16. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 17. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 18. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 19. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 20. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 21. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 22. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 23. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 24. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 25. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 26. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 27. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 28. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 29. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 30. In embodiments, a nucleic acid that encode a membrane-bound interleukin-15 (IL-15)-IL-15Rα sushi domain chimeric polypeptide comprises a nucleic acid that encodes an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 94.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 31

(SEQ ID NO: 31)
GCTGGAAGCAATTGGGTGAACGTGATCTCCGACCTCAAGAAGATCGAGGAT

CTGATCCAGTCCATGCACATCGATGCCACACTCTACACCGAGTCCGATGTG

CACCCTAGCTGCAAAGTTACAGCCATGAAATGCTTTCTGCTGGAGCTGCAA

GTGATCTCTCTGGAGTCCGGAGATGCTTCCATCCACGACACAGTGGAGAAT

CTGATCATTCTGGCTAACAACTCCCTCTCCAGCAACGGCAATGTCACAGAG

TCCGGCTGCAAAGAGTGTGAAGAGCTGGAGGAGAAAAACATCAAAGAGTTT

CTGCAGAGCTTCGTCCACATCGTCCAGATGTTCATCAACACCTCCTCC.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 32

(SEQ ID NO: 32)
GCCGGCAGCAACTGGGTCAACGTGATCTCCGATCTGAAGAAGATCGAAGAT

CTGATCCAGTCCATGCACATCGATGCCACACTGTACACCGAGAGCGACGTG

CACCCCAGCTGCAAAGTTACAGCCATGAAGTGCTTTCTGCTCGAACTGCAA

GTGATTTCTCTGGAGAGCGGAGATGCCAGCATCCACGACACCGTGGAGAAT

CTGATCATTCTGGCCAACAACTCTCTGAGCAGCAACGGCAATGTGACAGAG

TCCGGCTGTAAGGAGTGCGAGGAGCTGGAGGAGAAAAACATCAAAGAGTTT

CTGCAGAGCTTCGTCCACATTGTCCAAATGTTCATCAACACCAGCAGC.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 33

(SEQ ID NO: 33)
ATTACATGCCCTCCCCCCATGTCCGTGGAACATGCCGACATCTGGGTGAAG

TCCTACTCTCTGTACTCGCGTGAACGTTATATCTGCAACAGCGGCTTTAAG

AGGAAGGCCGGAACCTCCTCTCTGACCGAATGTGTGCTGAACAAGGCCACC

AATGTGGCTCACTGGACCACACCTAGCCTCAAGTGTATTAGGGAC.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 34.

(SEQ ID NO: 34)
AGAAGCAATCTGGGCTGGCTGTGTCTGCTGCTGCTCCCCATCCCTCTGAT

TGTGTGGGTCAAGAGGAAGGAGGTCCAGAAAACC.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 35.

(SEQ ID NO: 35)
CCTATTCTGCTGACATGCCCCACCATCTCCATCCTGTCTTTTTTTTCTGT

TGCTCTGCTGGTGATTCTGGCTTGCGTGCTGTGG.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 36.

(SEQ ID NO: 36)
GGCGGCGGCAGCGGCGGCGGCGGATCCGGCGGAGGAGGCAGCGGAGGAGG

AGGAAGCGGAGGAGGCTCC.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 37

(SEQ ID NO: 37)
GGCGGCGGCTCCGGCGGCGGAGGCTCCGGCGGAGGCGGATCCGGCGGCGG

CGGATCCGGCGGAGGATCC.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 38

(SEQ ID NO: 38)
GGCGGCGGAGGATCCGGAGGAGGCGGATCT.

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 39 GGCGGCGGAGGAAGCG-GAGGAGGAGGAAGC (SEQ ID NO: 39).

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 40

```
                                              (SEQ ID NO: 40)
GCTGGAAGCAATTGGGTGAACGTGATCTCCGACCTCAAGAAGATCGAGGA

TCTGATCCAGTCCATGCACATCGATGCCACACTCTACACCGAGTCCGATG

TGCACCCTAGCTGCAAAGTTACAGCCATGAAATGCTTTCTGCTGGAGCTG

CAAGTGATCTCTCTGGAGTCCGGAGATGCTTCCATCCACGACACAGTGGA

GAATCTGATCATTCTGGCTAACAACTCCCTCTCCAGCAACGGCAATGTCA

CAGAGTCCGGCTGCAAAGAGTGTGAAGAGCTGGAGGAGAAAAACATCAAA

GAGTTTCTGCAGAGCTTCGTCCACATCGTCCAGATGTTCATCAACACCTC

CTCCGGCGGCGGCAGCGGCGGCGGCGGATCCGGCGGAGGAGGCAGCGGAG

GAGGAGGAAGCGGAGGAGGCTCCATTACATGCCCTCCCCCCATGTCCGTG

GAACATGCCGACATCTGGGTGAAGTCCTACTCTCTGTACTCGCGTGAACG

TTATATCTGCAACAGCGGCTTTAAGAGGAAGGCCGGAACCTCCTCTCTGA

CCGAATGTGTGCTGAACAAGGCCACCAATGTGGCTCACTGGACCACACCT

AGCCTCAAGTGTATTAGGGACGGCGGCGGAGGATCCGGAGGAGGCGGATC

TAGAAGCAATCTGGGCTGGCTGTGTCTGCTGCTGCTCCCCATCCCTCTGA

TTGTGTGGGTCAAGAGGAAGGAGGTCCAGAAAACC.
```

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 103

```
                                             (SEQ ID NO: 103)
GCTGGAAGCAATTGGGTGAACGTGATCTCCGACCTCAAAAAGATCGAGGA

TCTGATCCAGTCCATGCACATCGATGCCACACTCTACACCGAGTCCGATG

TGCACCCTAGCTGCAAAGTTACAGCAATGAAATGCTTTCTGCTGGAGTTG

CAAGTAATCTCCCTGGAGTCCGGAGATGCTTCCATCCACGACACAGTGGA

GAATTTAATCATTCTGGCTAACAATTCCCTCTCGTCTAATGGCAATGTCA

CTGAGAGCGGCTGTAAAGAGTGTGAAGAGCTGGAGGAGAAAAACATCAAA

GAGTTTCTGCAGAGCTTCGTCCACATCGTCCAAATGTTCATCAACACCTC

GTCCGGGGGCGGCTCCGGGGGAGGAGGATCGGGGGGAGGAGGAAGCGGAG

GTGGAGGAAGCGGTGGAGGGTCCATTACATGCCCTCCCCCCATGTCCGTG

GAACATGCCGACATATGGGTAAAGTCCTACTCTCTGTACTCGCGGGAACG

TTATATCTGCAACAGCGGCTTTAAGAGAAAGGCCGGAACATCtTCTCTGA

CCGAATGTGTGCTGAACAAGGCCACAAATGTGGCTCACTGGACCACGCCT
```

-continued

```
AGCCTCAAGTGTATTAGGGACGGCGGCGGAGGTTCCGGTGGCGGGGGCTC

TAGATCGAATCTGGGCTGGCTGTGTCTGCTGCTGCTCCCCATCCCTCTGA

TTGTGTGGGTTAAGCGAAAAGAGGTCCAGAAAACCTAA
```

In embodiments, a nucleic acid encoding membrane-bound interleukin-15 (IL-15)-IL-15Rα sushi domain chimeric polypeptide comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 41

```
                                              (SEQ ID NO: 41)
GCCGGCAGCAACTGGGTCAACGTGATCTCCGATCTGAAGAAGATCGAAGA

TCTGATCCAGTCCATGCACATCGATGCCACACTGTACACCGAGAGCGACG

TGCACCCCAGCTGCAAAGTTACAGCCATGAAGTGCTTTCTGCTCGAACTG

CAAGTGATTTCTCTGGAGAGCGGAGATGCCAGCATCCACGACACCGTGGA

GAATCTGATCATTCTGGCCAACAACTCTCTGAGCAGCAACGGCAATGTGA

CAGAGTCCGGCTGTAAGGAGTGCGAGGAGCTGGAGGAGAAAAACATCAAA

GAGTTTCTGCAGAGCTTCGTCCACATTGTCCAAATGTTCATCAACACCAG

CAGCGGCGGCGGCTCCGGCGGCGGAGGCTCCGGCGGAGGCGGATCCGGCG

GCGGCGGATCCGGCGGAGGATCCATTACATGCCCCCCTCCCATGTCCGTG

GAACACGCCGACATCTGGGTGAAGAGCTACTCTCTGTACAGCAGAGAGCG

TTACATCTGCAACAGCGGCTTTAAGAGGAAAGCCGGCACCAGCAGCCTCA

CAGAGTGCGTGCTCAACAAGGCCACCAACGTCGCCCATTGGACCACCCCC

TCTCTGAAGTGTATTAGGGACGGCGGCGGAGGAAGCGGAGGAGGAGGAAG

CCCTATTCTGCTGACATGCCCCACCATCTCCATCCTGTCTTTTTTTTCTG

TTGCTCTGCTGGTGATTCTGGCTTGCGTGCTGTGGTGA.
```

In embodiments, a nucleic acid encoding membrane-bound interleukin-15 (IL-15)-IL-15Rα sushi domain chimeric polypeptide (comprising a FAS transmembrane domain and no myc tag) comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 96

```
                                              (SEQ ID NO: 96)
ATGGACTGGACATGGATTCTGTTTCTGGTGGCCGCCGCCACAAGAGTGCA

CAGCAATTGGGTGAACGTGATCTCCGACCTCAAGAAGATCGAGGATCTGA

TCCAGTCCATGCACATCGATGCCACACTCTACACCGAGTCCGATGTGCAC

CCTAGCTGCAAAGTTACAGCCATGAAATGCTTTCTGCTGGAGCTGCAAGT

GATCTCTCTGGAGTCCGGAGATGCTTCCATCCACGACACAGTGGAGAATC

TGATCATTCTGGCTAACAACTCCCTCTCCAGCAACGGCAATGTCACAGAG

TCCGGCTGCAAAGAGTGTGAAGAGCTGGAGGAGAAAAACATCAAAGAGTT

TCTGCAGAGCTTCGTCCACATCGTCCAGATGTTCATCAACACCTCCTCCG

GCGGCGGCAGCGGCGGCGGCGGATCCGGCGGAGGAGGCAGCGGAGGAGGA
```

-continued

GGAAGCGGAGGAGGCTCCATTACATGCCCTCCCCCCATGTCCGTGGAACA
TGCCGACATCTGGGTGAAGTCCTACTCTCTGTACTCGCGTGAACGTTATA
TCTGCAACAGCGGCTTTAAGAGGAAGGCCGGAACCTCCTCTCTGACCGAA
TGTGTGCTGAACAAGGCCACCAATGTGGCTCACTGGACCACACCTAGCCT
CAAGTGTATTAGGGACGGCGGCGGAGGATCCGGAGGAGGCGGATCTAGAA
GCAATCTGGGCTGGCTGTGTCTGCTGCTGCTCCCCATCCCTCTGATTGTG
TGGGTCAAGAGGAAGGAGGTCCAGAAAACCTAA.

In embodiments, a nucleic acid encoding membrane-bound interleukin-15 (IL-15)-IL-15Rα sushi domain chimeric polypeptide (comprising a IL-7 transmembrane domain and no myc tag) comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 97

(SEQ ID NO: 97)
ATGGACTGGACATGGATTCTGTTTCTGGTGGCCGCCGCCACAAGAGTGCA
CTCCAACTGGGTCAACGTGATCTCCGATCTGAAGAAGATCGAAGATCTGA
TCCAGTCCATGCACATCGATGCCACACTGTACACCGAGAGCGACGTGCAC
CCCAGCTGCAAAGTTACAGCCATGAAGTGCTTTCTGCTCGAACTGCAAGT
GATTTCTCTGGAGAGCGGAGATGCCAGCATCCACGACACCGTGGAGAATC
TGATCATTCTGGCCAACAACTCTCTGAGCAGCAACGGCAATGTGACAGAG
TCCGGCTGTAAGGAGTGCGAGGAGCTGGAGGAGAAAAACATCAAAGAGTT
TCTGCAGAGCTTCGTCCACATTGTCCAAATGTTCATCAACACCAGCAGCG
GCGGCGGCTCCGGCGGCGGAGGCTCCGGCGGAGGCGGATCCGGCGGCGGC
GGATCCGGCGGAGGATCCATTACATGCCCCCCTCCCATGTCCGTGGAACA
CGCCGACATCTGGGTGAAGAGCTACTCTCTGTACAGCAGAGAGCGTTACA
TCTGCAACAGCGGCTTTAAGAGGAAAGCCGGCACCAGCAGCCTCACAGAG
TGCGTGCTCAACAAGGCCACCAACGTCGCCCATTGGACCACCCCCTCTCT
GAAGTGTATTAGGGACGGCGGCGGAGGAAGCGGAGGAGGAGGAAGCCCTA
TTCTGCTGACATGCCCCACCATCTCCATCCTGTCTTTTTTTTCTGTTGCT
CTGCTGGTGATTCTGGCTTGCGTGCTGTGGTGA.

In embodiments, a nucleic acid encoding membrane-bound interleukin-15 (IL-15)-IL-15Rα sushi domain chimeric polypeptide (comprising a FAS transmembrane domain and no myc tag, in the context of an anti-CD19 CAR) comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 98

(SEQ ID NO: 98)
ATGCTTCTCCTGGTGACAAGCCTTCTGCTCTGTGAGTTACCACACCCAGC
ATTCCTCCTGATCCCAGACATCCAGATGACACAGACTACATCCTCCCTGT
CTGCCTCTCTGGGAGACAGAGTCACCATCAGTTGCAGGGCAAGTCAGGAC
ATTAGTAAATATTTAAATTGGTATCAGCAGAAACCAGATGGAACTGTTAA

-continued

ACTCCTGATCTACCATACATCAAGATTACACTCAGGAGTCCCATCAAGGT
TCAGTGGCAGTGGGTCTGGAACAGATTATTCTCTCACCATTAGCAACCTG
GAGCAAGAAGATATTGCCACTTACTTTTGCCAACAGGGTAATACGCTTCC
GTACACGTTCGGAGGGGGGACTAAGTTGGAAATAACAGGCTCCACCTCTG
GATCCGGCAAGCCCGGATCTGGCGAGGGATCCACCAAGGGCGAGGTGAAA
CTGCAGGAGTCAGGACCTGGCCTGGTGGCGCCCTCACAGAGCCTGTCCGT
CACATGCACTGTCTCAGGGGTCTCATTACCCGACTATGGTGTAAGCTGGA
TTCGCCAGCCTCCACGAAAGGGTCTGGAGTGGCTGGGAGTAATATGGGGT
AGTGAAACCACATACTATAATTCAGCTCTCAAATCCAGACTGACCATCAT
CAAGGACAACTCCAAGAGCCAAGTTTTCTTAAAAATGAACAGTCTGCAAA
CTGATGACACAGCCATTTACTACTGTGCCAAACATTATTACTACGGTGGT
AGCTATGCTATGGACTACTGGGGTCAAGGAACCTCAGTCACAGTCTCCTC
AGCGGCCGCAATTGAAGTTATGTATCCTCCTCCTTACCTAGACAATGAGA
AGAGCAATGGAACCATTATCCATGTGAAAGGGAAACACCTTTGTCCAAGT
CCCCTATTTCCCGGACCTTCTAAGCCCTTTTGGGTGCTGGTGGTGGTTGG
GGGAGTCCTGGCTTGCTATAGCTTGCTAGTAACAGTGGCCTTTATTATTT
TCTGGGTGAGGAGTAAGAGGAGCAGGCTCCTGCACAGTGACTACATGAAC
ATGACTCCCCGCCGCCCCGGGCCCACCCGCAAGCATTACCAGCCCTATGC
CCCACCACGCGACTTCGCAGCCTATCGCTCCAGAGTGAAGTTCAGCAGGA
GCGCAGACGCCCCCGCGTACCAGCAGGGCCAGAACCAGCTCTATAACGAG
CTCAATCTAGGACGAAGAGAGGAGTACGATGTTTTGGACAAGAGGCGTGG
CCGGGACCCTGAGATGGGGGGAAAGCCGAGAAGGAAGAACCCTCAGGAAG
GCCTGTACAATGAACTGCAGAAAGATAAGATGGCGGAGGCCTACAGTGAG
ATTGGGATGAAAGGCGAGCGCCGGAGGGGCAAGGGGCACGATGGCCTTTA
CCAGGGTCTCAGTACAGCCACCAAGGACACCTACGACGCCCTTCACATGC
AGGCCCTGCCCCCTCGCGGCTCTGGAGAGGGCAGAGGCTCTCTGCTGACC
TGCGGCGACGTGGAAGAGAACCCAGGCCCCATGGACTGGACATGGATTCT
GTTTCTGGTGGCCGCCGCCACAAGAGTGCACAGCAATTGGGTGAACGTGA
TCTCCGACCTCAAGAAGATCGAGGATCTGATCCAGTCCATGCACATCGAT
GCCACACTCTACACCGAGTCCGATGTGCACCCTAGCTGCAAAGTTACAGC
CATGAAATGCTTTCTGCTGGAGCTGCAAGTGATCTCTCTGGAGTCCGGAG
ATGCTTCCATCCACGACACAGTGGAGAATCTGATCATTCTGGCTAACAAC
TCCCTCTCCAGCAACGGCAATGTCACAGAGTCCGGCTGCAAAGAGTGTGA
AGAGCTGGAGGAGAAAAACATCAAAGAGTTTCTGCAGAGCTTCGTCCACA
TCGTCCAGATGTTCATCAACACCTCCTCCGGCGGCGGCAGCGGCGGCGGC
GGATCCGGCGGAGGAGGCAGCGGAGGAGGAGGAAGCGGAGGAGGCTCCAT
TACATGCCCTCCCCCCATGTCCGTGGAACATGCCGACATCTGGGTGAAGT
CCTACTCTCTGTACTCGCGTGAACGTTATATCTGCAACAGCGGCTTTAAG
AGGAAGGCCGGAACCTCCTCTCTGACCGAATGTGTGCTGAACAAGGCCAC
CAATGTGGCTCACTGGACCACACCTAGCCTCAAGTGTATTAGGGACGGCG

-continued

GCGGAGGATCCGGAGGAGGCGGATCTAGAAGCAATCTGGGCTGGCTGTGT

CTGCTGCTGCTCCCCATCCCTCTGATTGTGTGGGTCAAGAGGAAGGAGGT

CCAGAAAACCTAA.

In embodiments, a nucleic acid encoding membrane-bound interleukin-15 (IL-15)-IL-15Rα sushi domain chimeric polypeptide (comprising a IL-7 transmembrane domain and no myc tag, in the context of an anti-CD19 CAR) comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 99

(SEQ ID NO: 99)

ATGCTTCTCCTGGTGACAAGCCTTCTGCTCTGTGAGTTACCACACCCAGC

ATTCCTCCTGATCCCAGACATCCAGATGACACAGACTACATCCTCCCTGT

CTGCCTCTCTGGGAGACAGAGTCACCATCAGTTGCAGGGCAAGTCAGGAC

ATTAGTAAATATTTAAATTGGTATCAGCAGAAACCAGATGGAACTGTTAA

ACTCCTGATCTACCATACATCAAGATTACACTCAGGAGTCCCATCAAGGT

TCAGTGGCAGTGGGTCTGGAACAGATTATTCTCTCACCATTAGCAACCTG

GAGCAAGAAGATATTGCCACTTACTTTTGCCAACAGGGTAATACGCTTCC

GTACACGTTCGGAGGGGGGACTAAGTTGGAAATAACAGGCTCCACCTCTG

GATCCGGCAAGCCCGGATCTGGCGAGGGATCCACCAAGGGCGAGGTGAAA

CTGCAGGAGTCAGGACCTGGCCTGGTGGCGCCCTCACAGAGCCTGTCCGT

CACATGCACTGTCTCAGGGGTCTCATTACCCGACTATGGTGTAAGCTGGA

TTCGCCAGCCTCCACGAAAGGGTCTGGAGTGGCTGGGAGTAATATGGGGT

AGTGAAACCACATACTATAATTCAGCTCTCAAATCCAGACTGACCATCAT

CAAGGACAACTCCAAGAGCCAAGTTTTCTTAAAAATGAACAGTCTGCAAA

CTGATGACACAGCCATTTACTACTGTGCCAAACATTATTACTACGGTGGT

AGCTATGCTATGGACTACTGGGGTCAAGGAACCTCAGTCACAGTCTCCTC

AGCGGCCGCAATTGAAGTTATGTATCCTCCTCCTTACCTAGACAATGAGA

AGAGCAATGGAACCATTATCCATGTGAAAGGGAAACACCTTTGTCCAAGT

CCCCTATTTCCCGGACCTTCTAAGCCCTTTTGGGTGCTGGTGGTGGTTGG

GGGAGTCCTGGCTTGCTATAGCTTGCTAGTAACAGTGGCCTTTATTATTT

TCTGGGTGAGGAGTAAGAGGAGCAGGCTCCTGCACAGTGACTACATGAAC

ATGACTCCCCGCCGCCCCGGGCCCACCCGCAAGCATTACCAGCCCTATGC

CCCACCACGCGACTTCGCAGCCTATCGCTCCAGAGTGAAGTTCAGCAGGA

GCGCAGACGCCCCCGCGTACCAGCAGGGCCAGAACCAGCTCTATAACGAG

CTCAATCTAGGACGAAGAGAGGAGTACGATGTTTTGGACAAGAGGCGTGG

CCGGGACCCTGAGATGGGGGGAAAGCCGAGAAGGAAGAACCCTCAGGAAG

GCCTGTACAATGAACTGCAGAAAGATAAGATGGCGGAGGCCTACAGTGAG

ATTGGGATGAAAGGCGAGCGCCGGAGGGGCAAGGGGCACGATGGCCTTTA

CCAGGGTCTCAGTACAGCCACCAAGGACACCTACGACGCCCTTCACATGC

AGGCCCTGCCCCCTCGCGGCTCTGGAGAGGGCAGAGGCTCTCTGCTGACC

TGCGGCGACGTGGAAGAGAACCCAGGCCCCATGGACTGGACATGGATTCT

-continued

GTTTCTGGTGGCCGCCGCCACAAGAGTGCACTCCAACTGGGTCAACGTGA

TCTCCGATCTGAAGAAGATCGAAGATCTGATCCAGTCCATGCACATCGAT

GCCACACTGTACACCGAGAGCGACGTGCACCCCAGCTGCAAAGTTACAGC

CATGAAGTGCTTTCTGCTCGAACTGCAAGTGATTTCTCTGGAGAGCGGAG

ATGCCAGCATCCACGACACCGTGGAGAATCTGATCATTCTGGCCAACAAC

TCTCTGAGCAGCAACGGCAATGTGACAGAGTCCGGCTGTAAGGAGTGCGA

GGAGCTGGAGGAGAAAAACATCAAAGAGTTTCTGCAGAGCTTCGTCCACA

TTGTCCAAATGTTCATCAACACCAGCAGCGGCGGCGGCTCCGGCGGCGGA

GGCTCCGGCGGAGGCGGATCCGGCGGCGGCGGATCCGGCGGAGGATCCAT

TACATGCCCCCCTCCCATGTCCGTGGAACACGCCGACATCTGGGTGAAGA

GCTACTCTCTGTACAGCAGAGAGCGTTACATCTGCAACAGCGGCTTTAAG

AGGAAAGCCGGCACCAGCAGCCTCACAGAGTGCGTGCTCAACAAGGCCAC

CAACGTCGCCCATTGGACCACCCCCTCTCTGAAGTGTATTAGGGACGGCG

GCGGAGGAAGCGGAGGAGGAGGAAGCCCTATTCTGCTGACATGCCCCACC

ATCTCCATCCTGTCTTTTTTTTCTGTTGCTCTGCTGGTGATTCTGGCTTG

CGTGCTGTGGAAGAAGAGGATCAAGCCGATAGTTTGA.

In embodiments, a nucleic acid encoding membrane-bound interleukin-15 (IL-15)-IL-15Rα sushi domain chimeric polypeptide (comprising a FAS transmembrane domain and no myc tag) comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 100

(SEQ ID NO: 100)

ATGGACTGGACCTGGATACTTTTCCTGGTGGCCGCCGCTACCAGAGTTCA

CTCAAATTGGGTCAATGTAATTTCAGACTTGAAGAAGATCGAAGATCTGA

TCCAGTCTATGCATATAGATGCTACTCTGTACACTGAGTCCGATGTGCAT

CCGTCCTGTAAAGTGACAGCCATGAAGTGTTTCCTGCTTGAGCTCCAAGT

TATCAGTCTCGAATCCGGCGATGCCTCAATACATGATACTGTAGAGAACC

TCATCATTCTCGCAAACAATTCCCTGTCAAGCAATGGAAATGTTACGGAG

TCAGGTTGTAAAGAATGTGAGGAATTGGAAGAAAAGAACATAAAAGAGTT

CTTGCAGAGTTTCGTGCACATCGTACAAATGTTCATCAATACGAGTAGTG

GTGGTGGTTCCGGAGGAGGAGGATCTGGCGGAGGCGGTAGTGGTGGAGGA

GGATCCGGAGGTGGGAGTATAACTTGTCCGCCGCCCATGAGTGTGGAACA

TGCTGATATATGGGTAAAGTCTTATTCACTTTATAGCAGAGAACGCTATA

TTTGTAATTCTGGCTTCAAGCGAAAAGCTGGCACGAGCAGTCTCACGGAG

TGCGTCCTGAACAAGGCAACCAACGTCGCGCATTGGACAACTCCTAGCCT

CAAATGCATAAGGGACCCTGCACTGGTGCACCAACGCCCTGCGCCACCGT

CAACGGTCACTACAGCTGGCGTTACACCGCAGCCAGAATCTTTGAGTCCA

TCAGGCAAGGAACCCGCGGCGTCTTCCCCGTCTTCTAACAATACCGCCGC

AACGACGGCGGCAATCGTGCCGGGATCACAACTCATGCCTTCCAAAAGTC

CCTCAACGGGCACGACAGAGATTAGCAGCCACGAAAGCTCCCATGGCACT

-continued

```
CCCTCACAAACGACCGCGAAGAACTGGGAGCTGACTGCAAGTGCATCTCA
CCAGCCACCGGGTGGCGGGGGTGGATCAGGTGGCGGTGGCTCTCGCTCCA
ACCTCGGTTGGCTTTGCCTTCTTTTGCTGCCCATACCGTTGATCGTCTGG
GTTAAGCGCAAAGAAGTCCAGAAAACTTAA.
```

In embodiments, a nucleic acid encoding membrane-bound interleukin-15 (IL-15)-IL-15Rα sushi domain chimeric polypeptide (comprising a FAS transmembrane domain and no myc tag, in the context of an anti-CD19 CAR) comprises the nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 101

```
                                        (SEQ ID NO: 101)
ATGCTTCTCCTGGTGACAAGCCTTCTGCTCTGTGAGTTACCACACCCAGC
ATTCCTCCTGATCCCAGACATCCAGATGACACAGACTACATCCTCCCTGT
CTGCCTCTCTGGGAGACAGAGTCACCATCAGTTGCAGGGCAAGTCAGGAC
ATTAGTAAATATTTAAATTGGTATCAGCAGAAACCAGATGGAACTGTTAA
ACTCCTGATCTACCATACATCAAGATTACACTCAGGAGTCCCATCAAGGT
TCAGTGGCAGTGGGTCTGGAACAGATTATTCTCTCACCATTAGCAACCTG
GAGCAAGAAGATATTGCCACTTACTTTTGCCAACAGGGTAATACGCTTCC
GTACACGTTCGGAGGGGGGACTAAGTTGGAAATAACAGGCTCCACCTCTG
GATCCGGCAAGCCCGGATCTGGCGAGGGATCCACCAAGGGCGAGGTGAAA
CTGCAGGAGTCAGGACCTGGCCTGGTGGCGCCCTCACAGAGCCTGTCCGT
CACATGCACTGTCTCAGGGGTCTCATTACCCGACTATGGTGTAAGCTGGA
TTCGCCAGCCTCCACGAAAGGGTCTGGAGTGGCTGGGAGTAATATGGGGT
AGTGAAACCACATACTATAATTCAGCTCTCAAATCCAGACTGACCATCAT
CAAGGACAACTCCAAGAGCCAAGTTTTCTTAAAAATGAACAGTCTGCAAA
CTGATGACACAGCCATTTACTACTGTGCCAAACATTATTACTACGGTGGT
AGCTATGCTATGGACTACTGGGGTCAAGGAACCTCAGTCACAGTCTCCTC
AGCGGCCGCAATTGAAGTTATGTATCCTCCTCCTTACCTAGACAATGAGA
AGAGCAATGGAACCATTATCCATGTGAAAGGGAAACACCTTTGTCCAAGT
CCCCTATTTCCCGGACCTTCTAAGCCCTTTTGGGTGCTGGTGGTGGTTGG
GGGAGTCCTGGCTTGCTATAGCTTGCTAGTAACAGTGGCCTTTATTATTT
TCTGGGTGAGGAGTAAGAGGAGCAGGCTCCTGCACAGTGACTACATGAAC
ATGACTCCCCGCCGCCCCGGGCCCACCCGCAAGCATTACCAGCCCTATGC
CCCACCACGCGACTTCGCAGCCTATCGCTCCAGAGTGAAGTTCAGCAGGA
GCGCAGACGCCCCCGCGTACCAGCAGGGCCAGAACCAGCTCTATAACGAG
CTCAATCTAGGACGAAGAGAGGAGTACGATGTTTTGGACAAGAGGCGTGG
CCGGGACCCTGAGATGGGGGGAAAGCCGAGAAGGAAGAACCCTCAGGAAG
GCCTGTACAATGAACTGCAGAAAGATAAGATGGCGGAGGCCTACAGTGAG
ATTGGGATGAAAGGCGAGCGCCGGAGGGGCAAGGGGCACGATGGCCTTTA
CCAGGGTCTCAGTACAGCCACCAAGGACACCTACGACGCCCTTCACATGC
```

-continued

```
AGGCCCTGCCCCCTCGCAGAGCCAAGAGAGGCTCCGGAGAGGGCAGAGGC
TCTCTGCTGACCTGCGGCGACGTGGAAGAGAATCCAGGGCCCATGGACTG
GACCTGGATACTTTTCCTGGTGGCCGCCGCTACCAGAGTTCACTCAAATT
GGGTCAATGTAATTTCAGACTTGAAGAAGATCGAAGATCTGATCCAGTCT
ATGCATATAGATGCTACTCTGTACACTGAGTCCGATGTGCATCCGTCCTG
TAAAGTGACAGCCATGAAGTGTTTCCTGCTTGAGCTCCAAGTTATCAGTC
TCGAATCCGGCGATGCCTCAATACATGATACTGTAGAGAACCTCATCATT
CTCGCAAACAATTCCCTGTCAAGCAATGGAAATGTTACGGAGTCAGGTTG
TAAAGAATGTGAGGAATTGGAAGAAAAGAACATAAAAGAGTTCTTGCAGA
GTTTCGTGCACATCGTACAAATGTTCATCAATACGAGTAGTGGTGGTGGT
TCCGGAGGAGGAGGATCTGGCGGAGGCGGTAGTGGTGGAGGAGGATCCGG
AGGTGGGAGTATAACTTGTCCGCCGCCCATGAGTGTGGAACATGCTGATA
TATGGGTAAAGTCTTATTCACTTTATAGCAGAGAACGCTATATTTGTAAT
TCTGGCTTCAAGCGAAAAGCTGGCACGAGCAGTCTCACGGAGTGCGTCCT
GAACAAGGCAACCAACGTCGCGCATTGGACAACTCCTAGCCTCAAATGCA
TAAGGGACCCTGCACTGGTGCACCAACGCCCTGCGCCACCGTCAACGGTC
ACTACAGCTGGCGTTACACCGCAGCCAGAATCTTTGAGTCCATCAGGCAA
GGAACCCGCGGCGTCTTCCCCGTCTTCTAACAATACCGCCGCAACGACGG
CGGCAATCGTGCCGGGATCACAACTCATGCCTTCCAAAAGTCCCTCAACG
GGCACGACAGAGATTAGCAGCCACGAAAGCTCCCATGGCACTCCCTCACA
AACGACCGCGAAGAACTGGGAGCTGACTGCAAGTGCATCTCACCAGCCAC
CGGGTGGCGGGGGTGGATCAGGTGGCGGTGGCTCTCGCTCCAACCTCGGT
TGGCTTTGCCTTCTTTTGCTGCCCATACCGTTGATCGTCTGGGTTAAGCG
CAAAGAAGTCCAGAAAACTTAA.
```

The present disclosure provides methods and compositions for improving the efficacy of antigen binding systems, such as CARs and TCRs, comprising a binding motif that binds to an antigen of interest, e.g., a tumor antigen. In certain embodiments, the antigen binding system is a chimeric antigen receptor (CAR). In certain embodiments, the antigen binding system is a T-cell receptor (TCR). The antigen binding system can bind to a tumor antigen or a pathogen antigen.

Chimeric antigen receptors (CARs) are engineered receptors that may direct or redirect T cells (e.g., patient or donor T cells) to target a selected antigen. A CAR may be engineered to recognize an antigen and, when bound to that antigen, activate the immune cell to attack and destroy the cell bearing that antigen. When these antigens exist on tumor cells, an immune cell that expresses the CAR may target and kill the tumor cell. CARs generally comprise an extracellular binding motif that mediates antigen binding, a transmembrane domain that spans, or is understood to span, the cell membrane when the antigen binding system is present at a cell surface or cell membrane, and an intracellular (or cytoplasmic) signaling domain.

According to at least one non-limiting view, there have been at least three "generations" of CAR compositions. In a first generation of CARs, a binding motif (e.g., a single chain fragment variable, binding motif) is linked or connected to a signaling domain (e.g., CD3ζ) via a transmembrane domain, optionally comprising a hinge domain and one or more spacers. In a second generation of CARs, a costimulatory domain (such as CD28, 4-1BB, or OX-40) is introduced with the signaling domain (e.g., CD3ζ). In a third generation of CARs, a second costimulatory domain is included.

TCRs are heterodimers composed of an α-chain and a β-chain. TCR signaling requires recruitment of signaling proteins that generate an immune synapse. In addition, TCR localization at the plasma membrane depends on CD3 complex, which is expressed in T cells. Engineered single chain TCRs may be generated, e.g., using transmembrane and signaling domains of CAR constructs, methods and constructs for which are known (e.g., sTCR and TCR-CAR molecules, e.g., fusion of a TCRβ chain with CD28 TM and CD28 and CD3ζ (signaling modules).

The antigen binding system may comprise a VH and a VL. In some embodiments, the VH and the VL are connected by a linker (L).

In some embodiments, an antigen binding system further comprises a costimulatory domain, and/or an extracellular domain (e.g., a "hinge" or "spacer" region), and/or a transmembrane domain, and/or an intracellular (signaling) domain, and/or a CD3-zeta or CD3-episilon activation domain.

One or more antigen binding motifs determine the target(s) of an antigen binding system. A binding motif of an antigen binding system may comprise any binding motif. Binding motifs are used in chimeric antigen receptors at least in part because they may be engineered to be expressed as part of a single chain along with the other CAR components. See, for example, U.S. Pat. Nos. 7,741,465, and 6,319,494 as well as Eshhar et al., Cancer Immunol Immunotherapy (1997) 45: 131-136, Krause et al., J. Exp. Med., Volume 188, No. 4, 1998 (619-626); Finney et al., Journal of Immunology, 1998, 161: 2791-2797, each of which is incorporated herein by reference with respect to binding motif domains in CARs. A binding motif, or scFv, is a single chain antigen binding fragment comprising a heavy chain variable domain and a light chain variable domain, which heavy chain variable domain and light chain variable domain are linked or connected together. See, for example, U.S. Pat. Nos. 7,741,465, and 6,319,494 as well as Eshhar et al., Cancer Immunol Immunotherapy (1997) 45: 131-136, each of which is incorporated herein by reference with respect to binding motif domains. When derived from a parent antibody, a binding motif may retain some of, retain all of, or essentially retain the parent antibody's binding of a target antigen.

In various embodiments, the binding motif binds to a tumor antigen. In certain embodiments, the tumor antigen is selected from the group consisting of 2B4 (CD244), 4-1BB, 5T4, A33 antigen, adenocarcinoma antigen, adrenoceptor beta 3 (ADRB3), A kinase anchor protein 4 (AKAP-4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl)), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-0-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PDL-1, B7H1), CD279 (PD-1), CD352, CD358, CD300 molecule-like family member f (CD300LF), Carcinoembryonic antigen (CEA), claudin 6 (CLDN6), TACI, C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1, CRACC, CD319, and 19A24), CTLA-4, Cyclin B 1, chromosome X open reading frame 61 (CXORF61), Cytochrome P450 1B 1 (CYP1B1), DNAM-1 (CD226), desmoglein 4, DR3, DR5, E-cadherin neoepitope, epidermal growth factor receptor (EGFR), EGF1R, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FCRL5), fetal acetylcholine receptor (AChR), fibronectin extra domain-B, Fms-Like Tyrosine Kinase 3 (FLT3), folate-binding protein (FBP), folate receptor 1, folate receptor α, Folate receptor β, Fos-related antigen 1, Fucosyl, Fucosyl GM1; GM2, ganglioside G2 (GD2), ganglioside GD3 (aNeu5Ac(2-8) aNeu5Ac(2-3)bDGalp(l-4)bDGlcp(l-l)Cer), o-acetyl-GD2 ganglioside (OAcGD2), GITR (TNFRSF 18), GM1, ganglioside GM3 (aNeu5Ac(2-3)bDGalp(l-4)bDGlcp(l-l)Cer), GP 100, hexasaccharide portion of globoH glycoceramide (GloboH), glycoprotein 75, Glypican-3 (GPC3), glycoprotein 100 (gpl00), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papilloma virus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-11Ra), IL-13, Interleukin-13 receptor subunit alpha-2(IL-13Ra2 or CD213A2), insulin-like growth factor I receptor (IGF1-R), integrin α5β1, integrin αvβ3, intestinal carboxyl esterase, κ-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2(LILRA2), legumain, Leukocyte-associated immunoglobulin-like receptor 1 (LAIR1), Lewis(Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MART1, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUC5AC, MUC5b, MUC7, MUC16, mucin CanAg, Mullerian inhibitory substance (MIS) receptor type IL, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma X breakpoint 2 (SSX2), Survivin, Tumor-associated glycoprotein 72 (TAG72), TCRa, TCRb, TCR5γ, TCR Gamma Alternate Reading Frame Protein (TARP), telomerase, TIGIT, TNF-α precursor, tumor endothelial marker 1 (TEM1/CD248), tumor endothelial marker 7-related (TEM7R), tenascin C, TGF beta 2, TGF-β, transglutaminase 5 (TGS5), angiopoietin-binding cell surface receptor 2 (Tie 2), TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, ROR1, TAG-72, uroplakin 2 (UPK2), VEGF-A, VEGFR-1, vascular endothelial growth factor receptor 2 (VEGFR2), and vimentin, Wilms tumor protein (WT1), or X Antigen Family Member 1A (XAGE1). See also International Patent Application Publication No. WO2015/142675.

A CAR may comprise one or more antigen binding domains that bind a target antigen. In certain embodiments, the antigen binding domain binds CD19. In certain embodiments, the antigen binding domain binds CD20. In some embodiments, the CAR further comprises a costimulatory domain, and/or an extracellular domain (e.g., a "hinge" or "spacer" region), and/or a transmembrane domain, and/or an intracellular (signaling) domain, and/or a CD3 activation domain. In some embodiments, the CAR comprises at least a binding domain that binds a terget antigen, a costimulatory domain, an extracellular domain, a transmembrane domain, and a CD3-zeta or CD3-epsilon activating domain.

In certain embodiments, the CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers ($G_{1-5}S_{1-5}$)n, where n is an integer of at least one, two, three, four, or five (SEQ ID NO: 109); glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine, and is much less restricted than residues with longer side chains (see Scheraga, *Rev. Computational Chem.* 11173-142 (1992)). Other linkers contemplated herein include Whitlow linkers (see Whitlow, *Protein Eng.* 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker (SEQ ID NO: 104). In another embodiment, any of the constructs described herein comprise a "GSG" linker. In an example a glycine-serine linker comprises or consists of the amino acid sequence GS (SEQ ID NO: 104). In an example a glycine-serine linker comprises or consists of the amino acid sequence GGGSGGGS (SEQ ID NO: 105). In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 45 (GSTSGSGKPGSGEGSTKG (SEQ ID NO: 45). In an embodiment, a linker is encoded by a nucleic acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid sequence according to

```
                                         (SEQ ID NO: 47)
GGCTCCACCTCTGGATCCGGCAAGCCCGGATCTGGCGAGGGATCCACCAA

GGGC,

                                         (SEQ ID NO: 46)
GGGAGCACTAGCGGCTCTGGCAAACCTGGATCTGGCGAGGGATCTACCAA

GGGC

                                         (SEQ ID NO: 48)
GGCTCCACCAGCGGAAGCGGCAAGCCAGGCTCAGGCGAAGGATCTACAAA

AGGC,
or

                                         (SEQ ID NO: 49)
GGGAGCACAAGCGGCTCTGGCAAACCTGGATCCGGCGAGGGATCTACCAA

GGGC.
```

In embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy,* 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A hinge may be an extracellular domain of an antigen binding system positioned between the binding motif and the transmembrane domain. A hinge may also be referred to as an extracellular domain or as a "spacer." A hinge may contribute to receptor expression, activity, and/or stability. In some embodiments, a hinge domain is positioned between a binding motif and a transmembrane domain. A hinge may also provide flexibility to access the targeted antigen. Hinges comprise immunoglobulin-like hinge domains. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region. In some embodiments, an antigen binding system may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof.

A hinge may be derived from a natural source or from a synthetic source. In some embodiments, an antigen binding system may comprise a hinge that is, is from, or is derived from (e.g., comprises all or a fragment of) CD2, CD3 delta, CD3 epsilon, CD3 gamma, CD4, CD7, CD8 alpha, CD8 beta, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof.

In some embodiments, a CAR may comprise a hinge that is, is from, or is derived from (e.g., comprises all or a fragment of) a hinge of CD8 alpha. In some embodiments, a CAR may comprise a hinge that is, is from, or is derived from (e.g., comprises all or a fragment of) a hinge of CD28. In some embodiments, a hinge is, is from, or is derived from a fragment of a hinge of CD8 alpha or a fragment of a hinge of CD28, wherein the fragment is anything less than the whole. In some embodiments, a fragment of a CD8 alpha hinge or a fragment of a CD28 hinge comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of a CD8 alpha hinge, or of a CD28 hinge.

In embodiments, the hinge domain comprises a CD28 hinge region. In embodiments a CD28 hinge domain has the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 230 (IEVMYPPPYLD-NEKSNGTIIHVKGKHLCPSPLFPGPSKP (SEQ ID NO: 50)). In embodiments, a CD28 hinge domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to

```
                                        (SEQ ID NO: 51)
attgaagttatgtatcctcctccttacctagacaatgagaagagcaatgg
aaccattatccatgtgaaagggaaacacctttgtccaagtcccctatttc
ccggaccttctaagccc.
```

In embodiments, the hinge domain comprises a truncated CD28 hinge region (CD28T) hinge region, such as disclosed in International Patent Application No: PCT/US2017/025351, filed Mar. 31, 2017, which is incorporated herein by reference in its entirety. In embodiments a CAR comprises a CD28T hinge domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 52 (LD-NEKSNGTIIHVKGKHLCPSPLFPGPSKP (SEQ ID NO:

52)). In embodiments, a CD28T hinge domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 53)
ctagacaatgagaagagcaatggaaccattatccatgtgaaagggaaaca cctttgtccaagtcccctatttcccggaccttctaagccc.

In embodiments, the hinge domain comprises a CD8α hinge region. In embodiments the CARs described herein comprise a hinge domain from CD8α having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 54 (FVPVFLPAK-PTTTPAPRPPTPAPTIASQPLSLRPEACR-PAAGGAVHTRGLDFACD (SEQ ID NO: 54)). In embodiments, hinge domain from CD8α is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 55)
TTCGTGCCTGTGTTCCTGCCTGCTAAGCCCACCACCACTCCTGCTCCAAG

ACCTCCTACCCCCGCTCCTACAATCGCCAGCCAACCTCTGAGCCTGAGAC

CGGAGGCATGCAGACCTGCGGCAGGGGGAGCAGTTCACACAAGAGGCTTG

GACTTCGCTTGCGAC.

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort and Prosite are exemplary of such programs.

The type of transmembrane domain comprised in an antigen binding system described herein is not limited to any type. In some embodiments, a transmembrane domain is selected that is naturally associated with a binding motif and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex.

A transmembrane domain may be derived either from a natural or from a synthetic source.

Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet (SEQ ID NO: 104).

In embodiments, the CARs described herein comprise a TM domain from CD28 having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 56 (FWVLVVVGGV-LACYSLLVTVAFIIFWV (SEQ ID NO: 56)). In embodiments, a TM domain from CD28 is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to

```
                                    (SEQ ID NO: 57)
ttttgggtgctggtggtggttgggggagtcctggcttgctatagcttgct

agtaacagtggcctttattattttctgggtg.
```

In embodiments, the CARs described herein comprise a TM and intercellular domain from CD8α having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 58 IYI-WAPLAGTCGVLLLSLVITLYCNHRN (SEQ ID NO: 58)). In embodiments, the TM domain from CD8α is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to

```
                                    (SEQ ID NO: 59)
ATCTACATCTGGGCCCCTCTGGCCGGCACATGCGGAGTTCTTCTTCTTAG

CCTGGTGATCACCCTGTACTGCAACCACAGAAAC.
```

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known nucleotide sequence. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence. Optionally, short spacers may form linkages between any or some of the extracellular, transmembrane, and intracellular domains of the CAR.

The intracellular domain (or cytoplasmic domain) comprises one or more signaling domains that, upon binding of target antigen to the binding motif, cause and/or mediate an intracellular signal, e.g., that activates one or more immune cell effector functions (e.g., native immune cell effector functions). In some embodiments, signaling domains of an intracellular domain mediate activation at least one of the normal effector functions of the immune cell. Effector function of a T cell, for example, may be cytolytic activity or helper activity comprising the secretion of cytokines. In some embodiments, signaling domains of an intracellular domain mediate T cell activation, proliferation, survival, and/or other T cell function. An intracellular domain may comprise a signaling domain that is an activating domain. An intracellular domain may comprise a signaling domain that is a costimulatory signaling domain.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises an immunoreceptor tyrosine-based activation domain (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

In some embodiments, a signaling domain and/or activation domain comprises an immunoreceptor tyrosine-based activation motif (ITAM). Examples of ITAM containing cytoplasmic signaling sequences comprise those derived from TCR zeta, FcR gamma, FcR beta, CD3 zeta, CD3 gamma, CD3 delta, CD3 epsilon, CD5, CD22, CD79a, CD79b, and CD66d (see, e.g., Love et al., Cold Spring Harb. Perspect. Biol. 2:a002485 (2010); Smith-Garvin et al., Annu. Rev. Immunol. 27:591-619 (2009)). In some embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain. In one embodiment, the CARs have a CD3ζ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 60. VKFSR-SADAPAYQQGQNQLYNELNLGRREEYDVLDKRR-GRDPEMGGKPRRKNPQEGL YNELQKDKMAEAYSEI-GMKGERRRGKGHDGLYQGLSTATKDTYDALHMQALP-PR (SEQ ID NO: 60). In embodiments, a CD3ζ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to AGAGT-GAAGTTCAGCAGGAGCGCA-GACGCCCCCGCGTACCAGCAGGGCCAGAACC AGCTCTATAACGAGCT-CAATCTAGGACGAAGAGAGGAGTAC-GATGTrTTGGACAAG AGGCGTGGCCGGGACCCT-GAGATGGGGGGAAAGCCGAGAAGGAAGAACCCT-CAGG AAGGCCTGTACAATGAACTGCAGAAAGA-TAAGATGGCGGAGGCCTACAGTGAGAT TGGGAT-GAAAGGCGAGCGCCGGAGGGGCAAGGGGCAC-GATGGCCTTTACCAGGGT CTCAGTACAGCCACCAAGGACACC-TACGACGCCCTTCACATGCAGGCCCTGCCCCC TCGC (SEQ ID NO: 61). In embodiments, a CD3ζ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 106)

```
AGAGTTAAGTTCAGCAGGAGCGCCGACGCCCCTGCCTACCAGCAAGGACA

GAATCAACTGTACAACGAGCTGAACCTGGGCAGACGGGAGGAATACGATG

TGCTGGACAAGAGGAGAGGCAGAGACCCCGAGATGGGCGGCAAACCTAGA

AGAAAGAACCCCCAGGAGGGCCTGTATAACGAGCTCCAGAAGGACAAGAT

GGCCGAGGCCTACAGCGAGATCGGCATGAAGGGCGAAAGAAGAAGAGGCA

AGGGCCACGACGGCCTCTACCAGGGCTTAAGCACAGCTACAAAGGACACC

TACGACGCCCTGCACATGCAGGCCCTGCCCCCTAGA.
```

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

In certain embodiments, suitable signaling domains comprise, without limitation, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DAP-12, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

A CAR may comprise a costimulatory signaling domain, e.g., to increase signaling potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Signals generated through a TCR alone may be insufficient for full activation of a T cell and a secondary or co-stimulatory signal may increase activation. Thus, in some embodiments, a signaling domain further comprises one or more additional signaling domains (e.g., costimulatory signaling domains) that activate one or more immune cell effector functions (e.g., a native immune cell effector function described herein). In some embodiments, a portion of such costimulatory signaling domains may be used, as long as the portion transduces the effector function signal. In some embodiments, a cytoplasmic domain described herein comprises one or more cytoplasmic sequences of a T cell co-receptor (or fragment thereof). Non-limiting examples of co-stimulatory domains include, but are not limited to, 4-4BB (also known as TNFRSF9, CD137, CDw137, ILA, and tumor necrosis factor receptor superfamily member 9), 4-1BBL/CD137, BAFFR, BLAME (SLAMF8), activating NK receptors, BTLA (also known as CD272 and BTLA1), CARD11, CD2 (also known as LFA-2, SRBC, T11, and CD2 molecule), CD3 gamma, CD3 delta, CD3 epsilon, CD4, CD7 (also known as GP40, LEU-9, TP41, Tp40, and CD7 molecule), CD8alpha, CD8beta, CD11a, CD11b, CD11c, CD11d, CD18, CD19, CD19a, CD27 (also known as S152, S152.LPFS2, T14, TNFRSF7, and Tp55), CD28 (also known as Tp44), CD29, CD30 (also known as TNFRSF8, D1S166E, and Ki-1), CD40L (also known as CD40LG, CD154, HIGM1, IGM, IMD3, T-BAM, TNFSF5, TRAP, gp39, hCD40L, and CD40 ligand), CD40 (also known as Bp50, CDW40, TNFRSF5, p50, CD40 (protein), and CD40 molecule), CD49a, CD49D, CD49f, CD54 (ICAM), CD69, CD80 (also known as B7, B7-1, B7.1, BB1, CD28LG, CD28LG1, LAB7, and CD80 molecule), CD83 (and a ligand that specifically binds with CD83), CD84, CD86, CD96 (Tactile), CD100 (SEMA4D), CD103, CD160 (also known as BY55, NK1, NK28, and CD160 molecule), CD244 (also known as 2B4, NAIL, NKR2B4, Nmrk, SLAMF4, and CD244 molecule), CD247, CD276 (also known as, B7-H3,4Ig-B7-H3, B7H3, B7RP-2), CD366, CDS, CEACAM1, CRT AM, cytokine receptors, DAP10, DNAM1 (CD226), Fc gamma receptor, GADS, GITR (also known as TNFRSF18, RP5-902P8.2, AITR, CD357, and GITR-D), GITRL, HVEM (also known as TNFRSF14, RP3-395M20.6, ATAR, CD270, HVEA, HVEM, LIGHTR, and TR2), ICAM-1, ICOS (also known as inducible T cell costimulatory, AILIM, CD278, and CVID1), Ig alpha (CD79a), IL2R beta, IL2R gamma, IL7R alpha, immunoglobulin-like proteins, integrins, ITGA4, IA4, ITGA6, ITGAD, ITGAE, ITGAL, ITGAM, ITGAX, ITGB 1, ITGB2, ITGB7, KIRDS2, LAG3 (also known as CD223 and lymphocyte activating 3), LAT, LFA-1 (also known as Lymphocyte function-associated antigen 1 and CDl 1a/CD18), LIGHT (also known as TNFSF14, CD258, HVEML, LTg, TR2, TNLGID, and tumor necrosis factor superfamily member 14), LTBR, Ly9 (CD229), MHC class I molecule, NKG2C (also known as CD314, D12S2489E, KLR, NKG2-D, NKG2D, and killer cell lectin like receptor Ki), NKG2D, NKp30, NKp44, NKp46, NKp80 (KLRF1), OX40 (also known as TNFRSF4, ACT35, RP5-902P8.3, IMD16, CD134, TXGP1L, and tumor necrosis factor receptor superfamily member 4), PAG/Cbp, PD-1 (also known as PDCD1, CD279, PD-1, SLEB2, hPD-1, hPD-1, hSLE1, and Programmed cell death 1), PD-L1 (also known as CD274, B7-H, B7H1, PD-L1, PDCD1L1, PDCD1LG1, PDL1, CD274 molecule, and Programmed cell death 1 ligand 1), PSGL1, SELPLG (CD162), signaling lymphocytic activation molecules (SLAM proteins such as SLAM (SLAMF1, CD150, IPO-3), SLAMF4 (CD244, 2B4), SLAMF6 (NTB-A, Lyl08), and SLAMF7), SLP76, TIM3 (also known as HAVCR2, HAVcr-2, KIM-3, TIM3, TIMD-3, TIMD3, Tim-3, and hepatitis A virus cellular receptor 2), TNF receptor proteins, TNFR2, Toll ligand receptor, TLR1, TLR2, TLR3, TLR4, TLR5, TLR6, TLR7, TLR8, TLR9, TLR10, TNFR2, TRANCE/RANKL, TRIM, VLAl, VLA-6, and ZAP70. An exemplary costimulatory protein has the amino acid sequence of a costimulatory protein found naturally on T cells, the complete native amino acid sequence of which costimulatory protein is described in NCBI Reference Sequence: NP_006130.1. In certain instances, a CAR comprises a 4-1BB costimulatory domain.

In embodiments, the CARs comprise a CD28 costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 62. RSKRSRLLHSDYMNMTPRRPGPTRKHYQPYAPPRDFAAYRS (SEQ ID NO: 62). In embodiments, a CD28 costimulatory domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to (SEQ ID NO: 63)
aggagtaagaggagcaggctcctgcacagtgactacatgaacatgactcc ccgccgccccgggcccacccgcaagcattaccagccctatgccccaccac gcgacttcgcagcctatcgctcc.

In embodiments, the CARs comprise a 4-1BB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 64. RFSVVKRGRKKLLYIFKQPFMRPVQTTQEEDGCSCRFPEEEEGGCEL (SEQ ID NO: 64). In embodiments, a 4-IBB costimulatory domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) to the nucleic acid having the sequence according to (SEQ ID NO: 65)
AGATTCAGCGTTGTGAAGAGAGGCCGGAAGAAGCTGCTGTACATCTTCAA

GCAGCCCTTCATGAGACCTGTGCAGACCACACAGGAGGAAGACGGCTGCA

GCTGTAGATTCCCCGAGGAAGAGGAGGGCGGCTGTGAGCTG.

The engineered CARs described herein may also comprise an N-terminal signal peptide or tag at the N-terminus of the scFv or antigen binding domain. In one embodiment, a heterologous signal peptide may be used. The antigen binding domain or scFV may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly any known tag sequence known in the art may also be used. In one embodiment a signal sequence is a CSF2RA signal sequence. In embodiments, comprise a CSF2RA signal sequence has the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) to MLLLVTSLLLCELPHPAFLLIP (SEQ ID NO: 66) SEQ ID MEWTWVFLFLLSVTAGVHS (SEQ ID NO: 67), or MALPVTALLLPLALLLHAARP (SEQ ID NO: 68).

The polynucleotide and polypeptide sequences of signaling domains provided herein are known. In some embodiments, the polynucleotide encoding a signaling domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known nucleotide sequence. In some embodiments, the polypeptide sequence of a signaling domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

Components of a CAR may be exchanged or "swapped" using routine techniques of biotechnology for equivalent components. To provide just a few non-limiting and partial examples, a CAR of the present disclosure may comprise a binding motif as provided herein in combination with a hinge provided herein and a costimulatory domain provided herein. In certain examples, a CAR of the present disclosure may comprise a leader sequence together with a binding motif as provided herein in combination with a hinge provided herein and s costimulatory domain provided herein.

Various CAR sequences, components, and/or frameworks are known, comprising without limitation sequences of hinges, spacers, transmembrane domains, costimulatory domains, stimulatory domains, binding motifs, and variants of each, and a CAR with desired binding and components or architecture can be readily constructed if, e.g., a heavy chain variable domain sequence or CDR sequences and a light chain variable domain sequence or CDR sequences are provided.

"Polypeptide," "polypeptide fragment," "peptide" and "protein" are, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. In various embodiments, the polypeptides contemplated herein comprise a signal (or leader) sequence at the N-terminal end of the protein, which co-translationally or post-translationally directs transfer of the protein.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in some embodiments, it may be desirable to improve the binding affinity and/or other biological properties of the engineered membrane bound IL-15-IL-15Rα sushi domain chimeric receptor and CARs and TCRs by introducing one or more substitutions, deletions, additions and/or insertions. Preferably, polypeptides of the disclosure include polypeptides having at least about 50%, 60%, 65%, 70%, 75%, 85%, 90%, 95%, 98%, or 99% amino acid identity thereto. Polypeptides of the disclosure include variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. Polypeptides include "polypeptide fragments." Polypeptide fragments refer to a polypeptide, which may be monomeric or multi-meric that has an amino-terminal deletion, a carboxyl-terminal deletion, and/or an internal deletion or substitution of a naturally-occurring or recombinantly-produced polypeptide. In certain embodiments, a polypeptide fragment may comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long.

The polypeptide may also be fused in-frame or conjugated to a linker or other sequence for ease of synthesis, purification or identification of the polypeptide (e.g., poly-His), or to enhance binding of the polypeptide to a solid support. As noted above, polypeptides of the present disclosure may be altered in various ways including amino acid substitutions, deletions, truncations, and insertions. Methods for such manipulations are generally known in the art. For example, amino acid sequence variants of a reference polypeptide may be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present disclosure and still obtain a functional molecule that encodes a variant or derivative polypeptide with desirable characteristics.

Polypeptide variants further include glycosylated forms, aggregative conjugates with other molecules, and covalent conjugates with unrelated chemical moieties (e.g., pegylated molecules). Covalent variants may be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Where expression of two or more polypeptides is desired, the polynucleotide sequences encoding them may be separated by an IRES sequence. In another embodiment, two or more polypeptides may be expressed as a fusion protein that comprises one or more self-cleaving polypeptide sequences, such as a T2A polypeptide. In other embodiments, they are expressed from different promotors and can be in two or more vectors. In some embodiments, an anti-CD19 CAR is encoded in the same vector as an engineered membrane bound IL-15-IL-15Rα sushi domain chimeric receptor and is operably linked to the same promotor as the engineered membrane bound IL-15-IL-15Rα sushi domain chimeric receptor where the sequences are separated by an IRES sequence. In some embodiments, anti-CD19 CAR or TCR is encoded in the same vector as an engineered membrane bound IL-15-IL-15Rα sushi domain chimeric receptor is operably linked to a different promotor than the promotor the engineered membrane bound IL-15-IL-15Rα sushi domain chimeric receptor. In certain embodiments, an anti-CD19 and/or anti-CD20 CAR or TCR is expressed on a cell that has also been engineered to express an engineered membrane bound IL-15-IL-15Rα sushi domain chimeric receptor. In some embodiments, an anti-CD19 and/or anti-CD20 CAR or TCR is encoded in the same vector as an engineered membrane bound IL-15-IL-15Rα sushi domain chimeric receptor and is operably linked to the same promotor as the an engineered membrane bound IL-15-IL-15Rα sushi domain chimeric receptor where the sequences are separated by an IRES sequence or a cleavable linker. In some embodiments, an anti-CD19 and/or anti-CD20 CAR CAR or TCR is encoded in the same vector as an engineered membrane bound IL-15-IL-15Rα sushi domain chimeric receptor is operably linked to a different promotor than the promotor the an engineered membrane bound IL-15-IL-15Rα sushi domain chimeric receptor. In some embodiments, an anti-CD19 and/or anti-CD20 CAR binding CAR is encoded in a different vector as an engineered membrane bound IL-15-IL-15Rα sushi domain chimeric receptor.

An anti-CD19 CAR may comprise antigen-binding sequences as found in an antibody described herein (see e.g. Table 5). In some embodiments, an anti-CD19 CAR of the present disclosure comprises an antigen binding fragment provided herein.

In various embodiments, an anti-CD19 CAR comprises at least one HCDR disclosed in Table 5. In various embodiments, an anti-CD19 CAR comprises at least two HCDRs disclosed in Table 5. In various embodiments, an anti-CD19 CAR comprises three HCDRs disclosed in Table 5.

In various embodiments, an anti-CD19 binding motif comprises at least one LCDR disclosed in Table 5. In various embodiments, an anti-CD19 CAR comprises at least two LCDRs disclosed in Table 5. In various embodiments, an anti-CD19 CAR comprises three LCDRs disclosed in Table 5.

In various embodiments, an anti-CD19 CAR comprises at least one HCDR disclosed in Table 5, and at least one LCDR disclosed in Table 5. In various embodiments, an anti-CD19 binding motif comprises at least two HCDRs disclosed in Table 5, and at least two LCDRs disclosed in Table 5. In various embodiments, an anti-CD19 binding motif comprises three HCDRs disclosed in Table 5, and three LCDRs disclosed in Table 5.

In various embodiments, an anti-CD19 binding motif comprises at least one heavy chain framework region (heavy chain FR) of a heavy chain variable domain disclosed in Table 5. In various embodiments, an anti-CD19 binding motif comprises at least two heavy chain FRs of a heavy chain variable domain disclosed in Table 5. In various embodiments, an anti-CD19 binding motif comprises three heavy chain FRs of a heavy chain variable domain disclosed in Table 5.

In various embodiments, an anti-CD19 binding motif comprises at least one light chain FR of a light chain variable domain disclosed in Table 5. In various embodiments, an anti-CD19 binding motif comprises at least two light chain FRs of a light chain variable domain disclosed in Table 5. In various embodiments, an anti-CD19 binding motif comprises three light chain FRs of a light chain variable domain disclosed in Table 5.

In various embodiments, an anti-CD19 CAR comprises at least one heavy chain FR of a heavy chain variable domain disclosed in Table 5, and at least one light chain FR of a light chain variable domain disclosed in Table 5. In various embodiments, an anti-CD19 CAR comprises at least two heavy chain FRs of a heavy chain variable domain disclosed in Table 5, and at least two light chain FRs of a light chain variable domain disclosed in Table 5. In various embodiments, an anti-CD19 CAR comprises three heavy chain FRs of a heavy chain variable domain disclosed in Table 5, and three light chain FRs of a light chain variable domain disclosed in Table 5.

In various embodiments, an anti-CD19 CAR comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a heavy chain variable domain of a heavy chain variable domain disclosed in in Table 5. In various embodiments, an anti-CD19 CAR comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a light chain variable domain of a light chain variable domain disclosed in Table 5.

In various embodiments, an anti-CD19 CAR comprises at least one heavy chain variable domain having at least 75% sequence identity to a heavy chain variable domain disclosed in Table 5 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD19 CAR comprises at least one light chain variable domain having at least 75% sequence identity to a light chain variable domain disclosed in Table 5 (e.g., at least 75%, at least 80%, at least 90%, at least 95%, or 100% identity; e.g., 85-90%, 85-95%, 85-100%, 90-95%, 90-100%, or 95-100%).

In various embodiments, an anti-CD19 CAR comprises at least one heavy chain variable domain having at least 75% sequence identity to a heavy chain variable domain disclosed in Table 5 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in Table 5 (e.g., at least 75%, at least 80%, at least 90%, at least 95%, or 100% identity; e.g., 85-90%, 85-95%, 85-100%, 90-95%, 90-100%, or 95-100%).

In certain embodiments, an anti-CD19 CAR comprises a binding motif that comprises a heavy chain variable domain of the present disclosure, a light chain variable domain of the present disclosure, and a linker having at least 75% sequence identity to SEQ ID NO: 45 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD19 CAR comprises a binding motif that comprises a heavy chain variable domain of the present disclosure, a light chain variable domain of the present disclosure, and a leader sequence having at least 75% sequence identity to SEQ ID NO: 66 (e.g., at least 75%, at least 80%, at least 90%, at least 95%, or 100% identity; e.g., 85-90%, 85-95%, 85-100%, 90-95%, 90-100%, or 95-100%).

TABLE 5

Exemplary anti-CD19 Sequences

| SEQ ID NO: | Description | Sequence |
|---|---|---|
| 69 | Heavy Chain Variable Domain | EVKLQESGPGLVAPSQSLSVTCTVSGVSLPDYGVSWIRQ<br>PPRKGLEWLGVIWGSETTYYNSALKSRLTIIKDNSKSQV<br>FLKMNSLQTDDTAIYYCAKHYYYGGSYAMDYWGQGT<br>SVTVSS |
| 70 | CDRH1 IMGT (Prot) | GVSLPDYG |
| 71 | CDRH1 Kabat (Prot) | DYGVS |
| 72 | CDRH1 Chothia (Prot) | GVSLPDY |
| 73 | CDRH2 IMGT (Prot) | IWGSETT |
| 74 | CDRH2 Kabat (Prot) | VIWGSETTYYNSALKS |
| 75 | CDRH2 Chothia (Prot) | WGSET |
| 76 | CDRH3 IMGT (Prot) | AKHYYYGGSYAMDY |
| 77 | CDRH3 Kabat (Prot) | HYYYGGSYAMDY |
| 78 | CDRH3 Chothia (Prot) | HYYYGGSYAMDY |
| 79 | Light Chain Variable Domain | DIQMTQTTSSLSASLGDRVTISCRASQDISKYLNWYQQKPDG<br>TVKLLIYHTSRLHSGVPSRFSGSGSGTDYSLTISNLEQEDIATY<br>FCQQGNTLPYTFGGGTKLEIT |
| 80 | CDRL1 IMGT (Prot) | RASQDISKYLN |
| 81 | CDRL1 Kabat (Prot) | RASQDISKYLN |
| 82 | CDRL1 Chothia (Prot) | RASQDISKYLN |
| 83 | CDRL2 IMGT (Prot) | HTSRLHS |
| 84 | CDRL2 Kabat (Prot) | HTSRLHS |
| 85 | CDRL2 Chothia (Prot) | HTSRLHS |
| 86 | CDRL3 IMGT (Prot) | QQGNTLPYT |
| 87 | CDRL3 Kabat (Prot) | QQGNTLPYT |
| 88 | CDRL3 Chothia (Prot) | QQGNTLPYT |
| 89 | binding motif (Prot) | DIQMTQTTSSLSASLGDRVTISCRASQDISKYLNWYQQKPDG<br>TVKLLIYHTSRLHSGVPSRFSGSGSGTDYSLTISNLEQEDIATY<br>FCQQGNTLPYTFGGGTKLEITGSTSGSGKPGSGEGSTKGEVK<br>LQESGPGLVAPSQSLSVTCTVSGVSLPDYGVSWIRQPPRKGLE<br>WLGVIWGSETTYYNSALKSRLTIIKDNSKSQVFLKMNSLQTD<br>DTAIYYCAKHYYYGGSYAMDYWGQGTSVTVSS |

In an embodiment an anti-CD19 CAR has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 90. DIQMTQTTSSLSASLGDRVTISCRASQDISKYLNWYQQKPDGTVKLLIYHTSRLHSGVPS RFSGSGSGTDYSLTISNLEQEDIATYFCQQGNTLPYTFGGGTKLEITGSTSGSGKPGSGEG STKGEVKLQESGPGLVAPSQSLSVTCTVSGVSLPDYGVSWIRQPPRKGLEWLGV IWGSE TTYYNSALKSRLTIIKDNSKSQVFLKMNSLQTDDTAIYYCAKHYYYGGSYAMDYWGQ GTSVTVSSAAAIEVMYPPPYLDNEKSNGTIIHVKGKHLCPSPLFPGPSKPFWVLVVVGG VLACYSLLVTVAFIIFWVRSKRSRLLHSDYMNMTPRRPGPTRKHYQPYAPPRDFAAYRS RVKFSRSADAPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR (SEQ ID NO: 90). In embodiments, anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 91)
GACATTCAGATGACCCAGACCACCAGCAGCCTGAGCGCCAGCTTAGGAGA
TAGAGTTACCATCAGCTGCAGAGCCAGCCAGGACATCAGCAAATACCTGA
ACTGGTATCAGCAGAAGCCCGACGGCACTGTGAAACTGCTTATTTACCAC
ACCTCCAGACTGCACAGCGGCGTTCCCAGCAGATTCTCTGGCAGCGGATC
TGGAACCGACTACAGCCTCACCATCTCCAACCTGGAGCAGGAGGACATCG
CCACCTACTTCTGCCAGCAGGGCAACACACTGCCCTACACCTTCGGAGGA
GGAACCAAGCTGGAGATCACCGGCTCCACCTCTGGATCCGGCAAGCCCGG
ATCTGGCGAGGGATCCACCAAGGGCGAGGTTAAGCTGCAGGAGAGCGGCC
CTGGCCTGGTGGCTCCTAGCCAATCTTTATCTGTGACCTGCACTGTGTCC
GGCGTTAGCCTGCCCGATTATGGCGTTTCCTGGATCAGACAGCCCCCCAG
AAAGGGCCTGGAATGGCTGGGCGTTATCTGGGGCAGCGAGACCACATACT
ACAACAGCGCCCTGAAGAGCAGACTTACGATTATCAAGGACAACAGCAAG
AGCCAGGTTTTCCTGAAGATGAACAGCCTGCAGACCGACGACACCGCCAT
CTACTACTGCGCTAAGCACTACTACTACGGCGGCAGCTACGCCATGGACT
ACTGGGGCCAGGGAACAAGCGTTACCGTTAGCAGCGCTGCTGCAATTGAA
GTTATGTATCCTCCTCCTTACCTGGACAACGAGAAGAGCAACGGCACCAT
CATCCACGTTAAGGGCAAGCACCTGTGCCCCAGCCCTCTGTTCCCTGGAC
CTTCTAAGCCTTTCTGGGTTCTGGTGGTGGTCGGCGGCGTTTTAGCCTGT
TACAGCCTTCTGGTGACTGTGGCCTTCATCATCTTTTGGGTTAGAAGCAA
GAGAAGCAGACTGCTCCACAGCGACTACATGAACATGACCCCCAGACGGC
CTGGCCCCACCAGAAAGCATTACCAGCCCTACGCTCCTCCCAGAGACTTC
GCCGCCTACAGGAGCAGAGTTAAATTCAGCAGATCCGCCGATGCCCCCGC
TTACCAACAGGGACAAAACCAGCTGTACAATGAGCTCAACCTGGGGAGAA
GAGAAGAATACGACGTTCTGGATAAGAGAAGGGGCAGAGATCCCGAAATG
GGGGGCAAGCCCAGACGCAAGAACCCTCAGGAGGGGCTTTACAACGAACT
GCAGAAGGATAAGATGGCTGAGGCTTACTCGGAGATTGGGATGAAGGGGG
AGAGAAGGCGGGGCAAGGGACACGATGGCTTATACCAGGGGCTGAGCACC
GCCACCAAGGACACATACGACGCTCTTCATATGCAGGCTCTGCCCCCAAG
A.

In an embodiment an anti-CD19 CAR linked to a membrane bound IL-15-IL-15Rα sushi domain chimeric receptor has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 92. DIQMTQTTSSLSASLGDRVTISCRASQDISKYLNWYQQKPDGTVKLLIYHTSRLHSGVPS RFSGSGSGTDYSLTISNLEQEDIATYFCQQGNTLPYTFGGGTKLEITGSTSGSGKPGSGEG STKGEVKLQESGPGLVAPSQSLSVTCTVSGVSLPDYGVSWIRQPPRKGLEWLGV IWGSE TTYYNSALKSRLTIIKDNSKSQVFLKMNSLQTDDTAIYYCAKHYYYGGSYAMDYWGQ GTSVTVSSAAAIEVMYPPPYLDNEKSNGTIIHVKGKHLCPSPLF PGPSKPFWVLVVVGG VLACYSLLVTVAFIIFWVRSKRSRLLHSDYMNMTPRRPGPTRKHYQPYAPPRDFAAYRS RVKFSRSADAPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPRGS GEGRGSLLTCGDVEENPGPMDWTWILFLVAAATRVHSEQKLISEEDLAGSNWVNVISD LKKIEDLIQSMHIDATLYTESDVHPSCKVTAMKCFLLELQVISLESGDASIHDTVENLIIL ANNSLSSNGNVTESGCKECEELEEKNIKEFLQSFVHIVQMFINTSSGGGSGGGGSGGGGS GGGGSGGGSITCPPPMSVEHADIWVKSYSLYSRERYICNSGFKRKAGTSSLTECVLNKA TNVAHWTTPSLKCIRDGGGGSGGGGSRSNLGWLCLLLLPIPLIVWVKRKEVQKT (SEQ ID NO: 92). In embodiments, anti-CD19 CAR linked to a membrane bound IL-15-IL-15Rα sushi domain chimeric receptor is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 93)
GACATCCAGATGACACAGACTACATCCTCCCTGTCTGCCTCTCTGGGAGA
CAGAGTCACCATCAGTTGCAGGGCAAGTCAGGACATTAGTAAATATTTAA
ATTGGTATCAGCAGAAACCAGATGGAACTGTTAAACTCCTGATCTACCAT
ACATCAAGATTACACTCAGGAGTCCCATCAAGGTTCAGTGGCAGTGGGTC
TGGAACAGATTATTCTCTCACCATTAGCAACCTGGAGCAAGAAGATATTG
CCACTTACTTTTGCCAACAGGGTAATACGCTTCCGTACACGTTCGGAGGG
GGGACTAAGTTGGAAATAACAGGCTCCACCTCTGGATCCGGCAAGCCCGG
ATCTGGCGAGGGATCCACCAAGGGCGAGGTGAAACTGCAGGAGTCAGGAC
CTGGCCTGGTGGCGCCCTCACAGAGCCTGTCCGTCACATGCACTGTCTCA
GGGGTCTCATTACCCGACTATGGTGTAAGCTGGATTCGCCAGCCTCCACG
AAAGGGTCTGGAGTGGCTGGGAGTAATATGGGGTAGTGAAACCACATACT
ATAATTCAGCTCTCAAATCCAGACTGACCATCATCAAGGACAACTCCAAG
AGCCAAGTTTTCTTAAAAATGAACAGTCTGCAAACTGATGACACAGCCAT
TTACTACTGTGCCAAACATTATTACTACGGTGGTAGCTATGCTATGGACT
ACTGGGGTCAAGGAACCTCAGTCACAGTCTCCTCAGCGGCCGCAATTGAA
GTTATGTATCCTCCTCCTTACCTAGACAATGAGAAGAGCAATGGAACCAT
TATCCATGTGAAAGGGAAACACCTTTGTCCAAGTCCCCTATTTCCCGGAC
CTTCTAAGCCCTTTTGGGTGCTGGTGGTGGTTGGGGGAGTCCTGGCTTGC
TATAGCTTGCTAGTAACAGTGGCCTTTATTATTTTCTGGGTGAGGAGTAA
GAGGAGCAGGCTCCTGCACAGTGACTACATGAACATGACTCCCCGCCGCC
CCGGGCCCACCCGCAAGCATTACCAGCCCTATGCCCCACCACGCGACTTC
GCAGCCTATCGCTCCAGAGTGAAGTTCAGCAGGAGCGCAGACGCCCCCGC
GTACCAGCAGGGCCAGAACCAGCTCTATAACGAGCTCAATCTAGGACGAA
GAGAGGAGTACGATGTTTTGGACAAGAGGCGTGGCCGGGACCCTGAGATG
GGGGGAAAGCCGAGAAGGAAGAACCCTCAGGAAGGCCTGTACAATGAACT

-continued

GCAGAAAGATAAGATGGCGGAGGCCTACAGTGAGATTGGGATGAAAGGCG
AGCGCCGGAGGGGCAAGGGGCACGATGGCCTTTACCAGGGTCTCAGTACA
GCCACCAAGGACACCTACGACGCCCTTCACATGCAGGCCCTGCCCCCTCG
CGGCTCTGGCGAAGGCAGAGGCTCTCTGCTGACCTGCGGCGACGTGGAAG
AGAACCCAGGCCCCATGGACTGGACATGGATTCTGTTTCTTGTGGCTGCC
GCCACAAGAGTGCACAGCGAGCAGAAGCTGATCAGCGAGGAAGACCTCGC
TGGAAGCAATTGGGTGAACGTGATCTCCGACCTCAAAAAGATCGAGGATC
TGATCCAGTCCATGCACATCGATGCCACACTCTACACCGAGTCCGATGTG
CACCCTAGCTGCAAAGTTACAGCAATGAAATGCTTTCTGCTGGAGTTGCA
AGTAATCTCCCTGGAGTCCGGAGATGCTTCCATCCACGACACAGTGGAGA
ATTTAATCATTCTGGCTAACAATTCCCTCTCGTCTAATGGCAATGTCACT
GAGAGCGGCTGTAAAGAGTGTGAAGAGCTGGAGGAGAAAAACATCAAAGA
GTTTCTGCAGAGCTTCGTCCACATCGTCCAAATGTTCATCAACACCTCGT
CCGGGGGCGGCTCCGGGGGAGGAGGATCGGGGGGAGGAGGAAGCGGAGGT
GGAGGAAGCGGTGGAGGGTCCATTACATGCCCTCCCCCCATGTCCGTGGA
ACATGCCGACATATGGGTAAAGTCCTACTCTCTGTACTCGCGGGAACGTT
ATATCTGCAACAGCGGCTTTAAGAGAAAGGCCGGAACATCTTCTCTGACC
GAATGTGTGCTGAACAAGGCCACAAATGTGGCTCACTGGACCACGCCTAG
CCTCAAGTGTATTAGGGACGGCGGCGGAGGTTCCGGTGGCGGGGGCTCTA
GATCGAATCTGGGCTGGCTGTGTCTGCTGCTGCTCCCCATCCCTCTGATT
GTGTGGGTTAAGCGAAAAGAGGTCCAGAAAACCTAA.

Exemplary anti-CD20 antibodies and fragments thereof suitable for use in the CARs, vectors, cells and methods disclosed herein can be found in International Patent Publication No. WO/2020/123691, published Jun. 18, 2020, which is specifically incorporated herein by reference in its entirety. In an embodiment an anti-CD20 CAR has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 107. QVQLVQS-GAEVKKPGASVKVSCKASGYTFKEY-GISWVRQAPGQGLEWMGWISAYSGH TYYAQKLQGRVTMTTDTSTSTAYMELRSLRSDD-TAVYYCARGPHYDDWSGFIIWFDP WGQGTLVTVSSGSTSGSGKPGSGEG-STKGDIQMTQSPSSLSASVGDRVTITCRASQSISS YLNWYQQKPGKAPKLLI-YAASSLQSGVPSRFSGSGSGTDFTLTISSLQPEDFA-TYYCQQS YRFPPTFGQGTKVEIKAAAFVPVFLPAK-PTTTPAPRPPTPAPTIASQPLSLRPEACRPAAG GAVHTRGLDFACDIYIWAPLAGTCGVLLLSLVIT-LYCNHRNRFSVVKRGRKKLLYIFKQ PFMRPVQTTQEEDGCSCRFPEEEEGGCELRVKFSRS-ADAPAYQQGQNQLYNELNLGRR EEYDVLDKRR-GRDPEMGGKPRRKNPQEGLYNELQKDKMAEAYSEI-GMKGERRRGKG HDGLYQGLSTATKDTYDALHMQALPPR (SEQ ID NO: 107). In embodiments, anti-CD20 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 108)
CAGGTTCAGCTTGTGCAGAGCGGAGCTGAAGTTAAGAAGCCTGGCGCCTC
TGTGAAGGTTAGCTGCAAGGCCAGCGGCTACACATTCAAGGAATATGGCA
TCTCCTGGGTTAGGCAGGCTCCCGGCCAAGGCTTAGAATGGATGGGCTGG
ATCTCCGCCTACTCCGGCCACACCTACTACGCCCAGAAGCTTCAGGGCAG
GGTTACCATGACCACCGACACCAGCACCTCTACCGCCTATATGGAGCTGA
GGAGCCTGAGATCGGACGACACAGCTGTGTATTACTGCGCCAGAGGCCCC
CACTACGACGACTGGTCTGGATTTATCATCTGGTTCGACCCCTGGGGGCA
GGGCACCCTGGTCACAGTTTCTTCTGGCTCCACCAGCGGAAGCGGCAAGC
CAGGCTCAGGCGAAGGATCTACAAAAGGCGACATCCAAATGACACAGAGC
CCCAGCAGCTTGAGCGCCTCCGTTGGCGACAGAGTTACAATCACCTGCAG
GGCCTCTCAGAGCATCAGCAGCTATTTGAATTGGTATCAACAGAAGCCAG
GAAAGGCCCCTAAGCTGCTCATCTACGCTGCCAGCTCGCTCCAATCTGGC
GTTCCTAGCAGATTTAGCGGCTCCGGCAGCGGCACAGACTTTACTCTTAC
CATTAGCTCCCTGCAGCCCGAGGACTTCGCTACCTACTATTGCCAGCAAA
GCTACAGATTCCCTCCCACCTTTGGCCAGGGCACAAAGGTTGAGATCAAG
GCAGCTGCTTTCGTGCCTGTGTTCCTGCCTGCTAAGCCCACCACCACTCC
TGCTCCAAGACCTCCTACCCCCGCTCCTACAATCGCCAGCCAACCTCTGA
GCCTGAGACCGGAGGCATGCAGACCTGCGGCAGGGGGAGCAGTTCACACA
AGAGGCTTGGACTTCGCTTGCGACATCTACATCTGGGCCCCTCTGGCCGG
CACATGCGGAGTTCTTCTTCTTAGCCTGGTGATCACCCTGTACTGCAACC
ACAGAAACAGATTCAGCGTTGTGAAGAGAGGCCGGAAGAAGCTGCTGTAC
ATCTTCAAGCAGCCCTTCATGAGACCTGTGCAGACCACACAGGAGGAAGA
CGGCTGCAGCTGTAGATTCCCCGAGGAAGAGGAGGGCGGCTGTGAGCTGA
GAGTTAAGTTCAGCAGGAGCGCCGACGCCCCTGCCTACCAGCAAGGACAG
AATCAACTGTACAACGAGCTGAACCTGGGCAGACGGGAGGAATACGATGT
GCTGGACAAGAGGAGAGGCAGAGACCCCGAGATGGGCGGCAAACCTAGAA
GAAAGAACCCCCAGGAGGGCCTGTATAACGAGCTCCAGAAGGACAAGATG
GCCGAGGCCTACAGCGAGATCGGCATGAAGGGCGAAAGAAGAAGAGGCAA
GGGCCACGACGGCCTCTACCAGGGCTTAAGCACAGCTACAAAGGACACCT
ACGACGCCCTGCACATGCAGGCCCTGCCCCCTAGA.

The present disclosure also provides nucleic acids that encode any of the variety of membrane-bound IL-15-IL-15Rα chimeric polypeptides, or any of the CARs or TCRs, described herein. In one embodiment, a recombinant nucleic acid construct comprises a nucleic acid molecule encoding a membrane-bound IL-15-IL-15Rα chimeric polypeptides, optionally with one or more CARs or TRCs.

The present disclosure comprises vectors that comprise nucleic acids of the present disclosure and/or that encode membrane-bound IL-15-IL-15Rα chimeric polypeptides of the present disclosure optionally in combination with nucleic acids encoding any of the CARs or TCRs described herein. Any vector may be suitable for the present disclosure. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof. Suitable exemplary vectors include e.g., pGAR, pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

A recombinant expression vector may be any suitable recombinant expression vector. Suitable vectors comprise those designed for propagation and expansion or for expression or both, such as plasmids and viruses. For example, a vector may be selected from the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also may be used. Examples of plant expression vectors useful in the context of the disclosure comprise pBI01, pBI101.2, pBI101.3, pBI121 and pBIN19 (Clontech). Examples of animal expression vectors useful in the context of the disclosure comprise pcDNA, pEUK-Cl, pMAM, and pMAMneo (Clontech). In some embodiments, a bicistronic IRES vector (e.g., from Clontech) is used to comprise both a nucleic acid encoding an antigen binding system and an inducible expression construct described herein.

Recombinant expression vectors may be prepared using standard recombinant DNA techniques described in, for example, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Constructs of expression vectors, which are circular or linear, may be prepared to contain a replication system functional in a prokaryotic or eukaryotic host cell. Replication systems may be derived, e.g., from ColEl, 2μ plasmid, λ, SV40, bovine papilloma virus, and the like.

A recombinant expression vector may comprise one or more marker genes, which allow for selection of transformed or transfected hosts. Marker genes comprise biocide resistance, e.g., resistance to antibiotics, heavy metals, etc., complementation in an auxotrophic host to provide prototrophy, and the like. Suitable marker genes for the recombinant expression vectors comprise, for instance, neomycin/G418 resistance genes, puromycin resistance genes, hygromycin resistance genes, histidinol resistance genes, tetracycline resistance genes, and ampicillin resistance genes.

Vectors useful in the context of the disclosure may be "naked" nucleic acid vectors (i.e., vectors having little or no proteins, sugars, and/or lipids encapsulating them), or vectors complexed with other molecules. Other molecules that may be suitably combined with the vectors comprise without limitation viral coats, cationic lipids, liposomes, polyamines, gold particles, and targeting moieties such as ligands, receptors, or antibodies that target cellular molecules.

In certain embodiments, a membrane-bound IL-15-IL-15Rα chimeric polypeptide and a CAR or TCR can be constructed in a single, multicistronic expression cassette, in multiple expression cassettes of a single vector, or in multiple vectors. In one embodiment, the disclosure provides sets of vectors that include a first vector that includes a sequence that encodes any of the a membrane-bound IL-15-IL-15Rα chimeric polypeptides described herein, and a second vector that includes a sequence that encodes a CAR or TCR. In some embodiments, one or both of the first vector and the second vector is a lentiviral, retroviral or an adenoviral vector. In some embodiments, the second vector further includes a promoter sequence and/or an enhancer sequence that is operably linked to the sequence encoding the CAR or TCR. In some embodiments, the second vector further includes a poly(A) sequence operably linked to the sequence encoding the CAR or TCR. In one embodiment, the disclosure provides a polycistronic expression cassette. Examples of elements which create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-KB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller et al., 1985, Mol. Cell. Biol. 5:431-437); PA317 (Miller et al., 1986, Mol. Cell. Biol. 6:2895-2902); and CRIP (Danos et al., 1988, Proc. Natl. Acad. Sci. USA 85:6460-6464). Non-amphotropic particles are suitable too, e.g., particles pseudotyped with VSVG, RD114 or GALV envelope and any other known in the art.

Vector DNA may be introduced into a cell, e.g., an immune cell, via conventional transformation, transfection, or transduction techniques. The terms "transformation" and "transfection" encompass a variety of art-recognized techniques for introducing foreign nucleic acid (e.g., DNA) into a cell, such as calcium phosphate or calcium chloride co-precipitation, DEAE-dextran-mediated transfection, lipofection, gene gun, nanoparticle-mediated delivery, or electroporation. Transduction comprises viral delivery of a vector to a cell, e.g., by a vector disclosed herein, comprising without limitation retrovirus, lentivirus, and AAV.

The present disclosure comprises cells that comprise, express, or are engineered (e.g., transformed or transduced) to comprise or express, at least one vector or nucleic acid of the present disclosure. In one embodiment, the present disclosure provides cells (1) comprising (a) a CAR or TCR, and (b) a membrane-bound IL-15-IL-15Rα chimeric polypeptide. The immune cells can be transduced with a CAR or TCR and a membrane-bound IL-15-IL-15Rα chimeric polypeptide such that the cells express the CAR or TCR and a membrane-bound IL-15-IL-15Rα chimeric polypeptide.

Chimeric antigen receptors (CARs or CAR-Ts) and engineered T cell receptors (TCRs) may be readily inserted into and expressed by immune cells, e.g., T cells. In certain embodiments, cells (e.g., immune cells such as T cells, NK cells or induced pluripotent stem cells (iPSCs)) are obtained from a donor subject. In some embodiments, the donor subject is human patient afflicted with a cancer or a tumor. In other embodiments, the donor subject is a human patient not afflicted with a cancer or a tumor. In some embodiments, an engineered cell is autologous to a subject. In some embodiments, an engineered cell is allogeneic to a subject.

In certain embodiments, the presently disclosed immune cells (e.g., have increased secretion of anti-tumor cytokines, including, but not limited to, IL-18, IL-2, IFN-γ, and TNF-α. In certain embodiments, the immune cells have decreased secretion of cytokines associated with cytokine release syndrome (CRS), e.g., IL-6.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, an iPSC cell, or any combination thereof.

In one embodiment, a membrane-bound IL-15-IL-15Rα chimeric polypeptide and/or a CAR or TCR as provided herein is introduced into T cells. The T cells may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction and placed in an appropriate buffer or media for subsequent processing. In some embodiments, the cells are washed with PBS. As will be appreciated, a washing step may be used, such as by using a semiautomated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Publication No. 2013/0287748, and International Patent Application Publication Nos. WO2015/120096 and WO2017/070395, all of which are herein incorporated by reference in their totality for the purposes of describing these methods and in their entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion. In some embodiments, CD8+ cells are further sorted into naive, central memory, and effector cells by identifying cell surface antigens that are associated with each of these types of CD8+ cells. In some embodiments, the expression of phenotypic markers of central memory T cells includes CCR7, CD3, CD28, CD45RO, CD62L, and CD127 and are negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+ T helper cells may be sorted into naive, central memory, and effector cells by identifying cell populations that have cell surface antigens.

In some embodiments, the immune cells, e.g., NK cells or T cells, are genetically modified following isolation using known methods, or the immune cells are activated and expanded (or differentiated in the case of progenitors) in vitro prior to being genetically modified. In another embodiment, the immune cells, e.g., NK cell or T cells, are genetically modified with a CAR or TCR as described herein (e.g., transduced with a viral vector comprising one or more nucleotide sequences encoding a CAR or TCR), optionally genetically modified with a membrane-bound IL-15-IL-15Rα chimeric polypeptide (e.g., transduced with a viral vector comprising one or more nucleotide sequences encoding a membrane-bound IL-15-IL-15Rα chimeric polypeptide), and then are activated and/or expanded in vitro. Methods for activating and expanding T cells are known in the art and are described, e.g., in U.S. Pat. Nos. 6,905,874; 6,867,041; and 6,797,514; and International Patent Application Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S.

Pat. Nos. 6,040,177 and 5,827,642 and International Patent Application Publication No. WO 2012/129514, the contents of which are hereby incorporated by reference in their entirety.

The methods described herein can further comprise enriching a population of lymphocytes obtained from a donor. Enrichment of a population of lymphocytes, e.g., the one or more T cells, can be accomplished by any suitable separation method including, but not limited to, the use of a separation medium (e.g., FICOLL-PAQUE™, ROSETTESEP™ HLA Total Lymphocyte enrichment cocktail, Lymphocyte Separation Medium (LSA) (MP Biomedical Cat. No. 0850494X), or the like), cell size, shape or density separation by filtration or elutriation, mmunomagnetic separation (e.g., magnetic activated cell sorting system, MACS), fluorescent separation (e.g., fluorescence activated cell sorting system, FACS), or bead based column separation.

The methods described herein can further comprise stimulating the population of lymphocytes with one or more T-cell stimulating agents to produce a population of activated T cells under a suitable condition. Any combination of one or more suitable T cell stimulating agents can be used to produce a population of activated T cells including, including, but not limited to, an antibody or functional fragment thereof which targets a T-cell stimulatory or co-stimulatory molecule (e.g., anti-CD2 antibody, anti-CD3 antibody, anti-CD28 antibody, or a functional fragment thereof), or any other suitable mitogen (e.g., tetradecanoyl phorbol acetate (TPA), phytohaemagglutinin (PHA), concanavalin A (conA), lipopolysaccharide (LPS), pokeweed mitogen (PWM)), or a natural ligand to a T-cell stimulatory or co-stimulatory molecule.

Suitable conditions for stimulating the population of lymphocytes as described herein can include a temperature, for an amount of time, and/or in the presence of a level of $CO_2$. In certain embodiments, the temperature for stimulation is about 34° C., about 35° C., about 36° C., about 37° C., or about 38° C. In certain embodiments, the temperature for stimulation is about 34-38° C. In certain embodiments, the temperature for stimulation is from about 35-37° C. In certain embodiments, the temperature for stimulation is from about 36-38° C. In certain embodiments, the temperature for stimulation is about 36-37° C. or about 37° C.

Another condition for stimulating the population of lymphocytes as described herein can include a time for stimulation. In some embodiments, the time for stimulation is about 24-72 hours. In some embodiments, the time for stimulation is about 24-36 hours, about 30-42 hours, about 36-48 hours, about 40-52 hours, about 42-54 hours, about 44-56 hours, about 46-58 hours, about 48-60 hours, about 54-66 hours, or about 60-72 hours. In one particular embodiment, the time for stimulation is about 48 hours or at least about 48 hours. In other embodiments, the time for stimulation is about 44-52 hours. In certain embodiments, the time for stimulation is about 40-44 hours, about 40-48 hours, about 40-52 hours, or about 40-56 hours.

Other conditions for stimulating the population of lymphocytes as described herein can include a $CO_2$ level. In some embodiments, the level of $CO_2$ for stimulation is about 1.0-10% $CO_2$. In some embodiments, the level of $CO_2$ for stimulation is about 1.0%, about 2.0%, about 3.0%, about 4.0%, about 5.0%, about 6.0%, about 7.0%, about 8.0%, about 9.0%, or about 10.0% $CO_2$. In one embodiment, the level of $CO_2$ for stimulation is about 3-7% $CO_2$. In other embodiments, the level of $CO_2$ for stimulation is about 4-6% $CO_2$. In still other embodiments, the level of $CO_2$ for stimulation is about 4.5-5.5% $CO_2$. In one particular embodiment, the level of $CO_2$ for stimulation is about 5% $CO_2$.

The conditions for stimulating the population of lymphocytes can comprise a temperature, for an amount of time for stimulation, and/or in the presence of a level of $CO_2$ in any combination. For example, the step of stimulating the population of lymphocytes can comprise stimulating the population of lymphocytes with one or more T-cell stimulating agents at a temperature of about 36-38° C., for an amount of time of about 44-52 hours, and in the presence of a level of $CO_2$ of about 4.5-5.5% $CO_2$.

The concentration of lymphocytes useful for the methods herein is about $1.0\text{-}10.0\times10^6$ cells/mL. In certain embodiments, the concentration of lymphocytes is about $1.0\text{-}2.0\times10^6$ cells/mL, about $1.0\text{-}3.0\times10^6$ cells/mL, about $1.0\text{-}4.0\times10^6$ cells/mL, about $1.0\text{-}5.0\times10^6$ cells/mL, about $1.0\text{-}6.0\times10^6$ cells/mL, about $1.0\text{-}7.0\times10^6$ cells/mL, about $1.0\text{-}8.0\times10^6$ cells/mL, $1.0\text{-}9.0\times10^6$ cells/mL, or about $1.0\text{-}10.0\times10^6$ cells/mL. In certain embodiments, the concentration of lymphocytes is about $1.0\text{-}2.0\times10^6$ cells/mL. In certain embodiments, the concentration of lymphocytes is about $1.0\text{-}1.2\times10^6$ cells/mL, about $1.0\text{-}1.4\times10^6$ cells/mL, about $1.0\text{-}1.6\times10^6$ cells/mL, about $1.0\text{-}1.8\times10^6$ cells/mL, or about $1.0\text{-}2.0\times10^6$ cells/mL. In certain embodiments, the concentration of lymphocytes is at least about $1.0\times10^6$ cells/mL, at least about $1.1\times10^6$ cells/mL, at least about $1.2\times10^6$ cells/mL, at least about $1.3\times10^6$ cells/mL, at least about $1.4\times10^6$ cells/mL, at least about $1.5\times10^6$ cells/mL, at least about $1.6\times10^6$ cells/mL, at least about $1.7\times10^6$ cells/mL, at least about $1.8\times10^6$ cells/mL, at least about $1.9\times10^6$ cells/mL, at least about $2.0\times10^6$ cells/mL, at least about $4.0\times10^6$ cells/mL, at least about $6.0\times10^6$ cells/mL, at least about $8.0\times10^6$ cells/mL, or at least about $10.0\times10^6$ cells/mL.

An anti-CD3 antibody (or functional fragment thereof), an anti-CD28 antibody (or functional fragment thereof), or a combination of anti-CD3 and anti-CD28 antibodies can be used in accordance with the step of stimulating the population of lymphocytes. Any soluble or immobilized anti-CD2, anti-CD3 and/or anti-CD28 antibody or functional fragment thereof can be used (e.g., clone OKT3 (anti-CD3), clone 145-2C11 (anti-CD3), clone UCHT1 (anti-CD3), clone L293 (anti-CD28), clone 15E8 (anti-CD28)). In some aspects, the antibodies can be purchased commercially from vendors known in the art including, but not limited to, Miltenyi Biotec, BD Biosciences (e.g., MACS GMP CD3 pure 1 mg/mL, Part No. 170-076-116), and eBioscience, Inc. Further, one skilled in the art would understand how to produce an anti-CD3 and/or anti-CD28 antibody by standard methods. In some embodiments, the one or more T cell stimulating agents that are used in accordance with the step of stimulating the population of lymphocytes include an antibody or functional fragment thereof which targets a T-cell stimulatory or costimulatory molecule in the presence of a T cell cytokine. In one aspect, the one or more T cell stimulating agents include an anti-CD3 antibody and IL-2. In certain embodiments, the T cell stimulating agent includes an anti-CD3 antibody at a concentration of from about 20 ng/mL-100 ng/mL. In certain embodiments, the concentration of anti-CD3 antibody is about 20 ng/mL, about 30 ng/mL, about 40 ng/mL, about 50 ng/mL, about 60 ng/mL, about 70 ng/mL, about 80 ng/mL, about 90 ng/mL, or about 100 ng/mL. In one particular embodiment, the concentration of anti-CD3 antibody is about 50 ng/mL. In an alternative embodiment, T cell activation is not needed. In such embodiment, the step of stimulating the population of lymphocytes to produce a population of activated T cells is omitted from the method, and the population of lymphocytes, which can be enriched for T lymphocytes, is transduced in accordance with the steps below.

The methods described herein can comprise transducing the population of activated T cells with a viral vector comprising a nucleic acid molecule which encodes a membrane-bound IL-15-IL-15Rα chimeric polypeptide and/or a CAR or TCR, using a single cycle transduction to produce a population of transduced T cells. In embodiments, utilizing a viral vector with a membrane-bound IL-15-IL-15Rα chimeric polypeptide, the viral vector may be separate from the viral vector encoding the CAR or TCR or a viral vector may encode both the membrane-bound IL-15-IL-15Rα chimeric polypeptide and the CAR or TCR. Transducing the population of activated immune cells as described herein may be performed for a period of time, at certain temperature and/or in the presence of a specific level of $CO_2$ in any combination: a temperature of about 36-38° C., for an amount of time of about 16-24 hours, and in the presence of a level of $CO_2$ of about 4.5-5.5% $CO_2$. The immune cells may be prepared by the combination of any one of the methods of the application with any manufacturing method of preparing T cells for immunotherapy, including, without limitation, those described in International Patent Application Publication Nos. WO2015/120096 and WO2017/070395, which are herein incorporated by reference in their totality for the purposes of describing these methods; any and all methods used in the preparation of Axicabtagene ciloleucel, Brexucabtagene autoleucel, Liso-cel; any and all methods used in the preparation of Tisagenlecleucel; any and all methods used in the preparation of "off-the-shelf" T cells for immunotherapy; and any other methods of preparing lymphocytes for administration to humans. The manufacturing process may be adapted to remove circulating tumor cells from the cells obtained from the patient.

Several recombinant viruses have been used as viral vectors to deliver genetic material to a cell. Viral vectors that can be used in accordance with the transduction step can be any ecotropic or amphotropic viral vector including, but not limited to, recombinant retroviral vectors, recombinant lentiviral vectors, recombinant adenoviral vectors, and recombinant adeno-associated viral (AAV) vectors. In some embodiments, the method further comprises transducing the one or more NK cells or T cells with a retrovirus. In one embodiment, the viral vector used to transduce the population of NK cells or activated T cells is an MSGV1 gamma retroviral vector. In certain embodiments, the viral vector used to transduce the population of NK cells or activated T cells is the PG13-CD19-H3 Vector described by Kochenderfer, J. Immunother. 32(7): 689-702 (2009). According to one aspect of this embodiment, the viral vector is grown in a suspension culture in a medium which is specific for viral vector manufacturing referred to herein as a "viral vector inoculum." Any suitable growth media and/or supplements for growing viral vectors can be used in the viral vector inoculum in accordance with the methods described herein. According to some aspects, the viral vector inoculum is then be added to the serum-free culture media described below during the transduction step.

The conditions for transducing the population of NK cells or activated T cells as described herein can comprise a specific time, at a specific temperature and/or in the presence of a specific level of CO2. In certain embodiments, the temperature for transduction is about 34° C., about 35° C., about 36° C., about 37° C., or about 38° C. In one embodiment, the temperature for transduction is about 34-38° C. In another embodiment, the temperature for transduction is from about 35-37° C. In another embodiment, the temperature for transduction is from about 36-38° C. In still another embodiment, the temperature for transduction is about 36-37° C. In one embodiment, the temperature for transduction is about 37° C.

In certain embodiments, the time for transduction is about 12-36 hours. In some embodiments, the time for transduction is about 12-16 hours, about 12-20 hours, about 12-24 hours, about 12-28 hours, or about 12-32 hours. In other embodiments, the time for transduction is about 20 hours or at least about 20 hours. In one embodiment, the time for transduction is about 16-24 hours. In other embodiments, the time for transduction is at least about 14 hours, at least about 16 hours, at least about 18 hours, at least about 20 hours, at least about 22 hours, at least about 24 hours, or at least about 26 hours.

In certain embodiments, the level of $CO_2$ for transduction is about 1.0-10% $CO_2$. In other embodiments, the level of $CO_2$ for transduction is about 1.0%, about 2.0%, about 3.0%, about 4.0%, about 5.0%, about 6.0%, about 7.0%, about 8.0%, about 9.0%, or about 10.0% $CO_2$. In one embodiment, the level of $CO_2$ for transduction is about 3-7% $CO_2$. In another embodiment, the level of $CO_2$ for transduction can be about 4-6% $CO_2$. In another embodiment, the level of $CO_2$ for transduction is about 4.5-5.5% $CO_2$. In one embodiment, the level of $CO_2$ for transduction is about 5% $CO_2$.

In some embodiments, transducing the population of activated T cells as described herein can be performed for a particular time, at a specific temperature and/or in the presence of a specific level of $CO_2$ in any combination: a temperature of about 36-38° C., for an amount of time of about 16-24 hours, and in the presence of a level of $CO_2$ of about 4.5-5.5% $CO_2$.

The methods described herein can comprise expanding the population of transduced one or more NK cells or T cells for a particular time to produce a population of engineered NK cells or T cells. The predetermined time for expansion can be any suitable time which allows for the production of (i) a sufficient number of cells in the population of engineered NK cells or T cells for at least one dose for administering to a patient, (ii) a population of engineered T cells with a favorable proportion of juvenile cells compared to a typical longer process, or (iii) both (i) and (ii). This time will depend on the cell surface receptor expressed by the NK cells or T cells, the vector used, the dose that is needed to have a therapeutic effect, and other variables. Thus, in some embodiments, the predetermined time for expansion can be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or more than 21 days. In some aspects, the time for expansion is shorter than expansion methods known in the art. For example, the predetermined time for expansion can be shorter by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or can be shorter by more than 75%. In one aspect, the time for expansion is about 3 days, and the time from enrichment of the population of lymphocytes to producing the engineered NK cells or T cells is about 6 days.

The conditions for expanding the population of transduced NK cells or T cells can include a temperature and/or in the presence of a level of $CO_2$. In certain embodiments, the temperature is about 34° C., about 35° C., about 36° C., about 37° C., or about 38° C. In one embodiment, the temperature is about 34-38° C. In another embodiment, the temperature is from about 35-37° C. In another embodiment, the temperature is from about 36-38° C. In yet another embodiment, the temperature is about 36-37° C. In one embodiment, the temperature is about 37° C. In certain embodiments, the level of $CO_2$ is 1.0-10% $CO_2$. In other embodiments, the level of $CO_2$ is about 1.0%, about 2.0%, about 3.0%, about 4.0%, about 5.0%, about 6.0%, about 7.0%, about 8.0%, about 9.0%, or about 10.0% $CO_2$. In one embodiment, the level of $CO_2$ is about 4.5-5.5% CO2. In another embodiment, the level of $CO_2$ is about 5% $CO_2$. In other embodiments, the level of CO2 is about 3.5%, about 4.0%, about 4.5%, about 5.0%, about 5.5%, or about 6.5% $CO_2$. In some embodiments, the conditions for expanding the population of transduced NK cells or T cells include a temperature and/or in the presence of a level of $CO_2$ in any combination. For example, conditions for expanding the population of transduced T cells comprise a temperature of about 36-38° C. and in the presence of a level of $CO_2$ of about 4.5-5.5% $CO_2$.

Each step of the manufacturing described herein can be performed in a closed system. In certain embodiments, the closed system is a closed bag culture system, using any suitable cell culture bags (e.g., Miltenyi Biotec MACS® GMP Cell Differentiation Bags, Origen Biomedical PermaLife Cell Culture bags). In some embodiments, the cell culture bags used in the closed bag culture system are coated with a recombinant human fibronectin fragment during the transduction step. The recombinant human fibronectin fragment can include three functional domains: a central cell-binding domain, heparin-binding domain IL, and a CS1-sequence. The recombinant human fibronectin fragment can be used to increase gene efficiency of retroviral transduction of immune cells by aiding colocalization of target cells and viral vector. In certain embodiments, the recombinant human fibronectin fragment is RETRONECTIN® (Takara Bio, Japan). In certain embodiments, the cell culture bags are coated with recombinant human fibronectin fragment at a concentration of about 1-60 μg/mL or about 1-40 μg/mL. In other embodiments, the cell culture bags are coated with recombinant human fibronectin fragment at a concentration of about 1-20 μg/mL, 20-40 μg/mL, or 40-60 μg/mL. In some embodiments, the cell culture bags are coated with about 1 μg/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 11 μg/mL, about 12 μg/mL, about 13 μg/mL, about 14 μg/mL, about 15 μg/mL, about 16 μg/mL, about 17 μg/mL, about 18 μg/mL, about 19 μg/mL, or about 20 μg/mL recombinant human fibronectin fragment. In other embodiments, the cell culture bags are coated with about 2-5 μg/mL, about 2-10 μg/mL, about 2-20 μg/mL, about 2-25 μg/mL, about 2-30 μg/mL, about 2-35 μg/mL, about 2-40 μg/mL, about 2-50 μg/mL, or about 2-60 μg/mL recombinant human fibronectin fragment. In certain embodiments, the cell culture bags are coated with at least about 2 μg/mL, at least about 5 μg/mL, at least about 10 μg/mL, at least about 15 μg/mL, at least about 20 μg/mL, at least about 25 μg/mL, at least about 30 μg/mL, at least about 40 μg/mL, at least about 50 μg/mL, or at least about 60 μg/mL recombinant human fibronectin fragment. In one particular embodiment, the cell culture bags are coated with at least about 10 μg/mL recombinant human fibronectin fragment. The cell culture bags used in the closed bag culture system can optionally be blocked with human albumin serum (HSA) during the transduction step. In an alternative embodiment, the cell culture bags are not blocked with HSA during the transduction step.

The population of engineered immune cells produced by the methods described above may optionally be cryopreserved so that the cells may be used later. A method for cryopreservation of a population of engineered immune cells also is provided herein. Such a method may include a step of washing and concentrating the population of engineered immune cells with a diluent solution. For example, the diluent solution is normal saline, 0.9% saline, PlasmaLyte A (PL), 5% dextrose/0.45% NaCl saline solution (D5), human serum albumin (HSA), or a combination thereof. Also, HSA may be added to the washed and concentrated cells for improved cell viability and cell recovery after thawing. In another aspect, the washing solution is normal saline and washed and concentrated cells are supplemented with HSA (5%). The method may also include a step of generating a cryopreservation mixture, wherein the cryopreservation mixture includes the diluted population of cells in the diluent solution and a suitable cryopreservative solution. The cryopreservative solution may be any suitable cryopreservative solution including, but not limited to, CryoStor10 (BioLife Solution), mixed with the diluent solution of engineered immune cells at a ratio of 1:1 or 2:1. HSA may be added to provide a final concentration of about 1.0-10%, about 1.0%, about 2.0%, about 3.0%, about 4.0%, about 5.0%, about 6.0%, about 7.0%, about 8.0%, about 9.0%, about 10.0%, about 1-3% HSA, about 1-4% HSA, about 1-5% HSA, about 1-7% HSA, about 2-4% HSA, about 2-5% HSA, about 2-6% HSA, about 2-7% HSA or about 2.5% HSA in the cryopreserved mixture. Cryopreservation of a population of engineered immune cells may comprise washing cells with 0.9% normal saline, adding HSA at a final concentration of 5% to the washed cells, and diluting the cells 1:1 with CryoStor™ CS10 (for a final concentration of 2.5% HSA in the final cryopreservation mixture). In some aspect, the method also includes a step of freezing the cryopreservation mixture. Also, the cryopreservation mixture is frozen in a controlled rate freezer using a defined freeze cycle at a cell concentration of between about $1\times10^6$ to about $1.5\times10^7$ cells/mL of cryopreservation mixture. The method may also include a step of storing the cryopreservation mixture in vapor phase liquid nitrogen.

The population of engineered immune cells produced by the methods described herein may be cryopreserved at a predetermined dose. The predetermined dose may be a therapeutically effective dose, which may be any therapeutically effective dose as provided below. The predetermined dose of engineered immune cells may depend on the binding motif that is expressed by the immune cells (e.g., the affinity and density of the binding motif expressed on the cell), the type of target cell, the nature of the disease or pathological condition being treated, or a combination of both. The binding motif that is expressed by the engineered immune cells may be any antigen or molecule to be targeted by a CAR or TCR. In certain aspects, the predetermined dose of engineered immune cells expressing a CAR or a TCR may be more than about 1 million to less than about 3 million transduced engineered NK cells or T cells/kg. In one embodiment, the predetermined dose of engineered NK cells or T cells expressing a CAR or a TCR may be more than about 1 million to about 2 million transduced engineered NK cells or T cells per kilogram of body weight (cells/kg). The predetermined dose of engineered NK cells or T cells expressing a CAR or a TCR may be more than 1 million to about 2 million, at least about 2 million to less than about 3 million transduced engineered NK cells or T cells per kilogram of body weight (cells/kg). In one embodiment, the predetermined dose of engineered NK cells or T cells expressing a CAR or a TCR may be about 2 million transduced engineered T cells/kg. In another embodiment, the predetermined dose of engineered NK cells or T cells expressing a CAR or a TCR may be at least about 2 million transduced engineered NK cells or T cells/kg. Examples of the predetermined dose of engineered NK cells or T cells expressing a CAR or a TCR may be about 2.0 million, about 2.1 million, about 2.2 million, about 2.3 million, about 2.4 million, about 2.5 million, about 2.6 million, about 2.7 million, about 2.8 million, or about 2.9 million transduced engineered NK cells or T cells/kg. In one embodiment, the population of engineered T cells may be cryopreserved at a predetermined dose of about 1 million engineered NK cells or T cells per kilogram of body weight (cells/kg). In certain embodiment, the population of engineered NK cells or T cells may be cryopreserved at a predetermined dose of from about 500,000 to about 1 million engineered NK cells or T cells/kg. In certain embodiment, the population of engineered NK cells or T cells may be cryopreserved at a predetermined dose of at least about 1 million, at least about 2 million, at least about 3 million, at least about 4 million, at least about 5 million, at least about 6 million, at least about 7 million, at least about 8 million, at least about 9 million, at least about 10 million engineered NK cells or T cells/kg. In other aspects, the population of engineered NK cells or T cells may be cryopreserved at a predetermined dose of less than 1 million cells/kg, 1 million cells/kg, 2 million cells/kg, 3 million cells/kg, 4 million cells/kg, 5 million cells/kg, 6 million cells/kg, 7 million cells/kg, 8 million cells/kg, 9 million cells/kg, 10 million cells/kg, more than 10 million cells/kg, more than 20 million cells/kg, more than 30 million cells/kg, more than 40 million cells/kg, more than 50 million cells/kg, more than 60 million cells/kg, more than 70 million cells/kg, more than 80 million cells/kg, more than 90 million cells/kg, or more than 100 million cells/kg. In certain aspects, the population of engineered NK cells or T cells may be cryopreserved at a predetermined dose of from about 1 million to about 2 million engineered NK cells or T cells/kg. The population of engineered NK cells or T cells may be cryopreserved at a predetermined dose between about 1 million cells to about 2 million cells/kg, about 1 million cells to about 3 million cells/kg, about 1 million cells to about 4 million cells/kg, about 1 million cells to about 5 million cells/kg, about 1 million cells to about 6 million cells/kg, about 1 million cells to about 7 million cells/kg, about 1 million cells to about 8 million cells/kg, about 1 million cells to about 9 million cells/kg, about 1 million cells to about 10 million cells/kg. The predetermined dose of the population of engineered NK cells or T cells may be calculated based on a subject's body weight. In one example, the population of engineered NK cells or T cells may be cryopreserved in about 0.5-200 mL of cryopreservation media. Additionally, the population of engineered T cells may be cryopreserved in about 0.5 mL, about 1.0 mL, about 5.0 mL, about 10.0 mL, about 20 mL, about 30 mL, about 40 mL, about 50 mL, about 60 mL, about 70 mL, about 80 mL, about 90 mL, or about 100 mL, about 10-30 mL, about 10-50 mL, about 10-70 mL, about 10-90 mL, about 50-70 mL, about 50-90 mL, about 50-110 mL, about 50-150 mL, or about 100-200 mL of cryopreservation media. In certain aspects, the population of engineered NK cells or T cells may be cryopreserved in about 50-70 mL of cryopreservation media.

The present disclosure also provides compositions (e.g., pharmaceutical compositions) that include any of the nucleic acids, vectors, sets of nucleic acids, sets of vectors, or cells described herein. For example, provided herein is a composition that includes any of the nucleic acids or sets of nucleic acids described herein, or any of the vectors or sets of vectors provided herein, and a pharmaceutically acceptable solvent or carrier. Also provided herein are pharmaceutical compositions that include any of the variety of sets of vectors provided herein (e.g., sets of vectors that include a first vector that includes any of the nucleic acids encoding a membrane-bound IL-15-IL-15Rα chimeric polypeptide, and a second vector that includes a nucleic acid sequence encoding a CAR or TCR) and a pharmaceutically acceptable carrier. In some embodiments, the composition comprises a pharmaceutically acceptable carrier, diluent, solubilizer, emulsifier, preservative and/or adjuvant. In some embodiments, the composition comprises an excipient. In another embodiment, the composition comprises a NK cells or T cell comprising a CAR or a TCR and a membrane-bound IL-15-IL-15Rα chimeric polypeptide.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In certain embodiments, the vehicle for parenteral injection is sterile distilled water in which composition described herein, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule.

In some embodiments, a composition can be any of the cells described herein (e.g., any of the cells described herein previously obtained from a subject, e.g., a subject identified or diagnosed as having a cancer). In one embodiment, cells comprise a nucleic acid encoding a membrane-bound IL-15-IL-15Rα chimeric polypeptide and/or any of the CARs or TCRs described herein. In a composition including any of the cells described herein, the composition can further include a cell culture medium or a pharmaceutically acceptable buffer (e.g., phosphate-buffered saline).

Pharmaceutical compositions may comprise a CAR- or TCR-expressing cell, e.g., a plurality of TCR- or CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Pharmaceutical composition of the present disclosure may be formulated for administration according to any embodiment set forth herein, at least one non-limiting example of which is intravenous administration. A composition may be formulated for intravenous, intratumoral, intraarterial, intramuscular, intraperitoneal, intrathecal, epidural, and/or subcutaneous administration routes. In embodiments, the composition is formulated for a parenteral route of administration. A composition suitable for parenteral administration may be an aqueous or nonaqueous, isotonic sterile injection solution, which may contain antioxidants, buffers, bacteriostats, and solutes, for example, that render the composition isotonic with the blood of the intended recipient. An aqueous or nonaqueous sterile suspension may contain one or more suspending agents, solubilizers, thickening agents, stabilizers, and preservatives. Pharmaceutical compositions of the present disclosure may be administered in a manner appropriate to the disease to be treated (or prevented).

In various embodiments, engineered NK or T cells described herein may be incorporated into a pharmaceutical composition. As disclosed herein, a pharmaceutical composition comprising an engineered T cell may be in any form. Such forms comprise, e.g., liquid, semi-solid and solid dosage forms, such as liquid solutions (e.g., injectable and infusible solutions), dispersions or suspensions, tablets, pills, powders, liposomes and suppositories.

Pharmaceutical compositions comprising a binding agent of the present disclosure may be formulated by known methods (such as described in Remington's Pharmaceutical Sciences, 17th edition, ed. Alfonso R. Gennaro, Mack Publishing Company, Easton, Pa. (1985)). In various instances, a pharmaceutical composition comprising a binding agent of the present disclosure may be formulated to comprise a pharmaceutically acceptable carrier or excipient. Examples of pharmaceutically acceptable carriers comprise, without limitation, any and all solvents, dispersion media, coatings, antibacterial and antifungal agents, isotonic and absorption delaying agents, and the like that are physiologically compatible. Compositions comprising engineered T cells may comprise a pharmaceutically acceptable salt, e.g., an acid addition salt or a base addition salt.

The sterile composition for injection may be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Non-limiting examples of oily liquids comprise sesame oil and soybean oil, and may be combined with benzyl benzoate or benzyl alcohol as a solubilizing agent. Other items that may be comprised in a composition are a buffer such as a phosphate buffer, or sodium acetate buffer, a soothing agent such as procaine hydrochloride, a stabilizer such as benzyl alcohol or phenol, and an antioxidant. The formulated injection may be packaged in a suitable ampule.

In one embodiment, a pharmaceutical composition is substantially free of detectable levels of a contaminant, e.g., of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenzae, Neisseria meningitides, Pseudomonas aeruginosa, Staphylococcus aureus, Streptococcus pneumonia*, and/or *Streptococcus pyogenes* group A.

In some embodiments, an engineered cell is treated ex vivo with interleukin-2 (IL-2) prior to infusion into a cancer patient, and the cancer patient is treated with IL-2 after infusion. Furthermore, in some embodiments, a cancer patient may undergo preparative lymphodepletion—the temporary ablation of the immune system-prior to administration of a binding agent. A combination of IL-2 treatment and preparative lymphodepletion may enhance persistence of a binding agent. In some embodiments, an engineered cell is transduced or transfected with a nucleic acid encoding a cytokine (e.g., a membrane-bound IL-15-IL-15Rα chimeric polypeptide), which nucleic acid may be engineered to provide for constitutive, regulatable, or temporally-controlled expression of the cytokine. Suitable cytokines comprise, for example, cytokines which act to enhance the survival of T lymphocytes during the contraction phase, which may facilitate the formation and survival of memory T lymphocytes.

Dosage administered to a subject in some embodiments, may vary with the embodiment, the composition employed, the method of administration, and the site and subject being treated. However, a dose should be sufficient to provide a therapeutic response. A clinician may determine the therapeutically effective amount of a composition to be administered to a human or other subject in order to treat or prevent a medical condition. The precise amount of the composition required to be therapeutically effective may depend upon numerous factors, e.g., such as the activity of the binding agent, and the route of administration.

A suitable number of engineered cells comprising a CAR or TCR may be administered to a subject. While a single engineered cell described herein is capable of expanding and providing a therapeutic benefit, in some embodiments, $10^2$ or more, e.g., $10^3$ or more, $10^4$ or more, $10^5$ or more, or $10^8$ or more, engineered cells are administered. In some embodiments, $10^{12}$ or less, e.g., $10^{11}$ or less, $10^9$ or less, $10^7$ or less, or $10^3$ or less, engineered cells described herein are administered to a subject. In some embodiments, $10^2$-$10^5$, $10^4$-$10^7$, $10^3$-$10^9$, or $10^5$-$10^{10}$ engineered cells described herein are administered. A pharmaceutical composition comprising cells comprising a CAR or TCR may be administered, e.g., a dosage of $10^4$ to $10^9$ cells/kg body weight (e.g., $10^5$ to $10^6$ cells/kg body weight). In another embodiment, the therapeutically effective amount of the T cells is about $10^4$ cells, about $10^5$ cells, about $10^6$ cells, about $10^7$ cells, or about $10^8$ cells. The pharmaceutical composition may be administered at a dosage of, e.g., about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

A dose of engineered T cells or NK cells as described herein may be administered to a mammal at one time or in a series of subdoses administered over a suitable period of time, e.g., on a daily, semi-weekly, weekly, bi-weekly, semi-monthly, bi-monthly, semi-annual, or annual basis, as needed. A dosage unit comprising an effective amount of a binding agent may be administered in a single daily dose, or the total daily dosage may be administered in two, three, four, or more divided doses administered daily, as needed.

A suitable means of administration may be selected by a medical practitioner. Route of administration may be parenteral, for example, administration by injection, transnasal administration, transpulmonary administration, or transcutaneous administration. Administration may be systemic or local by intravenous injection, intramuscular injection, intraperitoneal injection, subcutaneous injection. In some embodiments, a composition is selected for parenteral delivery, for inhalation, or for delivery through the digestive tract, such as orally. Dose and method of administration may vary depending on the weight, age, condition, and the like of the subject, and may be suitably selected.

Selection or use of any form may depend, in part, on the intended mode of administration and therapeutic application. For example, a composition comprising an engineered cell of the present disclosure intended for systemic or local delivery may be in the form of injectable or infusible solutions. Accordingly, the compositions comprising an engineered of the present disclosure may be formulated for administration by a parenteral mode (e.g., intravenous, subcutaneous, intraperitoneal, or intramuscular injection). Parenteral administration refers to modes of administration other than enteral and topical administration, usually by injection, and comprise, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

In various embodiments, a pharmaceutical composition comprising an engineered cell of the present disclosure may be formulated as a solution, microemulsion, dispersion, liposome, or other ordered structure suitable for stable storage at high concentration. Sterile injectable solutions may be prepared by incorporating a composition comprising an engineered cell of the present disclosure in the required amount in an appropriate solvent with one or a combination of ingredients enumerated above, as required, followed by filter sterilization. Generally, dispersions are prepared by incorporating a composition comprising an engineered cell of the present disclosure into a sterile vehicle that contains a basic dispersion medium and the required other ingredients from those enumerated above. The proper fluidity of a solution may be maintained, for example, by the use of a coating such as lecithin, by the maintenance of the required particle size in the case of dispersion and by the use of surfactants. Prolonged absorption of injectable compositions comprising a binding agent of the present disclosure may be brought about by comprising in the composition comprising a binding agent of the present disclosure a reagent that delays absorption, for example, monostearate salts, and gelatin.

A pharmaceutical composition comprising an engineered cell of the present disclosure may be administered parenterally in the form of an injectable formulation comprising a sterile solution or suspension in water or another pharmaceutically acceptable liquid. For example, the pharmaceutical composition comprising an antigen binding system may be formulated by suitably combining the engineered cell with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient comprised in the pharmaceutical preparations is such that a suitable dose within the designated range is provided. Non-limiting examples of oily liquid comprise sesame oil and soybean oil, and it may be combined with benzyl benzoate or benzyl alcohol as a solubilizing agent. Other items that may be comprised are a buffer such as a phosphate buffer, or sodium acetate buffer, a soothing agent such as procaine hydrochloride, a stabilizer such as benzyl alcohol or phenol, and an antioxidant. The formulated injection may be packaged in a suitable ampule.

In some embodiments, a composition comprising an antigen binding system may be formulated for storage at a temperature below 0° C. (e.g., −20° C. or −80° C.). In some embodiments, the composition comprising an engineered cell of the present disclosure may be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions comprising an antigen binding system are stable in storage for at least 1 year at 2-8° C. (e.g., 4° C.).

In some instances, a pharmaceutical composition comprising an engineered of the present disclosure may be formulated as a solution. In some embodiments, a composition comprising an engineered cell of the present disclosure may be formulated, for example, as a buffered solution at a suitable concentration and suitable for storage at 2-8° C. (e.g., 4° C.). Pharmaceutical compositions comprising an engineered cell as described herein may be formulated in immunoliposome compositions. Liposomes with enhanced circulation time are disclosed in, e.g., U.S. Pat. No. 5,013,556.

In certain embodiments, compositions comprising an engineered cell of the present disclosure may be formulated with a carrier that will protect the composition against rapid release, such as a controlled release formulation, comprising implants and microencapsulated delivery systems. Biodegradable, biocompatible polymers may be used, such as ethylene vinyl acetate, polyanhydrides, polyglycolic acid, collagen, polyorthoesters, and polylactic acid. Many methods for the preparation of such formulations are known. See, e.g., J. R. Robinson (1978) "Sustained and Controlled Release Drug Delivery Systems," Marcel Dekker, Inc., New York.

In various embodiments, subcutaneous administration may be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with binding agent drug for subcutaneous injection.

An injection system of the present disclosure may employ a delivery pen as described in U.S. Pat. No. 5,308,341. Pen devices are commonly used for self-delivery of insulin to patients with diabetes. Such devices may comprise at least one injection needle (e.g., a 31 gauge needle of about 5 to 8 mm in length), are generally pre-filled with one or more therapeutic unit doses of a therapeutic solution, and are useful for rapidly delivering solution to a subject with as little pain as possible. One medication delivery pen comprises a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits comprise one or more disposable replacement needles. Pen devices suitable for delivery of any one of the presently featured compositions comprising a binding agent of the present disclosure are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition comprising an engineered cell of the present disclosure may be delivered to a subject by way of local administration that does not rely upon transport of the engineered cell to its intended target tissue or site via the vascular system. For example, the composition comprising an engineered cell of the present disclosure may be delivered by injection or implantation of the composition comprising an engineered cell of the present disclosure or by injection or implantation of a device containing the composition comprising an engineered cell of the present disclosure. In certain embodiments, following local administration in the vicinity of a target tissue or site, the composition comprising an engineered cell of the present disclosure, or one or more components thereof, may diffuse to an intended target tissue or site that is not the site of administration.

A pharmaceutical solution may comprise a therapeutically effective amount of a composition comprising an engineered cell of the present disclosure. Such effective amounts may be readily determined based, in part, on the effect of the administered composition comprising an engineered cell of the present disclosure, or the combinatorial effect of the composition comprising an engineered cell of the present disclosure and one or more additional active agents. A therapeutically effective amount of a composition comprising engineered T cells of the present disclosure may also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the complement-mediated disorder. For example, a therapeutically effective amount of a composition comprising an engineered cell of the present disclosure may inhibit (lessen the severity of or eliminate the occurrence of) and/or prevent a disorder, and/or any one of the symptoms of the disorder. A therapeutically effective amount is also one in which any toxic or detrimental effects of the composition comprising an engineered cell of the present disclosure are outweighed by the therapeutically beneficial effects.

A composition comprising an engineered cell of the present disclosure may be administered as a fixed dose, or in a milligram per kilogram (mg/kg) dose. In some embodiments, the dose may also be chosen to reduce or avoid production of antibodies or other host immune responses against one or more of the binding motifs molecules in the composition comprising an engineered cell of the present disclosure. While in no way intended to be limiting, exemplary dosages of a binding agent, such as a composition comprising an engineered cell of the present disclosure comprise, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition comprising an engineered cell of the present disclosure comprise, without limitation, 0.1 mg/kg, 0.5 mg/kg, 1.0 mg/kg, 2.0 mg/kg, 4 mg/kg, 8 mg/kg, or 20 mg/kg.

Suitable human doses of any of the compositions comprising a binding agent of the present disclosure may further be evaluated in, e.g., Phase I dose escalation studies. See, e.g., van Gurp et al. (2008) Am J Transplantation 8(8):1711-1718; Hanouska et al. (2007) Clin Cancer Res 13(2, part 1):523-531; and Hetherington et al. (2006) Antimicrobial Agents and Chemotherapy 50(10): 3499-3500.

The present disclosure provides methods and uses for increasing an immune response to a target antigen in a subject in need thereof, comprising administering, to the subject, an effective amount of immune cells as disclosed herein, wherein said immune cells comprise a membrane-bound IL-15-IL-15Rα chimeric polypeptide and a CAR or TCR. The present disclosure also provides methods for treating and/or preventing a cancer in a subject comprising administering, to the subject, an effective amount of immune cells as disclosed herein, wherein said immune cells comprise a membrane-bound IL-15-IL-15Rα chimeric polypeptide and a CAR or TCR. The present disclosure further provides a method of increasing cytokine production in response to a cancer or pathogen in a subject, comprising administering, to the subject, an effective amount of immune cells disclosed herein, wherein the immune cells comprise a membrane-bound IL-15-IL-15Rα chimeric polypeptide and a CAR or TCR. The present disclosure further provides a method of increasing phospho-STAT5 (pSTAT5), comprising administering, to the subject, an effective amount of immune cells disclosed herein, wherein the immune cells comprise a membrane-bound IL-15-IL-15Rα chimeric polypeptide, and optionally a CAR or TCR. The presently disclosed subject matter also provides a method of reducing tumor burden in a subject, the method comprising administering, to the subject, an effective amount of immune cells disclosed herein, wherein immune cells comprise a membrane-bound IL-15-IL-15Rα chimeric polypeptide and a CAR or TCR. Methods and uses of the present disclosure comprising administration of an pharmaceutically effective amount of the engineered cells of the present disclosure may also be used to increase T cell mediated cytotoxicity of target cells (compared to a control without a membrane-bound IL-15-IL-15Rα), increase production of IFN-γ and/or TNFα (compared to a control without a membrane-bound IL-15-IL-15Rα), reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, a method provided herein induces a complete response. In some embodiments, a method provided herein induces a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, Waldenstrom macroglobulinemia, or a combination thereof. In other embodiments, the cancer can be any of sarcomas (e.g., synovial sarcoma, osteogenic sarcoma, leiomyosarcoma uteri, and alveolar rhabdomyosarcoma), hepatocellular carcinoma, glioma, head cancers (e.g., squamous cell carcinoma), neck cancers (e.g., squamous cell carcinoma), bone cancer, brain cancer, breast cancer, cancer of the anus, anal canal, or anorectum, cancer of the eye, cancer of the intrahepatic bile duct, cancer of the joints, cancer of the neck, gall bladder, or pleura, cancer of the nose, nasal cavity, or middle ear, cancer of the oral cavity, cancer of the vulva, colon cancers (e.g., colon carcinoma), esophageal cancer, cervical cancer, gastric cancer, gastrointestinal carcinoid tumor, hypopharynx cancer, larynx cancer, liver cancers (e.g., hepatocellular carcinoma), lung cancers (e.g., non-small cell lung carcinoma), malignant mesothelioma, melanoma, nasopharynx cancer, ovarian cancer, pancreatic cancer, peritoneum, omentum, and mesentery cancer, pharynx cancer, prostate cancer, rectal cancer, kidney cancers (e.g., renal cell carcinoma), small intestine cancer, soft tissue cancer, stomach cancer, testicular cancer, thyroid cancer, and urothelial cancers (e.g., ureter cancer and urinary bladder cancer).

In various instances, a method of using an engineered cell comprising a CAR or TCR as provided herein to treat cancer is an autologous cell therapy. In various instances, a method of using an engineered cell comprising a CAR or TCR as provided herein to treat cancer is an allogeneic cell therapy.

In various embodiments, a cell therapy provided herein for use in the present disclosure may be administered to a subject in a course of treatment that further comprises administration of one or more additional therapeutic agents or therapies that are not a cell therapy provided herein. In certain embodiments, the present disclosure provides combination therapy for the treatment of cancer, the treatment comprising administering an anti-cancer agent to a subject receiving and/or in need of a cell therapy provided herein.

In certain embodiments, administration of an engineered cell comprising a CAR or TCR as provided herein may be to a subject having previously received, scheduled to receive, or in the course of a treatment regimen comprising an additional anti-cancer therapy. In various embodiments, an additional agent or therapy administered in combination with the engineered cell may be administered at the same time as the engineered cell, on the same day as the engineered cell, or in the same week as the engineered cell. In various embodiments, an additional agent or therapy administered in combination with an engineered cell comprising a CAR or TCR as provided herein may be administered such that administration of the engineered cell and the additional agent or therapy are separated by one or more hours before or after, one or more days before or after, one or more weeks before or after, or one or more months before or after administration of the engineered cell. In various embodiments, the administration frequency of one or more additional agents may be the same as, similar to, or different from the administration frequency of the engineered cell.

An agent or therapy used in combination with an engineered cell comprising a CAR or TCR as provided herein may be administered in a single therapeutic composition or dose together with the engineered cell, at the same time as the engineered cell in the form of a separate composition, or in a manner temporally distinct from the administration of the engineered cell. When an engineered cell comprising a CAR or TCR as provided herein is to be used in combination with an additional agent, the engineered cell may be co-formulated with the additional agent or the engineered cell may be formulated separately from the additional agent formulation.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m2/day and 2000 mg/m2/day) and specified doses of fludarabine (between 20 mg/m2/day and 900 mg/m2/day). One such dose regimen involves treating a patient comprising administering daily to the patient about 500 mg/m2/day of cyclophosphamide and about 60 mg/m2/day of fludarabine for three days prior to administration of a therapeutically effective amount of engineered T cells to the patient. In other embodiments, the engineered cells containing a CAR or TCR), and the chemotherapeutic agent are administered each in an amount effective to treat the disease or condition in the subject.

In certain embodiments, compositions comprising CAR- and/or TCR-expressing immune cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside (“Ara-C”); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell containing a CAR or TCR or nucleic acid encoding a CAR or TCR. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the engineered cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab (CureTech), and atezolizumab (Roche). Additional therapeutic agents suitable for use in combination with the disclosure include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab (Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune cells are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. “Cytokine” is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. A "cytokine," as used herein also refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12 (e.g. IL-12p40 and IL-12p35), IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control. The contents of all references cited throughout this application are expressly incorporated herein by reference.

EXAMPLES

Example 1

An engineered, membrane bound IL-15 tethered to IL-15Rα agonist receptor construct (membrane-bound interleukin-15 (IL-15)-IL-15Rα sushi domain chimeric polypeptide) was designed as shown in sequence of SEQ ID NO: 27. This construct is 273 amino acids in length and includes a signal peptide domain from amino acids 1-18 of IgE, a myc epitope tag, an AGS linker (SEQ ID NO: 3), the active form of IL-15 from amino acid 49 to 162, a GS linker (SEQ ID NO: 104), the sushi domain from amino acid 31 to 96 of IL-15Rα, a GS linker (SEQ ID NO: 104), a transmembrane domain from amino acid 171 to 190 of FAS, and a truncated intracellular domain of FAS that comprises 8 amino acids. The membrane bound IL-15 tethered to IL-15Rα described is displayed as a monomer on the T cell surface. The amino acid sequence of this receptor is shown below:

(SEQ ID NO: 27)

```
MDWTWILFLVAAATRVHSEQKLISEEDLAGSNWVNVISDLKKIEDLIQSM
HIDATLYTESDVHPSCKVTAMKCFLLELQVISLESGDASIHDTVENLIIL
ANNSLSSNGNVTESGCKECEELEEKNIKEFLQSFVHIVQMFINTSSGGGS
GGGGSGGGGSGGGGSGGGSITCPPPMSVEHADIWVKSYSLYSRERYICNS
GFKRKAGTSSLTECVLNKATNVAHWTTPSLKCIRDGGGGSGGGGSRSNLG
WLCLLLLPIPLIVWVKRKEVQKT.
```

In addition, a second engineered membrane bound IL-15 tethered to IL-15Rα agonist construct (membrane-bound IL-15-IL-15Rα sushi domain chimeric polypeptide) was also designed and synthesized according to the sequence of SEQ ID NO: 29 as shown below:

(SEQ ID NO: 29)

```
MDWTWILFLVAAATRVHSEQKLISEEDLAGSNWVNVISDLKKIEDLIQSM
HIDATLYTESDVHPSCKVTAMKCFLLELQVISLESGDASIHDTVENLIIL
ANNSLSSNGNVTESGCKECEELEEKNIKEFLQSFVHIVQMFINTSSGGGS
GGGGSGGGGSGGGGSGGGSITCPPPMSVEHADIWVKSYSLYSRERYICNS
GFKRKAGTSSLTECVLNKATNVAHWTTPSLKCIRDGGGGSGGGGSPILLT
CPTISILSFFSVALLVILACVLW.
```

This construct is also 273 amino acids in length and includes a signal peptide domain from amino acid 1-18 of IgE, a myc epitope tag, and AGS linker (SEQ ID NO: 3), the active form of IL-15 from amino acid 49 to 162, a GS linker (SEQ ID NO: 104), the sushi domain from amino acid 31 to 96 IL-15Rα, a GS linker (SEQ ID NO: 104), a transmembrane domain from amino acid 237 to 264 of a IL-7 CPT mutein. This membrane bound IL-15 tethered to IL-15Rα is believed to display as a dimer due to the ability of the cysteine residue in the transmembrane domain to form a disulfide bond. In this and the other Examples the two membrane-bound IL-15-IL-15Rα sushi domain chimeric polypeptides may be referred to as IL15 Sushi Monomer and IL15 Sushi Dimer to refer to the constructs with a FAS and IL-7 derived transmembrane domain, respectively.

Example 2

The two membrane-bound IL-15-IL-15Rα sushi domain chimeric polypeptides with N-terminal Myc epitope tags, as described in Example 1, were tested initially in T cells and then paired with two different CARs. The two CAR constructs utilized two different co-stimulatory domains (CD28 and 4-1BB) and are shown as follows:

a. CD19: (FMC63 scFv+CD28 intracellular domain+CD3ζ intracellular domain)

b. GPC3: (YP7 scFv+4-1BB intracellular domain+CD3ζ intracellular domain).

A lentivirus vector was used for all T-cell transductions. An EF1A promoter was used for the receptors tested in T-cells alone and with the GPC CAR pairing. The CD19 CAR utilized an mSCV promoter.

$CD3^+$ cells obtained from STEMCELL™ Technologies (Vancouver, Canada) were isolated from peripheral blood mononuclear cells obtained from healthy donors and frozen down in CryoStor® cell cryopreservation media (Sigma Aldrich®). Before lentivirus transduction, CD3 pan T cells were thawed, activated with CD3/CD28 Dynabeads®, (ThermoFisher Scientific) according to manufacturer recommendations and rested overnight. The following day cells were transduced with lentivirus containing the membrane bound IL-15-IL-15 Sushi Domain receptors as described herein.

Cells were grown for 12 days in TC Media (X-VIVO™, Lonza) with 5% human serum, supplemented three times per week with 100 International Units/ml of Interleukin-2 (IL-2). On day 12 the cells were centrifuged and resuspended in TC Media (X-VIVO™, Lonza) with 5% human serum with no IL-2 supplement. Transgene positive cells were measured by flow cytometry on days 6, 15, 20, 23 using Myc-Tag AF 647 Conjugate, DL650-anti-FMC63 for 19CAR+. Antti Whitlow-APC for GPC3 CAR, BUV737 for CD3, BUV563 for CD4 and BUV395 for CD8.

All flow cytometry data was collected on BD LSR-Fortessa™ (BD and Company) with BD FACSDiva™ software (BD and Company and data was analyzed using FlowJo (BD and Company). All antibody staining was performed at 4° C. in PBS containing 1% BSA. Cells were evaluated for viability and transgene expression for 23 days. Expression level and cell viability of transduced and non-transduced T cells cultured with TC Media with no supplemental IL-2 after day 12 are shown in Table 6.

TABLE 6

| | Myc+ (Mean Fluorescent Intensity (MFI)) | | | | % Viability | | | |
|---|---|---|---|---|---|---|---|---|
| Experimental Group | Day 6 | Day 15 | Day 20 | Day 23 | Day 6 | Day 15 | Day 20 | Day 23 |
| Untransduced T cells | 283 | 199 | 437 | 350 | 92 | 54 | 17 | 19 |
| IL-15-IL-15Rα Sushi Monomer | 1187 | 988 | 972 | 1037 | 90 | 80 | 69.9 | 88 |
| IL-15-IL-15Rα Sushi Dimer | 4270 | 521 | 607 | 569 | 90 | 75 | 42.7 | 58 |

Expression of membrane-bound IL-15-IL-15Rα sushi domain chimeric receptor was confirmed by staining the cells with an antibody directed to the Myc tag. The T cells transduced with either membrane-bound IL-15-IL-15Rα sushi domain chimeric receptor (monomer or dimer) displayed greater viability compared to un-transduced T cells indicating enhanced proliferation of the transduced T cells containing membrane-bound IL-15-IL-15Rα sushi domain chimeric receptor.

Example 3

To measure IL-15 pathway activation by the membrane-bound IL-15-IL-15Rα sushi domain chimeric receptors, equal numbers of transduced and non-transduced day six T cells were cultured in RPMI media without serum overnight.

Cells were then collected by centrifugation and lysed using MSD lysis buffer+protease and phosphatase inhibitors (Meso Scale Discovery) before MSD analysis for pSTAT5 levels. pSTAT5 signaling is an indicator of IL-15 pathway activation from the membrane-bound IL-15-IL-15Rα sushi domain chimeric receptors. The results are shown in Table 7 below:

TABLE 7

| Experimental Group | pSTAT5 MSD Signal |
|---|---|
| Untransduced T Cells | 215 |
| IL-15-IL-15Rα Sushi Monomer | 2239 |
| IL-15-IL-15Rα Sushi Dimer | 2091 |

T cells transduced with both IL-15-IL-15Rα sushi domain receptors have pSTAT5 signaling levels greater than 10-fold higher than non-transduced T cells as shown in Table 7.

Example 4

In order to investigate whether expressing the membrane-bound IL-15-IL-15Rα sushi domain chimeric receptors could enhance the persistence and effectiveness of T cell-based immunotherapy using chimeric antigen receptors (CARs), constructs were designed to encode the membrane-bound IL-15-IL-15Rα sushi domain chimeric receptor monomer and the membrane-bound IL-15-IL-15Rα sushi domain chimeric receptor dimer: with a CARs having scFvs specific to CD19 or GPC3, followed by a T2A self-cleaving peptide. CAR constructs without the IL-membrane-bound IL-15-IL-15Rα sushi domain chimeric receptors served as the positive control. By adding the membrane-bound IL-15-IL-15Rα sushi domain chimeric receptors, the enhanced CAR T cells stimulated the IL-15Rbeta/gamma signaling pathway for the activation and/or proliferation of IL-15Rbeta/gamma-positive T cells.

To determine if IL-15-IL-15Rα sushi domain chimeric receptors described herein could enhance persistence and effectiveness, $CD3^+$ cells were isolated from primary human peripheral blood mononuclear cells (PBMCs) and transduced with constructs comprising CD19 CAR only (FMC63 scFv+CD28 intracellular domain+CD3ζ intracellular domain), CD19 CAR+IL-15-IL-15Rα Sushi domain monomer or CD19 CAR+IL-15-IL-15Rα Sushi domain dimer.

19CAR, CD19 CAR+IL-15-IL-L5RαSushi domain monomer and CD19 CAR+L-15-IL-15Rα Sushi domain dimer T cells were assessed for expression and Mean Fluorescent Intensity (MFI), results are shown in table 8 below.

TABLE 8

% Expression and MFI of CD19 CAR + IL-15-IL-15Rα Sushi Domain Receptors

| | % Expression | | Mean Fluorescent Intensity (MFI) | |
|---|---|---|---|---|
| Experimental Group | 19CAR | IL-15 Receptor | 19CAR | IL-15 Receptor |
| Untransduced T cells | 0.945 | 0.075 | N/A | N/A |
| CD19 CAR | 68.09 | 0.29 | 2292 | 1186 |
| CD19 CAR + IL-15 Sushi Monomer | 42.9 | 28.5 | 1913 | 1699 |
| CD19 CAR + IL-15 Sushi Dimer | 51.03 | 43.6 | 1633 | 2387 |

Next, day eleven T cells were incubated o/n in RPMI media prepared whole cell lysates and pSTAT5 signaling was obtained. The results are described in Table 9.

TABLE 9

CD19 CAR + IL-15-IL-15Rα Sushi Domain Receptors activate pSTAT5 signaling pathway

| Experimental Group | pSTAT5 Signal |
|---|---|
| Untransduced T cells | 2202 |
| CD19 CAR | 1948 |
| CD19 CAR + IL-15 Sushi Monomer | 14526 |
| CD19 CAR + IL-15 Sushi Dimer | 15285 |

Background levels of pSTAT5 signaling in all engineered T cells are shown in Table 9.

Un-transduced T cells or T cells expressing CD19 CAR did not induce pSTAT5 signaling whereas T cells engineered with either 1IL-15-IL-15Rα sushi domain chimeric receptors induced roughly a greater than 7× increase in pSTAT5 signaling. This data confirms that the IL-15-IL-15Rα Sushi Monomer and IL-15-IL-15Rα Sushi dimer receptors can signal in trans in the context of 19CAR.

Example 5

Repeat stimulation with targets in a long-term in vitro killing assay often correlates with in vivo experimental results. Therefore, a serial stimulation assay was used to measure CD19 CAR T cell expansion and tested the effects of the IL-15-IL-15RαSushi domain monomer and the IL-15-IL-15RαSushi domain dimer in this assay. The expression levels of all CAR groups are as in Table 8 above.

CD19 CAR positive T cells were co-cultured with CD19 expressing Nalm6 target cells from American Type Culture Company (ATCC, Manassas, VA) at a 1:1 ratio for eighteen days. Target cells were added every three to four days at a 1:1 ratio based on the number of CAR+ T cells as measured by counting beads and flow cytometry.

To determine the consequence of IL-15-IL-15RαSushi domain monomer and the IL-15-IL-15RαSushi domain dimer on CD19 CAR T cell function, CD19 CAR T cells were stimulated six times for 18 days with $CD19^{+}$ Nalm6 target cells. Target mediated CAR T cell fold expansion as well as Nalm6% cytolysis was measured. The results are described in Table 10.

TABLE 10

CD19 CAR + 19CAR + IL15-IL-15Rα Sushi Monomer and Dimer T cell Fold Expansion

| Experimental | Day | | | | | |
|---|---|---|---|---|---|---|
| Group | 0 | 4 | 7 | 10 | 14 | 18 |
| 19CAR | 1 | 1.56 | 0.62 | 0.12 | 0.08 | 0.01 |
| 19CAR + IL15-IL-15Rα Sushi Monomer | 1 | 1.67 | 1.12 | 0.53 | 0.37 | 0.04 |
| 19CAR + IL15-IL-15Rα Sushi Dimer | 1 | 3.19 | 2.62 | 4.41 | 9.96 | 5.93 |

The results indicate the 19CAR+IL15-IL-15Rα Sushi Monomer and the 19CAR+IL15-IL-15Rα Sushi Dimer had greater CAR+ fold expansion through day eighteen compared to 19CAR alone. The expansion of the 19CAR+IL15-IL-15Rα Sushi Dimer expansion was 124× and 593× greater than 19CAR on day 14 and 18, respectively, contracting at day 14. The IL-15-IL-15Rα Sushi Dimer expansion was 5× greater than 19CAR on day 14, contracted after day ten. CAR T cell Nalm6 cell killing was measured. The results are described in Table 11.

TABLE 11

Serial Kill % Nalm6 Cytolysis

| | 19CAR | 19CAR + IL15-IL-15Rα Sushi Monomer | 19CAR + IL15-IL-15Rα Sushi Dimer |
|---|---|---|---|
| D 3 | 98.51 | 98.36 | 98.26 |
| D 6 | 97.24 | 98.84 | 98.22 |
| D 9 | 98.41 | 99.74 | 99.53 |
| D 13 | 87.56 | 99.18 | 99.87 |
| D 18 | −405.19 | 99.24 | 99.67 |

The serial killing results indicate that the 19CAR+IL15-IL-15Rα Sushi Monomer and the 19CAR+IL5-IL-15Rα Sushi Dimer outperformed the 19CAR by D09 at a 1:1 E:T ratio. The 19CAR did not kill the Nalm6 cells at day 18.

Example 6

IL-15 acts predominantly on the CD8+ subset. The CD8+ ratio from the serial kill was assessed and the results are in table 12. The results indicate a higher CD8+ T cell ratio through day fourteen compared to 19CAR alone.

TABLE 12

CD19 CAR + 19CAR + IL15-IL-15Rα Sushi Monomer and Dimer CD8+ subset t cell Ratio

| Experimental | Day | | | | | |
|---|---|---|---|---|---|---|
| Group | 0 | 4 | 7 | 10 | 14 | 18 |
| 19CAR | 0.34 | 0.60 | 0.75 | 0.82 | 0.58 | 0.87 |
| 19CAR + IL15-IL-15Rα Sushi Monomer | 0.51 | 0.86 | 0.92 | 0.97 | 0.96 | 0.97 |
| 19CAR + IL15-IL-15Rα Sushi Dimer | 0.43 | 0.81 | 0.92 | 0.95 | 0.96 | 0.99 |

Example 7

The CD19 CAR, CD19 CAR+19CAR+IL15-IL-15Rα Sushi Monomer and CD19 CAR+19CAR+IL15-IL-15Rα Dimer were tested in vivo in the Nalm6 disseminated mouse model.

CD19+ Nalm6 cells containing a bioluminescent reporter were grown in 90% RPMI, 10% FBS, 1% L-Glutamine. NSG mice (NOD.Cg-$Prkdc^{scid}$ $Il2rg^{tm1Wjl}$/SzJ) from Jackson Laboratory were used for the study. 8 week old mice were implanted by injecting intravenously via the lateral tail vein on day 0 with $5.0\times10^{5}$ CD19+ Nalm6 cells in 0.1 ml using a BD U-100 Insulin Syringes ½ cc, 28G. CAR-T cells were manufactured and edited as previously described. 100 ul of CAR-T cells from day 10 of manufacturing were dosed in mice through intravenous injection on day 7 post CD19+ Nalm6 implantation.

In vivo bioluminescence imaging was performed using an IVIS Lumina S5. Animals were imaged three at a time under ~2-3% isoflurane gas anesthesia. Each mouse was injected IP with 150 mg/kg D-luciferin and imaged in the prone 15 minutes after the injection. Large binning of the CCD chip was used, and the exposure time was adjusted to 30 second to obtain at least several hundred counts from the metastatic tumors that were observable in each mouse in the image and to avoid saturation of the CCD chip. BLI images were collected on days 5, 7, 12, 19, 23, 26, 29, 33, 43. Images were analyzed using the Living Image version 4.5.4 software. Whole body fixed-volume ROIs were placed on prone images for each individual animal and labeled based on animal identification. Total flux (photons/sec) was calculated and exported for all ROIs.

BLI (Bioluminescence imaging) values (shown as Mean±SEM) corresponding to CD19+ Nalm6 tumor burden in mice is presented for different treatment groups (Table 13). Higher values indicate higher tumor burden. The CD19 CAR+19CAR+IL15-IL-15Rα Sushi Monomer and CD19 CAR+IL15-IL-15Rα Dimer performed better against the canonical CD19CAR as determined by reduced BLI over the course of the study. The 19CAR+IL15-IL-15Rα Dimer performed the best followed by the 19CAR+IL15-IL-15Rα Sushi Monomer. The results of the in vivo study are shown in Table 13.

TABLE 14

% Expression and MFI of GPC3 CAR + IL-15-IL-15Rα Sushi Domain Receptors

| Experimental Group | % Expression GPC3CAR | % Expression IL-15 Receptor | MFI GPC3CAR | MFI IL-15 Receptor |
|---|---|---|---|---|
| Untransduced T cells | 0.51 | 0.037 | 10.3 | 110 |
| GPC3 CAR | 82.1 | 0.59 | 1349 | 130 |
| GPC3 CAR + IL-15 Sushi Monomer | 57.7 | 59.3 | 519 | 1415 |
| GPC3 CAR + IL-15 Sushi Dimer | 59.1 | 57.6 | 707 | 1392 |

TABLE 13

Bioluminescence imaging (BLI) of Mice dosed with 1e6 19CAR

| | Day 5 | Day 7 | Day 12 | Day 15 | Day 19 | Day 23 | Day 26 | Day 29 | Day 33 | Day 43 |
|---|---|---|---|---|---|---|---|---|---|---|
| Vehicle | 4.74E+06 | 3.36E+07 | 2.84E+09 | 1.74E+10 | 4.62E+10 | | | | | |
| | 6.01E+06 | 3.40E+07 | 5.53E+09 | 2.26E+10 | 3.35E+10 | | | | | |
| | 5.26E+06 | 5.58E+07 | 6.77E+09 | 2.35E+10 | 4.23E+10 | | | | | |
| Untransduced | 2.29E+06 | 2.45E+07 | 1.80E+09 | 1.47E+10 | 2.00E+10 | | | | | |
| T cells | 3.66E+06 | 4.71E+07 | 4.18E+09 | 1.28E+10 | 3.22E+10 | | | | | |
| | 8.45E+06 | 1.22E+08 | 8.03E+09 | 1.61E+10 | 2.86E+10 | | | | | |
| | 7.14E+06 | 6.71E+07 | 5.83E+09 | 2.21E+10 | 3.46E+10 | | | | | |
| 19CAR | 6.46E+06 | 5.91E+06 | 9.73E+05 | 9.96E+05 | 1.88E+06 | 6.45E+06 | 2.99E+07 | 1.43E+08 | 4.62E+08 | |
| | 4.64E+06 | 2.39E+06 | 9.54E+05 | 9.98E+05 | 1.27E+06 | 3.63E+06 | 1.06E+07 | 5.20E+07 | 9.54E+08 | |
| | 3.95E+06 | 5.15E+06 | 1.37E+06 | 1.26E+06 | 2.71E+06 | 3.63E+07 | 1.04E+08 | 8.66E+08 | 1.38E+10 | |
| | 3.34E+06 | 4.21E+06 | 9.99E+05 | 8.26E+05 | 8.06E+05 | 1.35E+06 | 7.14E+06 | 4.06E+07 | 1.51E+09 | |
| | 2.88E+06 | 3.14E+06 | 6.46E+05 | 1.08E+06 | 9.64E+05 | 2.80E+06 | 3.37E+06 | 1.68E+07 | 5.02E+07 | |
| | 6.44E+06 | 5.00E+06 | 8.07E+05 | 1.09E+06 | 1.50E+06 | 9.22E+06 | 1.29E+07 | 4.88E+07 | 5.29E+08 | |
| 19CAR + | 6.02E+06 | 4.43E+06 | 9.57E+05 | 8.40E+05 | 9.23E+05 | 6.28E+05 | 9.61E+05 | 8.12E+05 | 1.73E+06 | |
| IL15-IL- | 6.48E+06 | 2.42E+06 | 1.41E+06 | 9.26E+05 | 9.61E+05 | 7.93E+05 | 1.01E+06 | 1.06E+06 | 4.37E+07 | |
| 15Rα | 4.05E+06 | 2.77E+06 | 1.48E+06 | 5.15E+05 | 7.61E+05 | 7.39E+05 | 1.37E+06 | 3.66E+06 | 7.12E+06 | |
| Sushi | 7.59E+06 | 4.79E+06 | 9.23E+05 | 9.47E+05 | 9.87E+05 | 1.04E+06 | 1.32E+06 | 6.51E+06 | 5.22E+07 | |
| Monomer | 3.90E+06 | 3.32E+06 | 8.67E+05 | 1.00E+06 | 1.05E+06 | 1.27E+06 | 1.06E+06 | 1.54E+06 | 9.60E+06 | |
| | 3.86E+06 | 2.59E+06 | 7.62E+05 | 1.00E+06 | 1.29E+06 | 1.25E+06 | 8.72E+05 | 9.63E+05 | 9.03E+05 | |
| 19CAR + | 5.48E+06 | 4.13E+06 | 1.15E+06 | 9.05E+05 | 8.33E+05 | 7.49E+05 | 1.08E+06 | 1.03E+06 | 1.16E+06 | 3.50E+09 |
| IL15-IL- | 6.99E+06 | 7.44E+06 | 1.17E+06 | 1.01E+06 | 8.57E+05 | 9.08E+05 | 1.15E+06 | 1.60E+06 | 1.64E+06 | 1.29E+08 |
| 15Rα | 8.87E+06 | 5.45E+06 | 6.71E+05 | 9.05E+05 | 1.12E+06 | 8.00E+05 | 9.34E+05 | 1.05E+06 | 1.25E+06 | 6.72E+09 |
| Sushi | 4.06E+06 | 6.90E+06 | 9.46E+05 | 1.00E+06 | 7.99E+05 | 9.17E+05 | 6.79E+05 | 5.42E+05 | 7.76E+05 | 4.36E+07 |
| Dimer | 3.51E+06 | 2.88E+06 | 1.03E+06 | 1.11E+06 | 1.16E+06 | 1.17E+06 | 8.89E+05 | 1.13E+06 | 3.11E+06 | 2.34E+09 |
| | 3.73E+06 | 1.94E+06 | 1.40E+06 | 1.50E+06 | 1.03E+06 | 8.74E+05 | 8.57E+05 | 8.92E+05 | 1.37E+06 | 4.12E+09 |

Example 8

The GPC CAR, GPC CAR+IL15-IL-15Rα Sushi Monomer and GPC CAR+IL-15-IL-15Rα Dimer were tested in the solid tumor Hep3b mouse model.

CAR T cells were manufactured as follows. $CD3^+$ cells were isolated from primary human peripheral blood mononuclear cells (PBMCs) and transduced with constructs comprising GPC3 CAR only (YP7 scFv+4-1BB intracellular domain+CD3ζ intracellular domain), GPC3 CAR+IL-15-IL-15Rα Sushi domain monomer or GPC3 CAR+IL-15-IL-15Rα Sushi domain dimer.

The GPC3 CAR, GPC3 CAR+IL-15-IL-15Rα Sushi domain monomer and GPC3 CAR+IL-15-IL-15Rα Sushi domain dimer T cells were assessed for GPC3 CAR and mbIL-15_-IL-15Rα Sushi domain receptor expression and MFI, results are shown in Table 14 below.

Human hepatocellular carcinoma cells (Hep 3B2.1-7) were grown and implanted subcutaneously in the flanks of 6-8-week-old female NSG mice (NOD.Cg-$Prkdc^{scid}$ $Il2rg^{tm1\,Wjl}$/SzJ). Animals were sorted into 5 study groups. T cells were dosed at 2e6 were injected on day 18. Following implantation tumors were measured every 3 to 4 days using digital calipers, and tumor volume was calculated.

Tumor volume values corresponding to GPC3+ tumor burden in mice is presented for different treatment groups (Table 14). Higher values indicate higher tumor burden. The CD19 CAR+19CAR+IL15-IL-15Rα Sushi Monomer and CD19 CAR+IL15-IL-15Rα Dimer performed better against the canonical CD19CAR as determined by reduced tumor volume over the course of the study. The 19CAR+IL15-IL-15Rα monomer performed the best followed by the 19CAR+IL15-IL-15Rα Sushi dimer.

TABLE 15

Tumor Volume of mice dosed with 2e6 GPC3 CAR T cells

| | Day post inoculation | | | | | | | | |
|---|---|---|---|---|---|---|---|---|---|
| | 17 | 21 | 23 | 28 | 31 | 36 | 38 | 42 | 45 |
| Vehicle | 90.3 | 127.4 | 192.1 | 213.8 | 416.9 | 543.4 | 638.6 | 783.6 | 1127.2 |
| | 104.7 | 261.1 | 406 | 620.3 | 1025.2 | 1524.5 | 1839.7 | 2079.4 | |
| | 105.1 | 196.9 | 280.2 | 542.6 | 716.6 | 1148.7 | 1341.1 | 1878.6 | 1970.3 |
| | 122.7 | 261.6 | 334.7 | 528.6 | 834.8 | 1498.2 | 1728.2 | 2055.6 | |
| | 123.4 | 202.6 | 285.9 | 462.6 | 689.6 | 1046.6 | 1471.3 | 1666.8 | 2391.2 |
| | 139 | 246.6 | 326.6 | 710.6 | 669.5 | 1004.3 | 1058.2 | 1289.8 | 1660.2 |
| | 140.6 | 213.3 | 349.7 | 568.1 | 848.5 | 1197.2 | 1197.4 | 1440.1 | 2208.2 |
| | 188.7 | 314 | 490.8 | 722.7 | 937.2 | 1229.2 | 1201.8 | 1622.7 | 2089.5 |
| Untransduced | 90.3 | 195.3 | 239.2 | 357.6 | 494.7 | 868.5 | 1410.6 | 1573 | 2207.6 |
| | 103.9 | 231.4 | 331.1 | 456.5 | 691.8 | 1357.2 | 1564 | 2416.8 | |
| | 106.7 | 216.7 | 248.9 | 618.1 | 902.6 | 769.4 | 849.5 | 1089.5 | 1117.3 |
| | 122.6 | 209.8 | 371 | 688.1 | 962.2 | 1475.4 | 1813.9 | 2056.1 | |
| | 125.5 | 272.9 | 353.3 | 646.1 | 910.3 | 1290.7 | 1495.8 | 1758.2 | 2782 |
| | 137.3 | 243.5 | 352.5 | 371.4 | 453.7 | 1349.4 | 1511.5 | 2047.9 | |
| | 142.7 | 238.4 | 421.9 | 710.2 | 943.3 | 1708.6 | 1784.6 | 2446.5 | |
| | 182.6 | 368.2 | 514.7 | 912.2 | 1286.3 | 1727.9 | 1853 | 2398.5 | |
| GPC3 CAR | 93.6 | 253.6 | 422.2 | 618.1 | 772 | 968.1 | 1249.6 | 1365 | 1775.5 |
| | 103.9 | 173.1 | 241.3 | 281.8 | 454.1 | 528 | 529.1 | 587.8 | 802.7 |
| | 107.8 | 239.8 | 304.2 | 466.2 | 645.2 | 1002.5 | 1137 | 1570.6 | 1521.3 |
| | 121.9 | 293.4 | 358 | 466 | 779 | 1102.5 | 1265.3 | 1343.4 | 1914.1 |
| | 126.1 | 205 | 413.9 | 714.1 | 1100.2 | 1400.2 | 1629.4 | 2169.1 | |
| | 136.7 | 218.7 | 322.8 | 522.8 | 811.5 | 928.8 | 981.2 | 1386.7 | 1853.6 |
| | 144.1 | 221.8 | 369 | 548.9 | 765.6 | 856.5 | 1017 | 1121.6 | 1262.9 |
| | 179.4 | 313.4 | 456.2 | 658.7 | 598.3 | 200.9 | 119.7 | 75.6 | 0 |
| GPC3 | 95.5 | 205.1 | 266 | 296.6 | 190.7 | 108 | 62.9 | 49.6 | 69.4 |
| CAR + | 100 | 182.7 | 287.6 | 328 | 189.5 | 108.9 | 72.8 | 0 | 0 |
| 15 Sushi | 111.4 | 243.1 | 342.5 | 382.9 | 250.1 | 112.3 | 75 | 0 | 0 |
| Monomer | 117.5 | 254.6 | 324.2 | 212.5 | 165.3 | 113.4 | 0 | 0 | 0 |
| | 129 | 336.1 | 412.5 | 590.2 | 328.2 | 230.5 | 170.2 | 87.5 | 84.9 |
| | 133.8 | 354 | 429.6 | 403.9 | 335.1 | 192.2 | 164.7 | 121.4 | 0 |
| | 160.2 | 344.1 | 589.8 | 585.7 | 396.4 | 313.8 | 261.8 | 0 | 0 |
| | 167.8 | 305.9 | 355.5 | 486.9 | 272.9 | 150.2 | 141.3 | 68.8 | 38.4 |
| GPC3 | 95.8 | 248.9 | 303.6 | 422.5 | 396.5 | 192.8 | 199.9 | 66.3 | 0 |
| CAR + | 98.2 | 198.6 | 424.4 | 463.5 | 381.4 | 185.5 | 150.6 | 90.8 | 95.8 |
| 15 Sushi | 112.7 | 202.8 | 555.4 | 800.8 | 567.5 | 273.6 | 256.8 | 139.4 | 113.9 |
| Dimer | 114.9 | 183.2 | 372.7 | 780.5 | 818.3 | 730.7 | 629.6 | 593.8 | 673.4 |
| | 129.1 | 283 | 206.7 | 254.4 | 164.3 | 108.4 | 65 | 0 | 0 |
| | 133.5 | 299.9 | 381.1 | 624.1 | 476.3 | 219.9 | 276 | 208.9 | 264.3 |
| | 161 | 352.8 | 313.1 | 511.2 | 412.4 | 203.7 | 129.2 | 88.9 | 0 |
| | 164.9 | 226.9 | 498.3 | 533.6 | 628.5 | 254.9 | 203.7 | 161.7 | 154 |

| | Day post inoculation | | | | | | |
|---|---|---|---|---|---|---|---|
| | 50 | 56 | 58 | 62 | 65 | 70 | 72 |
| Vehicle | | | | | | | |
| Untransduced | | | | | | | |
| GPC3 CAR | 2465 | | | | | | |
| | 1167.1 | 1564.8 | 1879.9 | 2026.9 | | | |
| | 2113.2 | | | | | | |
| | 1918.6 | 2220.8 | | | | | |
| | 2312.4 | | | | | | |
| | 1796.7 | 2017 | | | | | |
| | 37.6 | 74.1 | 80.8 | 56.8 | 108 | 114.2 | 121.5 |
| GPC3 | 102 | 335.3 | 354.9 | 496.1 | 548.7 | 686.4 | |
| CAR + | 48.9 | 186.3 | 283.4 | 518.4 | 775.4 | 1649.4 | 2155.7 |
| 15 Sushi | 123.8 | 440.4 | 677.5 | 1343.3 | 1834.3 | 2872.5 | |
| Monomer | 0 | 71.8 | 141.2 | 58.8 | | | |
| | 126.9 | 311.6 | 534.9 | 898.3 | 919.6 | | |
| | 0 | 0 | 0 | | | | |
| | 0 | 0 | | | | | |
| | 92.6 | | | | | | |
| GPC3 | 0 | 36 | 92.1 | 300 | 451.6 | 827 | 1112 |
| CAR + | 132.2 | 186 | | | | | |
| 15 Sushi | 117.3 | 338.2 | 564.2 | 980.8 | 1328.4 | 2013.7 | |
| Dimer | 716.3 | 1327.3 | 1264.4 | 1766.9 | 2058 | | |
| | 0 | 38.2 | 89.5 | 132.9 | 212.6 | 465.8 | 625.1 |
| | 635.3 | 1416.7 | 1818.7 | 2809 | | | |
| | 0 | 0 | 0 | 69.6 | 189.9 | 506.8 | 813.9 |
| | 254.6 | 525.4 | 854.9 | 1429.9 | 1912.5 | 2921.4 | |

Example 9

NK-92 CD16+ (ATCC PTA-8836) is an interleukin-2 (IL-2) dependent Natural Killer Cell line. These cells were cultured in hTCM supplemented with 200 IU/mL IL-2 prior to lentiviral transduction with the IL-15-IL-15Rα Sushi domain monomer and the IL-15-IL-15Rα Sushi domain dimer receptors.

On the day of transduction, the cells were stimulated with IL-2 (100 U/mL) and human IL-12 (100 ng/mL Miltenyi) for 2 h before transduction. Following cytokine stimulation, cells were plated into each well of a 12 well plate. Viral supernatant were added for a multiplicity of infection of 20, 50 and 100 and polybrene (8 ug/mL final concentration) was added, cells were incubated o/n. The next day, the media was removed by centrifugation and the cell pellet was resuspended in hTCM with no supplemental IL-2. Control wells containing untransduced NK-92 CD16+ cells grown with and without supplemental IL-2 were included.

The cells were incubated for eight days. Supplemental IL-2 was added to the untransduced control cells (200 Iu/mL) every 2 days. Ki-67 and Myc MFI were determined by flow cytometry. The supernatant levels of secreted IFN-g and TNFa were determined by Meso Scale Discovery.

Proliferation of IL-15-IL-15Rα Sushi domain monomer and IL-15-IL-15Rα Sushi domain dimer transduced NK-92 CD16+ is shown in Table 16.

TABLE 16

Proliferation of IL-15-IL-15RαSushi domain monomer and IL-15-IL-15RαSushi domain dimer transduced NK-92 CD16+

| Experimental Group | MOI | % Alive Myc+ | % Alive Ki67+ | Myc+ MFI | Myc+/Ki67+ MFI |
|---|---|---|---|---|---|
| NK-92 CD16+ | 0 | 0 | 0 | n/a | n/a |
| NK-92 CD16+ plus IL-2 (100 U/mL) | 0 | 0 | 0 | n/a | n/a |
| IL-15-IL-15RαSushi domain monomer | 20 | 79.4 | 77.1 | 3184 | 1328 |
| IL-15-IL-15RαSushi domain monomer | 50 | 78.5 | 79.3 | 2947 | 1404 |
| IL-15-IL-15RαSushi domain monomer | 100 | 84.8 | 94 | 4085 | 1592 |
| IL-15-IL-15RαSushi domain dimer | 20 | 72.3 | 73.2 | 2644 | 1337 |
| IL-15-IL-15RαSushi domain dimer | 50 | 74.7 | 76.5 | 2602 | 1352 |
| IL-15-IL-15RαSushi domain dimer | 100 | 80.3 | 87.1 | 2381 | 1487 |

The results show that eight days post transduction NK-92 CD16+ cells expressing the IL-15-IL-15RαSushi domain monomer and IL-15-IL-15RαSushi domain dimer proliferated in the absence of supplemental IL-2 as determined by Ki-67 cell proliferation marker flow cytometry analysis.

A bystander effect was also observed when comparing the Myc+ subset to the Myc-subset indicating IL-15 is being transpresented to untransduced NK-92 CD16+ cells. The Cell count for the Myc+ and the Myc− subsets are shown in Table 17.

TABLE 17

| Experimental Group | MOI | Myc+/ Ki67+ Cell Count | Myc−/ Ki67+ Cell Count |
|---|---|---|---|
| NK-92 CD16+ | 0 | 0 | 74 |
| NK-92 CD16+ plus IL-2 (100 U/mL) | 0 | 0 | 19 |
| IL-15-IL-15RαSushi domain monomer | 20 | 4809 | 1331 |
| IL-15-IL-15RαSushi domain monomer | 50 | 6024 | 1707 |
| IL-15-IL-15RαSushi domain monomer | 100 | 1151 | 192 |
| IL-15-IL-15RαSushi domain dimer | 20 | 4043 | 1671 |
| IL-15-IL-15RαSushi domain dimer | 50 | 3776 | 1334 |
| IL-15-IL-15RαSushi domain dimer | 100 | 2852 | 685 |

The results indicate that IL-15 is being trans-presented to the untransduced cells of the transduced sample sets as determined by Ki-67 staining.

The supernatant levels of secreted IFN-g and TNFa are show in Table 18.

TABLE 18

Secreted IFN-g and TNF-a levels in the Cell Supernatant

| Experimental Group | MOI | IFN-g | TNF-a |
|---|---|---|---|
| NK-92 CD16+ | 0 | 1932 | 954 |
| NK-92 CD16+ plus IL-2 (100 U/mL) | 0 | 5707 | 2352 |
| IL-15-IL-15RαSushi domain monomer | 20 | 27438 | 1402 |
| IL-15-IL-15RαSushi domain monomer | 50 | 14156 | 2080 |
| IL-15-IL-15RαSushi domain monomer | 100 | 11144 | 2410 |
| IL-15-IL-15RαSushi domain dimer | 20 | 10175 | 2310 |
| IL-15-IL-15RαSushi domain dimer | 50 | 6817 | 2072 |
| IL-15-IL-15RαSushi domain dimer | 100 | 5794 | 1684 |

NK-92 CD16+ secrete IFN-g and TNF-a when activated. The results indicate an increased level of IFN-g in the supernatant of IL-15-IL-15RαSushi domain monomer and the IL-15-IL-15RαSushi domain dimer transduced cells vs non transduced non IL-2 supplemented cells. TNF-a levels of all transduced mb15 cells was greater than two-fold higher that when compared to IL-2± controls.

Example 10

A third, engineered, membrane bound IL-15 tethered to IL-15Rα agonist receptor construct (membrane-bound interleukin-15 (IL-15)-IL-15Rα sushi domain chimeric polypeptide) named IL-15 Sushi Hybrid was designed as shown in sequence of SEQ ID NO: 94. This construct is 372 amino acids in length and includes a signal peptide domain from amino acids 1-18 of IgE, a myc epitope tag, an AGS linker (SEQ ID NO: 3), the active form of IL-15 from amino acid 49 to 162, a GS linker (SEQ ID NO: 104), the extracellular domain of IL-15Rα from amino acid 31 to 195 of IL-15Rα, a GS linker (SEQ ID NO: 104), a transmembrane domain from amino acid 171 to 190 of FAS, and a truncated intracellular domain of FAS that comprises 8 amino acids. This membrane bound IL-15 tethered to IL-15Rα described is also displayed as a monomer on the T cell surface. The amino acid sequence of this receptor is shown below:

```
(SEQ ID NO: 94)
MDWTWILFLVAAATRVHSEQKLISEEDLAGSNWVNVISDLKKIEDLIQSM

HIDATLYTESDVHPSCKVTAMKCFLLELQVISLESGDASIHDTVENLII

LANNSLSSNGNVTESGCKECEELEEKNIKEFLQSFVHIVQMFINTSSGGG

SGGGGSGGGGSGGGGSGGGSITCPPPMSVEHADIWVKSYSLYSRERYICN

SGFKRKAGTSSLTECVLNKATNVAHWTTPSLKCIRDPALVHQRPAPPSTV
```

-continued

TTAGVTPQPESLSPSGKEPAASSPSSNNTAATTAAIVPGSQLMPSKSPST

GTTEISSHESSHGTPSQTTAKNWELTASASHQPPGGGGGSGGGGSRSNLG

WLCLLLLPIPLIVWVKRKEVQKT

This construct was built downstream of a CD19 CAR (FMC63 scFv+CD28 intracellular domain+CD3ζ intracellular domain) followed by a T2A self-cleaving peptide. This was compared with the CD19 CAR construct as a control. Both constructs were expressed using the mSCV promoter and delivered using lentiviral vectors.

$CD4^+/CD8^+$ cells were isolated in-house using (Prodigy™) from leukopak obtained from AllCells™ (Alameda, Calif.) healthy donors and frozen down in CryoStor® cell cryopreservation media (Sigma Aldrich®). Frozen $CD4^+/CD8^+$ T cells were thawed, activated with plate bound MACS GMP CD3 pure (OKT3) (Miltenyl Biotec) and soluble human anti-CD28 (BD Biosciences) according to manufacturer recommendations and rested overnight in Interleukin-2 (IL-2) (Prometheus). The following day cells were transduced with lentivirus vectors. Cells were grown for 8 days in T-Cell Media (OpTmizer™ CTS™ T-Cell Expansion Basal Medium) with Expansion Supplement, CTS Immune Cell SR, CTS Glutamax (Gibco™) supplemented during thaw, transduction, day 2 and 4 post transduction with Interleukin-2 (IL-2). On day 8 the cells were centrifuged and frozen in CryoStor® CS5 Media (BioLife Solutions*). Cells were thawed and rested overnight in TC Media (X-VIVO™, Lonza) with 5% human serum supplemented with Interleukin-2 (IL-2). Cells were measured by flow cytometry following day for assay start using Myc-Tag PE Conjugate, DL650-anti-FMC63 for 19CAR+, and BUV395 for CD3. All antibody staining was performed at room temperature in BD Pharmingen™ Azide containing Staining Buffer (FBS). All flow cytometry data was collected on BD FACSymphony™ A5 Cell Analyzer (BD and Company) with BD FACSDiva™ software (BD and Company and data was analyzed using FlowJo (BD and Company). The construct was expressed well as shown below in Table 19.

TABLE 19

% Expression and MFI of CD19 CAR + IL-15-IL-15Rα Sushi Domain Receptor

| | % Expression | | Mean Fluorescent Intensity (MFI) | |
|---|---|---|---|---|
| Experimental Group | 19CAR | IL-15 Receptor | 19CAR | IL-15 Receptor |
| CD19 CAR | 73.5 | 0.12 | 1245 | 239 |
| CD19 CAR + IL-15 Sushi Hybrid | 56.4 | 60.1 | 863 | 891 |

The IL-15 signaling induced by the IL-15 Sushi Hybrid was measured using the MSD based pSTAT5 assay as described in earlier examples. Briefly, equal number of CAR+ cells were rested overnight in serum free media (Lonza X-VIVO™). Cells were then centrifuged and lysed using lysis buffer+protease and phosphatase inhibitors (Meso Scale Discovery™) before MSD analysis for pSTAT5 levels. The results are shown in Table 20 below:

TABLE 20

CD19 CAR + IL-15-IL-15Rα Sushi Domain Receptor activates pSTAT5 signaling pathway

| Experimental Group | pSTAT5 Signal |
|---|---|
| CD19 CAR | 2973 |
| CD19 CAR + IL-15 Sushi Hybrid | 10919 |

T cells expressing CD19 CAR did not induce pSTAT5 signaling whereas T cells expressing the IL-15 Sushi Hybrid downstream of the CD19 CAR induced higher pSTAT5 signaling. This data confirms that the IL-15-IL-15Rα Sushi Hybrid is functional in the context of a CD19 CAR.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A membrane bound interleukin 15 (IL-15)-IL-15Rα sushi domain chimeric receptor, comprising the amino acid sequence selected from the group consisting of SEQ ID NOs: 27, 28, and 94.

2. The membrane bound IL-15-IL-15Rα sushi domain chimeric receptor of claim 1, further comprising a signaling sequence.

3. The membrane bound IL-15-IL-15Rα sushi domain chimeric receptor of claim 2, wherein the signaling sequence comprises the amino acid sequence according to one of SEQ ID NOS: 12-20.

4. The membrane bound IL-15-IL-15Rα sushi domain chimeric receptor of claim 3, wherein the signaling sequence comprises the amino acid sequence according to SEQ ID NO: 12.

5. A nucleic acid encoding a membrane bound IL-15-IL-15Rα sushi domain chimeric receptor, wherein the nucleic acid comprises the nucleic acid sequence according to a sequence selected from the group consisting of SEQ ID NO: 31, SEQ ID NO: 32, SEQ ID NO: 96, SEQ ID NO: 97, and SEQ ID NO: 100.

6. A recombinant vector comprising the nucleic acid of claim 5.

7. The nucleic acid of claim 5, wherein the nucleic acid further comprises a nucleic acid encoding a chimeric antigen receptor or a T cell receptor.

8. The nucleic acid of claim 7, wherein the chimeric antigen receptor or T cell receptor binds a tumor antigen.

9. The nucleic acid of claim 8, wherein the tumor antigen is selected from the group consisting of 2B4 (CD244), 4-1BB, 5T4, A33 antigen, adenocarcinoma antigen, adrenoceptor beta 3 (ADRB3), A kinase anchor protein 4 (AKAP- 4), alpha-fetoprotein (AFP), anaplastic lymphoma kinase (ALK), Androgen receptor, B7H3 (CD276), β2-integrins, BAFF, B-lymphoma cell, B cell maturation antigen (BCMA), bcr-abl (oncogene fusion protein consisting of breakpoint cluster region (BCR) and Abelson murine leukemia viral oncogene homolog 1 (Abl)), BhCG, bone marrow stromal cell antigen 2 (BST2), CCCTC-Binding Factor (Zinc Finger Protein)-Like (BORIS or Brother of the Regulator of Imprinted Sites), BST2, C242 antigen, 9-O-acetyl-CA19-9 marker, CA-125, CAEX, calreticulin, carbonic anhydrase 9 (CAIX), C-MET, CCR4, CCR5, CCR8, CD2, CD3, CD4, CD5, CD8, CD7, CD10, CD16, CD19, CD20, CD22, CD23 (IgE receptor), CD24, CD25, CD27, CD28, CD30 (TNFRSF8), CD33, CD34, CD38, CD40, CD40L, CD41, CD44, CD44V6, CD49f, CD51, CD52, CD56, CD63, CD70, CD72, CD74, CD79a, CD79b, CD80, CD84, CD96, CD97, CD100, CD123, CD125, CD133, CD137, CD138, CD150, CD152 (CTLA-4), CD160, CD171, CD179a, CD200, CD221, CD229, CD244, CD272 (BTLA), CD274 (PD-L1, B7H1), CD279 (PD-1), CD352, CD358, CD300 molecule-like family member f (CD300LF), Carcinoembryonic antigen (CEA), claudin 6 (CLDN6), C-type lectin-like molecule-1 (CLL-1 or CLECL1), C-type lectin domain family 12 member A (CLEC12A), a cytomegalovirus (CMV) infected cell antigen, CNT0888, CRTAM (CD355), CS-1 (also referred to as CD2 subset 1), CRACC, CD319, and 19A24), CTLA-4, Cyclin B 1, chromosome X open reading frame 61 (CXORF61), Cytochrome P450 1B 1 (CYP1B1), DNAM-1 (CD226), desmoglein 4, DR3, DR5, E-cadherin neoepitope, epidermal growth factor receptor (EGFR), EGFIR, epidermal growth factor receptor variant III (EGFRvIII), epithelial glycoprotein-2 (EGP-2), epithelial glycoprotein-40 (EGP-40), EGF-like module-containing mucin-like hormone receptor-like 2 (EMR2), elongation factor 2 mutated (ELF2M), endosialin, Epithelial cell adhesion molecule (EPCAM), ephrin type-A receptor 2 (EphA2), Ephrin B2, receptor tyrosine-protein kinases erb-B2,3,4 (erb-B2,3,4), ERBB, ERBB2 (Her2/neu), ERG (transmembrane protease, serine 2 (TMPRSS2) ETS fusion gene), ETA, ETS translocation-variant gene 6, located on chromosome 12p (ETV6-AML), Fc fragment of IgA receptor (FCAR or CD89), fibroblast activation protein alpha (FAP), FBP, Fc receptor-like 5 (FcRL5), fetal acetylcholine receptor (AChR), fibronectin extra domain-B, Fms-Like Tyrosine Kinase 3 (FLT3), folate-binding protein (FBP), folate receptor 1, folate receptor «, Folate receptor β, Fos-related antigen 1, Fucosyl, Fucosyl GM1; GM2, ganglioside G2 (GD2), ganglioside GD3 (aNeu5Ac (2-8) aNeu5Ac (2-3) bDGalp (1-4) bDGlcp (1-1) Cer), o-acetyl-GD2 ganglioside (OAcGD2), GITR (TNFRSF 18), GM1, ganglioside GM3, hexasaccharide portion of globoH glycoceramide (GloboH), glycoprotein 75, Glypican-3 (GPC3), glycoprotein 100 (gp100), GPNMB, G protein-coupled receptor 20 (GPR20), G protein-coupled receptor class C group 5, member D (GPRC5D), Hepatitis A virus cellular receptor 1 (HAVCR1), human Epidermal Growth Factor Receptor 2 (HER-2), HER2/neu, HER3, HER4, HGF, high molecular weight-melanoma-associated antigen (HMWMAA), human papilloma virus E6 (HPV E6), human papilloma virus E7 (HPV E7), heat shock protein 70-2 mutated (mut hsp70-2), human scatter factor receptor kinase, human Telomerase reverse transcriptase (hTERT), HVEM, ICOS, insulin-like growth factor receptor 1 (IGF-1 receptor), IGF-I, IgG1, immunoglobulin lambda-like polypeptide 1 (IGLL1), IL-6, Interleukin 11 receptor alpha (IL-IIRα), IL-13, Interleukin-13 receptor subunit alpha-2 (IL-13Rx2 or CD213A2), insulin-like growth factor I receptor (IGF1-R), integrin α5β1, integrin αvβ3, intestinal carboxyl esterase, K-light chain, KCS1, kinase insert domain receptor (KDR), KIR, KIR2DL1, KIR2DL2, KIR2DL3, KIR3DL2, KIR-L, KG2D ligands, KIT (CD117), KLRGI, LAGE-1a, LAG3, lymphocyte-specific protein tyrosine kinase (LCK), Leukocyte immunoglobulin-like receptor subfamily A member 2 (LILRA2), legumain, Leukocyte-associated immunoglobulin-like receptor 1 (LAIR1), Lewis (Y) antigen, LeY, LG, LI cell adhesion molecule (LI-CAM), LIGHT, LMP2, lymphocyte antigen 6 complex, LTBR, locus K 9 (LY6K), Ly-6, lymphocyte antigen 75 (LY75), melanoma cancer testis antigen-1 (MAD-CT-1); melanoma cancer testis antigen-2 (MAD-CT-2), MAGE, Melanoma-associated antigen 1 (MAGE-A1), MAGE-A3 melanoma antigen recognized by T cells 1 (MelanA or MARTI), MelanA/MARTI, Mesothelin, MAGE A3, melanoma inhibitor of apoptosis (ML-IAP), melanoma-specific chondroitin-sulfate proteoglycan (MCSCP), MORAb-009, MS4A1, Mucin 1 (MUC1), MUC2, MUC3, MUC4, MUC5AC, MUC5b, MUC7, MUC16, mucin CanAg, Mullerian inhibitory substance (MIS) receptor type II, v-myc avian myelocytomatosis viral oncogene neuroblastoma derived homolog (MYCN), N-glycolylneuraminic acid, N-Acetyl glucosaminyl-transferase V (NA17), neural cell adhesion molecule (NCAM), NKG2A, NKG2C, NKG2D, NKG2E ligands, NKR-P IA, NPC-1C, NTB-A, mammary gland differentiation antigen (NY-BR-1), NY-ESO-1, oncofetal antigen (h5T4), Olfactory receptor 51E2 (OR51E2), OX40, plasma cell antigen, poly SA, proacrosin binding protein sp32 (OY-TES 1), p53, p53 mutant, pannexin 3 (PANX3), prostatic acid phosphatase (PAP), paired box protein Pax-3 (PAX3), Paired box protein Pax-5 (PAX5), prostate carcinoma tumor antigen-1 (PCTA-1 or Galectin 8), PD-1H, Platelet-derived growth factor receptor alpha (PDGFR-alpha), PDGFR-beta, PDL192, PEN-5, phosphatidylserine, placenta-specific 1 (PLAC1), Polysialic acid, Prostase, prostatic carcinoma cells, prostein, Protease Serine 21 (Testisin or PRSS21), Proteinase3 (PR1), prostate stem cell antigen (PSCA), prostate-specific membrane antigen (PSMA), Proteasome (Prosome, Macropain) Subunit, Beta Type, Receptor for Advanced Glycation Endproducts (RAGE-1), RANKL, Ras mutant, Ras Homolog Family Member C (RhoC), RON, Receptor tyrosine kinase-like orphan receptor 1 (ROR1), renal ubiquitous 1 (RU1), renal ubiquitous 2 (RU2), sarcoma translocation breakpoints, Squamous Cell Carcinoma Antigen Recognized By T Cells 3 (SART3), SAS, SDC1, SLAMF7, sialyl Lewis adhesion molecule (sLe), Siglec-3, Siglec-7, Siglec-9, sonic hedgehog (SHH), sperm protein 17 (SPA17), Stage-specific embryonic antigen-4 (SSEA-4), STEAP, sTn antigen, synovial sarcoma X breakpoint 2 (SSX2), Survivin, Tumor-associated glycoprotein 72 (TAG72), TCR5γ, TCRα, TCRβ, TCRγ Alternate Reading Frame Protein (TARP), telomerase, TIGIT, TNF-α precursor, tumor endothelial marker 1 (TEM1/CD248), tumor endothelial marker 7-related (TEM7R), tenascin C, TGF-β1, TGF-β2, transglutaminase 5 (TGS5), angiopoietin-binding cell surface receptor 2 (Tie 2), TACI, TIM1, TIM2, TIM3, Tn Ag, TRAIL-R1, TRAIL-R2, Tyrosinase-related protein 2 (TRP-2), thyroid stimulating hormone receptor (TSHR), tumor antigen CTAA16.88, Tyrosinase, uroplakin 2 (UPK2), VEGF-A, VEGFR-1, vascular endothelial growth factor receptor 2 (VEGFR2), vimentin, Wilms tumor protein (WT1), and X Antigen Family Member 1A (XAGE1).

10. An immune cell comprising the membrane bound IL-15-IL-15Rα sushi domain chimeric receptor of claim 1.

11. The immune cell of claim 10, wherein the cell is a T cell or a Natural Killer (NK) cell.

12. A pharmaceutical composition comprising the immune cell of claim 10.

* * * * *

SEQUENCE LISTING

```
<160> NUMBER OF SEQ ID NOS: 109

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys His Tyr Ser Glu Leu
1               5


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: V or I
<220> FEATURE:
<221> NAME/KEY: MOD_RES
<222> LOCATION: (4)..(4)
<223> OTHER INFORMATION: Any amino acid

<400> SEQUENCE: 2

Asp Xaa Glu Xaa Asn Pro Gly Pro
1               5


<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Ser
1


<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Ser Gly Gly Gly Gly Ser Gly Gly Gly Gly Ser Gly Gly
1               5                   10                  15

Gly Gly Ser Gly Gly Gly Ser
            20


<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Gly Ser
1               5                   10


<210> SEQ ID NO 6
<211> LENGTH: 114
<212> TYPE: PRT
<213> ORGANISM: Homo sapiens

<400> SEQUENCE: 6

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
```

```
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 7
<211> LENGTH: 66
<212> TYPE: PRT
<213> ORGANISM: Homo sapiens

<400> SEQUENCE: 7

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp
65


<210> SEQ ID NO 8
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (2)..(46)
<223> OTHER INFORMATION: This region may encompass 1-9 “Gly Gly Gly Gly
      Ser” repeating units
<220> FEATURE:
<223> OTHER INFORMATION: See specification as filed for detailed
      description of substitutions and preferred embodiments

<400> SEQUENCE: 8

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser
        35                  40                  45


<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Gly Gly Gly Gly Ser Gly Gly Gly Gly Ser Gly Gly Gly Gly Ser
1               5                   10                  15


<210> SEQ ID NO 10
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 10

Ser Gly Gly Gly Ser Gly Gly Gly Gly Ser Gly Gly Gly Ser
1               5                   10


<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Gly Gly Ser Gly Gly Gly Gly Ser Gly Gly Gly Gly Ser Gly
1               5                   10                  15

Gly Gly Gly Ser Gly Gly Gly Ser
            20


<210> SEQ ID NO 12
<211> LENGTH: 18
<212> TYPE: PRT
<213> ORGANISM: Homo sapiens

<400> SEQUENCE: 12

Met Asp Trp Thr Trp Ile Leu Phe Leu Val Ala Ala Ala Thr Arg Val
1               5                   10                  15

His Ser


<210> SEQ ID NO 13
<211> LENGTH: 20
<212> TYPE: PRT
<213> ORGANISM: Homo sapiens

<400> SEQUENCE: 13

Met Tyr Arg Met Gln Leu Leu Ser Cys Ile Ala Leu Ser Leu Ala Leu
1               5                   10                  15

Val Thr Asn Ser
            20


<210> SEQ ID NO 14
<211> LENGTH: 20
<212> TYPE: PRT
<213> ORGANISM: Mus sp.

<400> SEQUENCE: 14

Met Tyr Ser Met Gln Leu Ala Ser Cys Val Thr Leu Thr Leu Val Leu
1               5                   10                  15

Leu Val Asn Ser
            20


<210> SEQ ID NO 15
<211> LENGTH: 20
<212> TYPE: PRT
<213> ORGANISM: Homo sapiens

<400> SEQUENCE: 15
```

```
Met Glu Thr Pro Ala Gln Leu Leu Phe Leu Leu Leu Leu Trp Leu Pro
1               5                   10                  15

Asp Thr Thr Gly
            20


<210> SEQ ID NO 16
<211> LENGTH: 20
<212> TYPE: PRT
<213> ORGANISM: Mus sp.

<400> SEQUENCE: 16

Met Glu Thr Asp Thr Leu Leu Leu Trp Val Leu Leu Leu Trp Val Pro
1               5                   10                  15

Gly Ser Thr Gly
            20


<210> SEQ ID NO 17
<211> LENGTH: 21
<212> TYPE: PRT
<213> ORGANISM: Homo sapiens

<400> SEQUENCE: 17

Met Ala Leu Pro Val Thr Ala Leu Leu Leu Pro Leu Ala Leu Leu Leu
1               5                   10                  15

His Ala Ala Arg Pro
            20


<210> SEQ ID NO 18
<211> LENGTH: 16
<212> TYPE: PRT
<213> ORGANISM: Homo sapiens

<400> SEQUENCE: 18

Met Lys Trp Val Thr Phe Ile Ser Leu Leu Phe Ser Ser Ala Tyr Ser
1               5                   10                  15


<210> SEQ ID NO 19
<211> LENGTH: 48
<212> TYPE: PRT
<213> ORGANISM: Homo sapiens

<400> SEQUENCE: 19

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45


<210> SEQ ID NO 20
<211> LENGTH: 30
<212> TYPE: PRT
<213> ORGANISM: Homo sapiens

<400> SEQUENCE: 20

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30


<210> SEQ ID NO 21
<211> LENGTH: 10
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Gln Lys Leu Ile Ser Glu Glu Asp Leu
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gly Trp Leu Cys Leu Leu Leu Leu Pro Ile Pro Leu Ile Val Trp
1               5                   10                  15

Val

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Ile Leu Leu Thr Cys Pro Thr Ile Ser Ile Leu Ser Phe Phe Ser
1               5                   10                  15

Val Ala Leu Leu Val Ile Leu Ala Cys Val Leu Trp
            20                  25

<210> SEQ ID NO 24
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(45)
<223> OTHER INFORMATION: This sequence may encompass 1-9 “Gly Gly Gly
      Gly Ser” repeating units
<220> FEATURE:
<223> OTHER INFORMATION: See specification as filed for detailed
      description of substitutions and preferred embodiments

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Gly Gly Gly Ser
1 5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gly Gly Gly Gly Ser Gly Gly Gly Gly Ser
1 5 10

<210> SEQ ID NO 27
<211> LENGTH: 273
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

Met Asp Trp Thr Trp Ile Leu Phe Leu Val Ala Ala Ala Thr Arg Val
1 5 10 15

His Ser Glu Gln Lys Leu Ile Ser Glu Glu Asp Leu Ala Gly Ser Asn
20 25 30

Trp Val Asn Val Ile Ser Asp Leu Lys Lys Ile Glu Asp Leu Ile Gln
35 40 45

Ser Met His Ile Asp Ala Thr Leu Tyr Thr Glu Ser Asp Val His Pro
50 55 60

Ser Cys Lys Val Thr Ala Met Lys Cys Phe Leu Leu Glu Leu Gln Val
65 70 75 80

Ile Ser Leu Glu Ser Gly Asp Ala Ser Ile His Asp Thr Val Glu Asn
85 90 95

Leu Ile Ile Leu Ala Asn Asn Ser Leu Ser Ser Asn Gly Asn Val Thr
100 105 110

Glu Ser Gly Cys Lys Glu Cys Glu Glu Leu Glu Glu Lys Asn Ile Lys
115 120 125

Glu Phe Leu Gln Ser Phe Val His Ile Val Gln Met Phe Ile Asn Thr
130 135 140

Ser Ser Gly Gly Gly Ser Gly Gly Gly Gly Ser Gly Gly Gly Gly Ser
145 150 155 160

Gly Gly Gly Gly Ser Gly Gly Gly Ser Ile Thr Cys Pro Pro Pro Met
165 170 175

Ser Val Glu His Ala Asp Ile Trp Val Lys Ser Tyr Ser Leu Tyr Ser
180 185 190

Arg Glu Arg Tyr Ile Cys Asn Ser Gly Phe Lys Arg Lys Ala Gly Thr
195 200 205

Ser Ser Leu Thr Glu Cys Val Leu Asn Lys Ala Thr Asn Val Ala His
210 215 220

Trp Thr Thr Pro Ser Leu Lys Cys Ile Arg Asp Gly Gly Gly Gly Ser
225 230 235 240

Gly Gly Gly Gly Ser Arg Ser Asn Leu Gly Trp Leu Cys Leu Leu Leu
245 250 255

Leu Pro Ile Pro Leu Ile Val Trp Val Lys Arg Lys Glu Val Gln Lys
260 265 270

Thr

<210> SEQ ID NO 28
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Asn Trp Val Asn Val Ile Ser Asp Leu Lys Lys Ile Glu Asp Leu Ile
1 5 10 15

Gln Ser Met His Ile Asp Ala Thr Leu Tyr Thr Glu Ser Asp Val His
20 25 30

Pro Ser Cys Lys Val Thr Ala Met Lys Cys Phe Leu Leu Glu Leu Gln
35 40 45

Val Ile Ser Leu Glu Ser Gly Asp Ala Ser Ile His Asp Thr Val Glu
50 55 60

Asn Leu Ile Ile Leu Ala Asn Asn Ser Leu Ser Ser Asn Gly Asn Val
65 70 75 80

Thr Glu Ser Gly Cys Lys Glu Cys Glu Glu Leu Glu Glu Lys Asn Ile
85 90 95

Lys Glu Phe Leu Gln Ser Phe Val His Ile Val Gln Met Phe Ile Asn
100 105 110

Thr Ser Ser Gly Gly Gly Ser Gly Gly Gly Gly Ser Gly Gly Gly Gly
115 120 125

Ser Gly Gly Gly Gly Ser Gly Gly Gly Ser Ile Thr Cys Pro Pro Pro
130 135 140

Met Ser Val Glu His Ala Asp Ile Trp Val Lys Ser Tyr Ser Leu Tyr
145 150 155 160

Ser Arg Glu Arg Tyr Ile Cys Asn Ser Gly Phe Lys Arg Lys Ala Gly
165 170 175

Thr Ser Ser Leu Thr Glu Cys Val Leu Asn Lys Ala Thr Asn Val Ala
180 185 190

His Trp Thr Thr Pro Ser Leu Lys Cys Ile Arg Asp Gly Gly Gly Gly
195 200 205

Ser Gly Gly Gly Gly Ser Arg Ser Asn Leu Gly Trp Leu Cys Leu Leu
210 215 220

Leu Leu Pro Ile Pro Leu Ile Val Trp Val Lys Arg Lys Glu Val Gln
225 230 235 240

Lys Thr

<210> SEQ ID NO 29
<211> LENGTH: 273
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Asp Trp Thr Trp Ile Leu Phe Leu Val Ala Ala Ala Thr Arg Val
1 5 10 15

His Ser Glu Gln Lys Leu Ile Ser Glu Glu Asp Leu Ala Gly Ser Asn

```
            20                  25                  30

Trp Val Asn Val Ile Ser Asp Leu Lys Lys Ile Glu Asp Leu Ile Gln
        35                  40                  45

Ser Met His Ile Asp Ala Thr Leu Tyr Thr Glu Ser Asp Val His Pro
    50                  55                  60

Ser Cys Lys Val Thr Ala Met Lys Cys Phe Leu Leu Glu Leu Gln Val
65                  70                  75                  80

Ile Ser Leu Glu Ser Gly Asp Ala Ser Ile His Asp Thr Val Glu Asn
                85                  90                  95

Leu Ile Ile Leu Ala Asn Asn Ser Leu Ser Ser Asn Gly Asn Val Thr
            100                 105                 110

Glu Ser Gly Cys Lys Glu Cys Glu Glu Leu Glu Glu Lys Asn Ile Lys
        115                 120                 125

Glu Phe Leu Gln Ser Phe Val His Ile Val Gln Met Phe Ile Asn Thr
    130                 135                 140

Ser Ser Gly Gly Gly Ser Gly Gly Gly Gly Ser Gly Gly Gly Gly Ser
145                 150                 155                 160

Gly Gly Gly Gly Ser Gly Gly Gly Ser Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
    210                 215                 220

Trp Thr Thr Pro Ser Leu Lys Cys Ile Arg Asp Gly Gly Gly Gly Ser
225                 230                 235                 240

Gly Gly Gly Gly Ser Pro Ile Leu Leu Thr Cys Pro Thr Ile Ser Ile
                245                 250                 255

Leu Ser Phe Phe Ser Val Ala Leu Leu Val Ile Leu Ala Cys Val Leu
            260                 265                 270

Trp


<210> SEQ ID NO 30
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
```

```
            100                 105                 110

Thr Ser Ser Gly Gly Gly Ser Gly Gly Gly Gly Ser Gly Gly Gly Gly
        115                 120                 125

Ser Gly Gly Gly Gly Ser Gly Gly Gly Ser Ile Thr Cys Pro Pro Pro
    130                 135                 140

Met Ser Val Glu His Ala Asp Ile Trp Val Lys Ser Tyr Ser Leu Tyr
145                 150                 155                 160

Ser Arg Glu Arg Tyr Ile Cys Asn Ser Gly Phe Lys Arg Lys Ala Gly
                165                 170                 175

Thr Ser Ser Leu Thr Glu Cys Val Leu Asn Lys Ala Thr Asn Val Ala
            180                 185                 190

His Trp Thr Thr Pro Ser Leu Lys Cys Ile Arg Asp Gly Gly Gly Gly
        195                 200                 205

Ser Gly Gly Gly Gly Ser Pro Ile Leu Leu Thr Cys Pro Thr Ile Ser
    210                 215                 220

Ile Leu Ser Phe Phe Ser Val Ala Leu Leu Val Ile Leu Ala Cys Val
225                 230                 235                 240

Leu Trp


<210> SEQ ID NO 31
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

gctggaagca attgggtgaa cgtgatctcc gacctcaaga agatcgagga tctgatccag     60

tccatgcaca tcgatgccac actctacacc gagtccgatg tgcaccctag ctgcaaagtt    120

acagccatga aatgctttct gctggagctg caagtgatct ctctggagtc cggagatgct    180

tccatccacg acacagtgga gaatctgatc attctggcta acaactccct ctccagcaac    240

ggcaatgtca cagagtccgg ctgcaaagag tgtgaagagc tggaggagaa aaacatcaaa    300

gagtttctgc agagcttcgt ccacatcgtc cagatgttca tcaacacctc ctcc          354


<210> SEQ ID NO 32
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

gccggcagca actgggtcaa cgtgatctcc gatctgaaga agatcgaaga tctgatccag     60

tccatgcaca tcgatgccac actgtacacc gagagcgacg tgcaccccag ctgcaaagtt    120

acagccatga agtgctttct gctcgaactg caagtgattt ctctggagag cggagatgcc    180

agcatccacg acaccgtgga gaatctgatc attctggcca acaactctct gagcagcaac    240

ggcaatgtga cagagtccgg ctgtaaggag tgcgaggagc tggaggagaa aaacatcaaa    300

gagtttctgc agagcttcgt ccacattgtc caaatgttca tcaacaccag cagc          354


<210> SEQ ID NO 33
<211> LENGTH: 198
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 33
attacatgcc ctccccccat gtccgtggaa catgccgaca tctgggtgaa gtcctactct 60
ctgtactcgc gtgaacgtta tatctgcaac agcggcttta agaggaaggc cggaacctcc 120
tctctgaccg aatgtgtgct gaacaaggcc accaatgtgg ctcactggac cacacctagc 180
ctcaagtgta ttagggac 198

<210> SEQ ID NO 34
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
agaagcaatc tgggctggct gtgtctgctg ctgctcccca tccctctgat tgtgtgggtc 60
aagaggaagg aggtccagaa aacc 84

<210> SEQ ID NO 35
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
cctattctgc tgacatgccc caccatctcc atcctgtctt ttttttctgt tgctctgctg 60
gtgattctgg cttgcgtgct gtgg 84

<210> SEQ ID NO 36
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
ggcggcggca gcggcggcgg cggatccggc ggaggaggca gcggaggagg aggaagcgga 60
ggaggctcc 69

<210> SEQ ID NO 37
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
ggcggcggct ccggcggcgg aggctccggc ggaggcggat ccggcggcgg cggatccggc 60
ggaggatcc 69

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcggcggag gatccggagg aggcggatct 30

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggcggcggag gaagcggagg aggaggaagc 30

<210> SEQ ID NO 40
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gctggaagca attgggtgaa cgtgatctcc gacctcaaga agatcgagga tctgatccag 60
tccatgcaca tcgatgccac actctacacc gagtccgatg tgcaccctag ctgcaaagtt 120
acagccatga aatgctttct gctggagctg caagtgatct ctctggagtc cggagatgct 180
tccatccacg acacagtgga gaatctgatc attctggcta acaactccct ctccagcaac 240
ggcaatgtca cagagtccgg ctgcaaagag tgtgaagagc tggaggagaa aaacatcaaa 300
gagtttctgc agagcttcgt ccacatcgtc cagatgttca tcaacacctc ctccggcggc 360
ggcagcggcg gcggcggatc cggcggagga ggcagcggag gaggaggaag cggaggaggc 420
tccattacat gccctccccc catgtccgtg gaacatgccg acatctgggt gaagtcctac 480
tctctgtact cgcgtgaacg ttatatctgc aacagcggct ttaagaggaa ggccggaacc 540
tcctctctga ccgaatgtgt gctgaacaag gccaccaatg tggctcactg gaccacacct 600
agcctcaagt gtattaggga cggcggcgga ggatccggag gaggcggatc tagaagcaat 660
ctgggctggc tgtgtctgct gctgctcccc atccctctga ttgtgtgggt caagaggaag 720
gaggtccaga aaacc 735

<210> SEQ ID NO 41
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gccggcagca actgggtcaa cgtgatctcc gatctgaaga agatcgaaga tctgatccag 60
tccatgcaca tcgatgccac actgtacacc gagagcgacg tgcaccccag ctgcaaagtt 120
acagccatga agtgctttct gctcgaactg caagtgattt ctctggagag cggagatgcc 180
agcatccacg acaccgtgga gaatctgatc attctggcca acaactctct gagcagcaac 240
ggcaatgtga cagagtccgg ctgtaaggag tgcgaggagc tggaggagaa aaacatcaaa 300

```
gagtttctgc agagcttcgt ccacattgtc caaatgttca tcaacaccag cagcggcggc    360

ggctccggcg gcggaggctc cggcggaggc ggatccggcg gcggcggatc cggcggagga    420

tccattacat gccccctcc catgtccgtg gaacacgccg acatctgggt gaagagctac    480

tctctgtaca gcagagagcg ttacatctgc aacagcggct ttaagaggaa agccggcacc    540

agcagcctca cagagtgcgt gctcaacaag gccaccaacg tcgcccattg gaccaccccc    600

tctctgaagt gtattaggga cggcggcgga ggaagcggag gaggaggaag ccctattctg    660

ctgacatgcc ccaccatctc catcctgtct ttttttctg ttgctctgct ggtgattctg    720

gcttgcgtgc tgtggtga                                                  738


<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Asn Leu Gly Trp Leu Cys Leu Leu Leu Leu Pro Ile Pro Leu
1               5                   10                  15

Ile Val Trp Val Lys Arg Lys Glu Val Gln Lys Thr
            20                  25


<210> SEQ ID NO 43
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Trp Thr Trp Ile Leu Phe Leu Val Ala Ala Ala Thr Arg Val
1               5                   10                  15

His Ser Ala Gly Ser Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser Ser Gly Gly Gly Ser Gly Gly Gly Gly
    130                 135                 140

Ser Gly Gly Gly Gly Ser Gly Gly Gly Gly Ser Gly Gly Gly Ser Ile
145                 150                 155                 160

Thr Cys Pro Pro Pro Met Ser Val Glu His Ala Asp Ile Trp Val Lys
                165                 170                 175

Ser Tyr Ser Leu Tyr Ser Arg Glu Arg Tyr Ile Cys Asn Ser Gly Phe
            180                 185                 190
```

```
Lys Arg Lys Ala Gly Thr Ser Ser Leu Thr Glu Cys Val Leu Asn Lys
        195                 200                 205

Ala Thr Asn Val Ala His Trp Thr Thr Pro Ser Leu Lys Cys Ile Arg
    210                 215                 220

Asp Gly Gly Gly Gly Ser Gly Gly Gly Gly Ser Arg Ser Asn Leu Gly
225                 230                 235                 240

Trp Leu Cys Leu Leu Leu Leu Pro Ile Pro Leu Ile Val Trp Val Lys
                245                 250                 255

Arg Lys Glu Val Gln Lys Thr
            260


<210> SEQ ID NO 44
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Trp Thr Trp Ile Leu Phe Leu Val Ala Ala Ala Thr Arg Val
1               5                   10                  15

His Ser Ala Gly Ser Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser Ser Gly Gly Gly Ser Gly Gly Gly Gly
    130                 135                 140

Ser Gly Gly Gly Gly Ser Gly Gly Gly Gly Ser Gly Gly Gly Ser Ile
145                 150                 155                 160

Thr Cys Pro Pro Pro Met Ser Val Glu His Ala Asp Ile Trp Val Lys
                165                 170                 175

Ser Tyr Ser Leu Tyr Ser Arg Glu Arg Tyr Ile Cys Asn Ser Gly Phe
            180                 185                 190

Lys Arg Lys Ala Gly Thr Ser Ser Leu Thr Glu Cys Val Leu Asn Lys
        195                 200                 205

Ala Thr Asn Val Ala His Trp Thr Thr Pro Ser Leu Lys Cys Ile Arg
    210                 215                 220

Asp Gly Gly Gly Gly Ser Gly Gly Gly Gly Ser Pro Ile Leu Leu Thr
225                 230                 235                 240

Cys Pro Thr Ile Ser Ile Leu Ser Phe Phe Ser Val Ala Leu Leu Val
                245                 250                 255

Ile Leu Ala Cys Val Leu Trp
            260
```

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gly Ser Thr Ser Gly Ser Gly Lys Pro Gly Ser Gly Glu Gly Ser Thr
1 5 10 15

Lys Gly

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
ggctccacct ctggatccgg caagcccgga tctggcgagg gatccaccaa gggc 54

<210> SEQ ID NO 47
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
gggagcacta gcggctctgg caaacctgga tctggcgagg gatctaccaa gggc 54

<210> SEQ ID NO 48
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
ggctccacca gcggaagcgg caagccaggc tcaggcgaag gatctacaaa aggc 54

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
gggagcacaa gcggctctgg caaacctgga tccggcgagg gatctaccaa gggc 54

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Ile Glu Val Met Tyr Pro Pro Pro Tyr Leu Asp Asn Glu Lys Ser Asn

```
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 51
<211> LENGTH: 117
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
attgaagtta tgtatcctcc tccttaccta gacaatgaga agagcaatgg aaccattatc     60

catgtgaaag ggaaacacct ttgtccaagt cccctatttc ccggaccttc taagccc       117
```

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30
```

<210> SEQ ID NO 53
<211> LENGTH: 90
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 53

```
ctagacaatg agaagagcaa tggaaccatt atccatgtga aagggaaaca cctttgtcca     60

agtcccctat ttcccggacc ttctaagccc                                      90
```

<210> SEQ ID NO 54
<211> LENGTH: 55
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55
```

<210> SEQ ID NO 55
<211> LENGTH: 165
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55
ttcgtgcctg tgttcctgcc tgctaagccc accaccactc ctgctccaag acctcctacc 60
cccgctccta caatcgccag ccaacctctg agcctgagac cggaggcatg cagacctgcg 120
gcagggggag cagttcacac aagaggcttg gacttcgctt gcgac 165

<210> SEQ ID NO 56
<211> LENGTH: 27
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 57
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
ttttgggtgc tggtggtggt tgggggagtc ctggcttgct atagcttgct agtaacagtg 60
gcctttatta ttttctgggt g 81

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Ile Tyr Ile Trp Ala Pro Leu Ala Gly Thr Cys Gly Val Leu Leu Leu
1 5 10 15

Ser Leu Val Ile Thr Leu Tyr Cys Asn His Arg Asn
20 25

<210> SEQ ID NO 59
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
atctacatct gggcccctct ggccggcaca tgcggagttc ttcttcttag cctggtgatc 60
accctgtact gcaaccacag aaac 84

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Val Lys Phe Ser Arg Ser Ala Asp Ala Pro Ala Tyr Gln Gln Gly Gln
1 5 10 15

Asn Gln Leu Tyr Asn Glu Leu Asn Leu Gly Arg Arg Glu Glu Tyr Asp
20 25 30

Val Leu Asp Lys Arg Arg Gly Arg Asp Pro Glu Met Gly Gly Lys Pro
35 40 45

Arg Arg Lys Asn Pro Gln Glu Gly Leu Tyr Asn Glu Leu Gln Lys Asp
50 55 60

Lys Met Ala Glu Ala Tyr Ser Glu Ile Gly Met Lys Gly Glu Arg Arg
65 70 75 80

Arg Gly Lys Gly His Asp Gly Leu Tyr Gln Gly Leu Ser Thr Ala Thr
85 90 95

Lys Asp Thr Tyr Asp Ala Leu His Met Gln Ala Leu Pro Pro Arg
100 105 110

<210> SEQ ID NO 61
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61
agagtgaagt tcagcaggag cgcagacgcc cccgcgtacc agcagggcca gaaccagctc 60
tataacgagc tcaatctagg acgaagagag gagtacgatg ttttggacaa gaggcgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 62
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 63
<211> LENGTH: 123

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 64
<211> LENGTH: 47
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Arg Phe Ser Val Val Lys Arg Gly Arg Lys Lys Leu Leu Tyr Ile Phe
1 5 10 15

Lys Gln Pro Phe Met Arg Pro Val Gln Thr Thr Gln Glu Glu Asp Gly
20 25 30

Cys Ser Cys Arg Phe Pro Glu Glu Glu Glu Gly Gly Cys Glu Leu
35 40 45

<210> SEQ ID NO 65
<211> LENGTH: 141
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
agattcagcg ttgtgaagag aggccggaag aagctgctgt acatcttcaa gcagcccttc 60
atgagacctg tgcagaccac acaggaggaa gacggctgca gctgtagatt ccccgaggaa 120
gaggagggcg gctgtgagct g 141

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Met Leu Leu Leu Val Thr Ser Leu Leu Leu Cys Glu Leu Pro His Pro
1 5 10 15

Ala Phe Leu Leu Ile Pro
20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

```
Met Glu Trp Thr Trp Val Phe Leu Phe Leu Leu Ser Val Thr Ala Gly
1               5                   10                  15

Val His Ser
```

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 69
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

```
Gly Val Ser Leu Pro Asp Tyr Gly
1               5
```

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Asp Tyr Gly Val Ser
1 5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Gly Val Ser Leu Pro Asp Tyr
1 5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Ile Trp Gly Ser Glu Thr Thr
1 5

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Val Ile Trp Gly Ser Glu Thr Thr Tyr Tyr Asn Ser Ala Leu Lys Ser
1 5 10 15

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Trp Gly Ser Glu Thr
1 5

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Ala Lys His Tyr Tyr Tyr Gly Gly Ser Tyr Ala Met Asp Tyr
1 5 10

<210> SEQ ID NO 77
<211> LENGTH: 12

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

His Tyr Tyr Tyr Gly Gly Ser Tyr Ala Met Asp Tyr
1 5 10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

His Tyr Tyr Tyr Gly Gly Ser Tyr Ala Met Asp Tyr
1 5 10

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 79

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr
100 105

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Arg Ala Ser Gln Asp Ile Ser Lys Tyr Leu Asn
1 5 10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Arg Ala Ser Gln Asp Ile Ser Lys Tyr Leu Asn
1 5 10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Arg Ala Ser Gln Asp Ile Ser Lys Tyr Leu Asn
1 5 10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

His Thr Ser Arg Leu His Ser
1 5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

His Thr Ser Arg Leu His Ser
1 5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

His Thr Ser Arg Leu His Ser
1 5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Gln Gln Gly Asn Thr Leu Pro Tyr Thr
1 5

<210> SEQ ID NO 87
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Gln Gln Gly Asn Thr Leu Pro Tyr Thr
1 5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Gln Gln Gly Asn Thr Leu Pro Tyr Thr
1 5

<210> SEQ ID NO 89
<211> LENGTH: 245
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 89

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser 225 230 235 240

Val Thr Val Ser Ser
245

<210> SEQ ID NO 90
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Ala Ala Ala Ile Glu Val Met Tyr Pro Pro Pro
245 250 255

Tyr Leu Asp Asn Glu Lys Ser Asn Gly Thr Ile Ile His Val Lys Gly
260 265 270

Lys His Leu Cys Pro Ser Pro Leu Phe Pro Gly Pro Ser Lys Pro Phe
275 280 285

Trp Val Leu Val Val Val Gly Gly Val Leu Ala Cys Tyr Ser Leu Leu
290 295 300

Val Thr Val Ala Phe Ile Ile Phe Trp Val Arg Ser Lys Arg Ser Arg
305 310 315 320

Leu Leu His Ser Asp Tyr Met Asn Met Thr Pro Arg Arg Pro Gly Pro
325 330 335

```
Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445

Ser Thr Ala Thr Lys Asp Thr Tyr Asp Ala Leu His Met Gln Ala Leu
    450                 455                 460

Pro Pro Arg
465


<210> SEQ ID NO 91
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

gacattcaga tgacccagac caccagcagc ctgagcgcca gcttaggaga tagagttacc     60

atcagctgca gagccagcca ggacatcagc aaatacctga actggtatca gcagaagccc    120

gacggcactg tgaaactgct tatttaccac acctccagac tgcacagcgg cgttcccagc    180

agattctctg gcagcggatc tggaaccgac tacagcctca ccatctccaa cctggagcag    240

gaggacatcg ccacctactt ctgccagcag ggcaacacac tgccctacac cttcggagga    300

ggaaccaagc tggagatcac cggctccacc tctggatccg gcaagcccgg atctggcgag    360

ggatccacca agggcgaggt taagctgcag gagagcggcc ctggcctggt ggctcctagc    420

caatctttat ctgtgacctg cactgtgtcc ggcgttagcc tgcccgatta tggcgtttcc    480

tggatcagac agccccccag aaagggcctg gaatggctgg gcgttatctg gggcagcgag    540

accacatact acaacagcgc cctgaagagc agacttacga ttatcaagga caacagcaag    600

agccaggttt tcctgaagat gaacagcctg cagaccgacg acaccgccat ctactactgc    660

gctaagcact actactacgg cggcagctac gccatggact actggggcca gggaacaagc    720

gttaccgtta gcagcgctgc tgcaattgaa gttatgtatc ctcctcctta cctggacaac    780

gagaagagca acggcaccat catccacgtt aagggcaagc acctgtgccc cagccctctg    840

ttccctggac cttctaagcc tttctgggtt ctggtggtgg tcggcggcgt tttagcctgt    900

tacagccttc tggtgactgt ggccttcatc atcttttggg ttagaagcaa gagaagcaga    960

ctgctccaca gcgactacat gaacatgacc cccagacggc ctggccccac cagaaagcat   1020

taccagccct acgctcctcc cagagacttc gccgcctaca ggagcagagt taaattcagc   1080

agatccgccg atgcccccgc ttaccaacag ggacaaaacc agctgtacaa tgagctcaac   1140

ctggggagaa gagaagaata cgacgttctg gataagagaa ggggcagaga tcccgaaatg   1200

gggggcaagc ccagacgcaa gaaccctcag gaggggcttt acaacgaact gcagaaggat   1260
```

aagatggctg aggcttactc ggagattggg atgaaggggg agagaaggcg gggcaaggga 1320
cacgatggct tataccaggg gctgagcacc gccaccaagg acacatacga cgctcttcat 1380
atgcaggctc tgcccccaag a 1401

<210> SEQ ID NO 92
<211> LENGTH: 761
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 92

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Ser Thr Ser Gly
100 105 110

Ser Gly Lys Pro Gly Ser Gly Glu Gly Ser Thr Lys Gly Glu Val Lys
115 120 125

Leu Gln Glu Ser Gly Pro Gly Leu Val Ala Pro Ser Gln Ser Leu Ser
130 135 140

Val Thr Cys Thr Val Ser Gly Val Ser Leu Pro Asp Tyr Gly Val Ser
145 150 155 160

Trp Ile Arg Gln Pro Pro Arg Lys Gly Leu Glu Trp Leu Gly Val Ile
165 170 175

Trp Gly Ser Glu Thr Thr Tyr Tyr Asn Ser Ala Leu Lys Ser Arg Leu
180 185 190

Thr Ile Ile Lys Asp Asn Ser Lys Ser Gln Val Phe Leu Lys Met Asn
195 200 205

Ser Leu Gln Thr Asp Asp Thr Ala Ile Tyr Tyr Cys Ala Lys His Tyr
210 215 220

Tyr Tyr Gly Gly Ser Tyr Ala Met Asp Tyr Trp Gly Gln Gly Thr Ser
225 230 235 240

Val Thr Val Ser Ser Ala Ala Ala Ile Glu Val Met Tyr Pro Pro Pro
245 250 255

Tyr Leu Asp Asn Glu Lys Ser Asn Gly Thr Ile Ile His Val Lys Gly
260 265 270

Lys His Leu Cys Pro Ser Pro Leu Phe Pro Gly Pro Ser Lys Pro Phe
275 280 285

Trp Val Leu Val Val Val Gly Gly Val Leu Ala Cys Tyr Ser Leu Leu
290 295 300

Val Thr Val Ala Phe Ile Ile Phe Trp Val Arg Ser Lys Arg Ser Arg
305 310 315 320

Leu Leu His Ser Asp Tyr Met Asn Met Thr Pro Arg Arg Pro Gly Pro

```
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445

Ser Thr Ala Thr Lys Asp Thr Tyr Asp Ala Leu His Met Gln Ala Leu
    450                 455                 460

Pro Pro Arg Gly Ser Gly Glu Gly Arg Gly Ser Leu Leu Thr Cys Gly
465                 470                 475                 480

Asp Val Glu Glu Asn Pro Gly Pro Met Asp Trp Thr Trp Ile Leu Phe
                485                 490                 495

Leu Val Ala Ala Ala Thr Arg Val His Ser Glu Gln Lys Leu Ile Ser
            500                 505                 510

Glu Glu Asp Leu Ala Gly Ser Asn Trp Val Asn Val Ile Ser Asp Leu
        515                 520                 525

Lys Lys Ile Glu Asp Leu Ile Gln Ser Met His Ile Asp Ala Thr Leu
    530                 535                 540

Tyr Thr Glu Ser Asp Val His Pro Ser Cys Lys Val Thr Ala Met Lys
545                 550                 555                 560

Cys Phe Leu Leu Glu Leu Gln Val Ile Ser Leu Glu Ser Gly Asp Ala
                565                 570                 575

Ser Ile His Asp Thr Val Glu Asn Leu Ile Ile Leu Ala Asn Asn Ser
            580                 585                 590

Leu Ser Ser Asn Gly Asn Val Thr Glu Ser Gly Cys Lys Glu Cys Glu
        595                 600                 605

Glu Leu Glu Glu Lys Asn Ile Lys Glu Phe Leu Gln Ser Phe Val His
    610                 615                 620

Ile Val Gln Met Phe Ile Asn Thr Ser Ser Gly Gly Gly Ser Gly Gly
625                 630                 635                 640

Gly Gly Ser Gly Gly Gly Gly Ser Gly Gly Gly Gly Ser Gly Gly Gly
                645                 650                 655

Ser Ile Thr Cys Pro Pro Pro Met Ser Val Glu His Ala Asp Ile Trp
            660                 665                 670

Val Lys Ser Tyr Ser Leu Tyr Ser Arg Glu Arg Tyr Ile Cys Asn Ser
        675                 680                 685

Gly Phe Lys Arg Lys Ala Gly Thr Ser Ser Leu Thr Glu Cys Val Leu
    690                 695                 700

Asn Lys Ala Thr Asn Val Ala His Trp Thr Thr Pro Ser Leu Lys Cys
705                 710                 715                 720

Ile Arg Asp Gly Gly Gly Gly Ser Gly Gly Gly Ser Arg Ser Asn
                725                 730                 735

Leu Gly Trp Leu Cys Leu Leu Leu Leu Pro Ile Pro Leu Ile Val Trp
            740                 745                 750
```

Val Lys Arg Lys Glu Val Gln Lys Thr
        755                 760

<210> SEQ ID NO 93
<211> LENGTH: 2286
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
gacatccaga tgacacagac tacatcctcc ctgtctgcct ctctgggaga cagagtcacc 60
atcagttgca gggcaagtca ggacattagt aaatatttaa attggtatca gcagaaacca 120
gatggaactg ttaaactcct gatctaccat acatcaagat tacactcagg agtcccatca 180
aggttcagtg gcagtgggtc tggaacagat tattctctca ccattagcaa cctggagcaa 240
gaagatattg ccacttactt ttgccaacag ggtaatacgc ttccgtacac gttcggaggg 300
gggactaagt tggaaataac aggctccacc tctggatccg gcaagcccgg atctggcgag 360
ggatccacca agggcgaggt gaaactgcag gagtcaggac ctggcctggt ggcgccctca 420
cagagcctgt ccgtcacatg cactgtctca ggggtctcat tacccgacta tggtgtaagc 480
tggattcgcc agcctccacg aaagggtctg gagtggctgg gagtaatatg gggtagtgaa 540
accacatact ataattcagc tctcaaatcc agactgacca tcatcaagga caactccaag 600
agccaagttt tcttaaaaat gaacagtctg caaactgatg acacagccat ttactactgt 660
gccaaacatt attactacgg tggtagctat gctatggact actggggtca aggaacctca 720
gtcacagtct cctcagcggc cgcaattgaa gttatgtatc ctcctcctta cctagacaat 780
gagaagagca atggaaccat tatccatgtg aaagggaaac acctttgtcc aagtccccta 840
tttcccggac cttctaagcc cttttgggtg ctggtggtgg ttgggggagt cctggcttgc 900
tatagcttgc tagtaacagt ggcctttatt attttctggg tgaggagtaa gaggagcagg 960
ctcctgcaca gtgactacat gaacatgact ccccgccgcc ccgggcccac ccgcaagcat 1020
taccagccct atgccccacc acgcgacttc gcagcctatc gctccagagt gaagttcagc 1080
aggagcgcag acgcccccgc gtaccagcag ggccagaacc agctctataa cgagctcaat 1140
ctaggacgaa gagaggagta cgatgttttg gacaagaggc gtggccggga ccctgagatg 1200
gggggaaagc cgagaaggaa gaaccctcag gaaggcctgt acaatgaact gcagaaagat 1260
aagatggcgg aggcctacag tgagattggg atgaaaggcg agcgccggag gggcaagggg 1320
cacgatggcc tttaccaggg tctcagtaca gccaccaagg acacctacga cgcccttcac 1380
atgcaggccc tgccccctcg cggctctggc gaaggcagag gctctctgct gacctgcggc 1440
gacgtggaag agaacccagg ccccatggac tggacatgga ttctgtttct tgtggctgcc 1500
gccacaagag tgcacagcga gcagaagctg atcagcgagg aagacctcgc tggaagcaat 1560
tgggtgaacg tgatctccga cctcaaaaag atcgaggatc tgatccagtc catgcacatc 1620
gatgccacac tctacaccga gtccgatgtg caccctagct gcaaagttac agcaatgaaa 1680
tgctttctgc tggagttgca agtaatctcc ctggagtccg gagatgcttc catccacgac 1740
acagtggaga atttaatcat tctggctaac aattccctct cgtctaatgg caatgtcact 1800
gagagcggct gtaaagagtg tgaagagctg gaggagaaaa acatcaaaga gtttctgcag 1860
agcttcgtcc acatcgtcca aatgttcatc aacacctcgt ccgggggcgg ctccgggggga 1920

```
ggaggatcgg ggggaggagg aagcggaggt ggaggaagcg gtggagggtc cattacatgc   1980

cctcccccca tgtccgtgga acatgccgac atatgggtaa agtcctactc tctgtactcg   2040

cgggaacgtt atatctgcaa cagcggcttt aagagaaagg ccggaacatc ttctctgacc   2100

gaatgtgtgc tgaacaaggc cacaaatgtg gctcactgga ccacgcctag cctcaagtgt   2160

attagggacg gcggcggagg ttccggtggc gggggctcta gatcgaatct gggctggctg   2220

tgtctgctgc tgctccccat ccctctgatt gtgtgggtta agcgaaaaga ggtccagaaa   2280

acctaa                                                              2286


<210> SEQ ID NO 94
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Asp Trp Thr Trp Ile Leu Phe Leu Val Ala Ala Ala Thr Arg Val
1               5                   10                  15

His Ser Glu Gln Lys Leu Ile Ser Glu Glu Asp Leu Ala Gly Ser Asn
            20                  25                  30

Trp Val Asn Val Ile Ser Asp Leu Lys Lys Ile Glu Asp Leu Ile Gln
        35                  40                  45

Ser Met His Ile Asp Ala Thr Leu Tyr Thr Glu Ser Asp Val His Pro
    50                  55                  60

Ser Cys Lys Val Thr Ala Met Lys Cys Phe Leu Leu Glu Leu Gln Val
65                  70                  75                  80

Ile Ser Leu Glu Ser Gly Asp Ala Ser Ile His Asp Thr Val Glu Asn
                85                  90                  95

Leu Ile Ile Leu Ala Asn Asn Ser Leu Ser Ser Asn Gly Asn Val Thr
            100                 105                 110

Glu Ser Gly Cys Lys Glu Cys Glu Glu Leu Glu Glu Lys Asn Ile Lys
        115                 120                 125

Glu Phe Leu Gln Ser Phe Val His Ile Val Gln Met Phe Ile Asn Thr
    130                 135                 140

Ser Ser Gly Gly Gly Ser Gly Gly Gly Gly Ser Gly Gly Gly Gly Ser
145                 150                 155                 160

Gly Gly Gly Gly Ser Gly Gly Gly Ser Ile Thr Cys Pro Pro Pro Met
                165                 170                 175

Ser Val Glu His Ala Asp Ile Trp Val Lys Ser Tyr Ser Leu Tyr Ser
            180                 185                 190

Arg Glu Arg Tyr Ile Cys Asn Ser Gly Phe Lys Arg Lys Ala Gly Thr
        195                 200                 205

Ser Ser Leu Thr Glu Cys Val Leu Asn Lys Ala Thr Asn Val Ala His
    210                 215                 220

Trp Thr Thr Pro Ser Leu Lys Cys Ile Arg Asp Pro Ala Leu Val His
225                 230                 235                 240

Gln Arg Pro Ala Pro Pro Ser Thr Val Thr Thr Ala Gly Val Thr Pro
                245                 250                 255

Gln Pro Glu Ser Leu Ser Pro Ser Gly Lys Glu Pro Ala Ala Ser Ser
            260                 265                 270

Pro Ser Ser Asn Asn Thr Ala Ala Thr Thr Ala Ala Ile Val Pro Gly
        275                 280                 285
```

```
Ser Gln Leu Met Pro Ser Lys Ser Pro Ser Thr Gly Thr Thr Glu Ile
    290                 295                 300

Ser Ser His Glu Ser Ser His Gly Thr Pro Ser Gln Thr Thr Ala Lys
305                 310                 315                 320

Asn Trp Glu Leu Thr Ala Ser Ala Ser His Gln Pro Pro Gly Gly Gly
                325                 330                 335

Gly Gly Ser Gly Gly Gly Gly Ser Arg Ser Asn Leu Gly Trp Leu Cys
            340                 345                 350

Leu Leu Leu Leu Pro Ile Pro Leu Ile Val Trp Val Lys Arg Lys Glu
        355                 360                 365

Val Gln Lys Thr
    370


<210> SEQ ID NO 95
<211> LENGTH: 165
<212> TYPE: PRT
<213> ORGANISM: Homo sapiens

<400> SEQUENCE: 95

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly
                165


<210> SEQ ID NO 96
<211> LENGTH: 783
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

atggactgga catggattct gtttctggtg gccgccgcca caagagtgca cagcaattgg      60

gtgaacgtga tctccgacct caagaagatc gaggatctga tccagtccat gcacatcgat     120

gccacactct acaccgagtc cgatgtgcac cctagctgca aagttacagc catgaaatgc     180

tttctgctgg agctgcaagt gatctctctg gagtccggag atgcttccat ccacgacaca     240

gtggagaatc tgatcattct ggctaacaac tccctctcca gcaacggcaa tgtcacagag     300
```

tccggctgca aagagtgtga agagctggag gagaaaaaca tcaaagagtt tctgcagagc 360
ttcgtccaca tcgtccagat gttcatcaac acctcctccg gcggcggcag cggcggcggc 420
ggatccggcg gaggaggcag cggaggagga ggaagcggag gaggctccat tacatgccct 480
ccccccatgt ccgtggaaca tgccgacatc tgggtgaagt cctactctct gtactcgcgt 540
gaacgttata tctgcaacag cggctttaag aggaaggccg gaacctcctc tctgaccgaa 600
tgtgtgctga acaaggccac caatgtggct cactggacca cacctagcct caagtgtatt 660
agggacggcg gcggaggatc cggaggaggc ggatctagaa gcaatctggg ctggctgtgt 720
ctgctgctgc tccccatccc tctgattgtg tgggtcaaga ggaaggaggt ccagaaaacc 780
taa 783

<210> SEQ ID NO 97
<211> LENGTH: 783
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
atggactgga catggattct gtttctggtg gccgccgcca caagagtgca ctccaactgg 60
gtcaacgtga tctccgatct gaagaagatc gaagatctga tccagtccat gcacatcgat 120
gccacactgt acaccgagag cgacgtgcac cccagctgca aagttacagc catgaagtgc 180
tttctgctcg aactgcaagt gatttctctg gagagcggag atgccagcat ccacgacacc 240
gtggagaatc tgatcattct ggccaacaac tctctgagca gcaacggcaa tgtgacagag 300
tccggctgta aggagtgcga ggagctggag gagaaaaaca tcaaagagtt tctgcagagc 360
ttcgtccaca ttgtccaaat gttcatcaac accagcagcg gcggcggctc cggcggcgga 420
ggctccggcg gaggcggatc cggcggcggc ggatccggcg gaggatccat tacatgcccc 480
cctcccatgt ccgtggaaca cgccgacatc tgggtgaaga gctactctct gtacagcaga 540
gagcgttaca tctgcaacag cggctttaag aggaaagccg gcaccagcag cctcacagag 600
tgcgtgctca acaaggccac caacgtcgcc cattggacca ccccctctct gaagtgtatt 660
agggacggcg gcggaggaag cggaggagga ggaagcccta ttctgctgac atgccccacc 720
atctccatcc tgtctttttt ttctgttgct ctgctggtga ttctggcttg cgtgctgtgg 780
tga 783

<210> SEQ ID NO 98
<211> LENGTH: 2313
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 98
atgcttctcc tggtgacaag ccttctgctc tgtgagttac cacacccagc attcctcctg 60
atcccagaca tccagatgac acagactaca tcctccctgt ctgcctctct gggagacaga 120
gtcaccatca gttgcagggc aagtcaggac attagtaaat atttaaattg gtatcagcag 180
aaaccagatg gaactgttaa actcctgatc taccatacat caagattaca ctcaggagtc 240
ccatcaaggt tcagtggcag tgggtctgga acagattatt ctctcaccat tagcaacctg 300

```
gagcaagaag atattgccac ttacttttgc caacagggta atacgcttcc gtacacgttc    360

ggagggggga ctaagttgga aataacaggc tccacctctg gatccggcaa gcccggatct    420

ggcgagggat ccaccaaggg cgaggtgaaa ctgcaggagt caggacctgg cctggtggcg    480

ccctcacaga gcctgtccgt cacatgcact gtctcagggg tctcattacc cgactatggt    540

gtaagctgga ttcgccagcc tccacgaaag ggtctggagt ggctgggagt aatatggggt    600

agtgaaacca catactataa ttcagctctc aaatccagac tgaccatcat caaggacaac    660

tccaagagcc aagttttctt aaaaatgaac agtctgcaaa ctgatgacac agccatttac    720

tactgtgcca aacattatta ctacggtggt agctatgcta tggactactg gggtcaagga    780

acctcagtca cagtctcctc agcggccgca attgaagtta tgtatcctcc tccttaccta    840

gacaatgaga agagcaatgg aaccattatc catgtgaaag ggaaacacct ttgtccaagt    900

cccctatttc ccggaccttc taagcccttt tgggtgctgg tggtggttgg gggagtcctg    960

gcttgctata gcttgctagt aacagtggcc tttattattt tctgggtgag gagtaagagg   1020

agcaggctcc tgcacagtga ctacatgaac atgactcccc gccgccccgg gcccacccgc   1080

aagcattacc agccctatgc cccaccacgc gacttcgcag cctatcgctc cagagtgaag   1140

ttcagcagga gcgcagacgc ccccgcgtac cagcagggcc agaaccagct ctataacgag   1200

ctcaatctag gacgaagaga ggagtacgat gttttggaca agaggcgtgg ccgggaccct   1260

gagatggggg gaaagccgag aaggaagaac cctcaggaag gcctgtacaa tgaactgcag   1320

aaagataaga tggcggaggc ctacagtgag attgggatga aaggcgagcg ccggaggggc   1380

aaggggcacg atggccttta ccagggtctc agtacagcca ccaaggacac ctacgacgcc   1440

cttcacatgc aggccctgcc ccctcgcggc tctggagagg gcagaggctc tctgctgacc   1500

tgcggcgacg tggaagagaa cccaggcccc atggactgga catggattct gtttctggtg   1560

gccgccgcca caagagtgca cagcaattgg gtgaacgtga tctccgacct caagaagatc   1620

gaggatctga tccagtccat gcacatcgat gccacactct acaccgagtc cgatgtgcac   1680

cctagctgca aagttacagc catgaaatgc tttctgctgg agctgcaagt gatctctctg   1740

gagtccggag atgcttccat ccacgacaca gtggagaatc tgatcattct ggctaacaac   1800

tccctctcca gcaacggcaa tgtcacagag tccggctgca aagagtgtga agagctggag   1860

gagaaaaaca tcaaagagtt tctgcagagc ttcgtccaca tcgtccagat gttcatcaac   1920

acctcctccg gcggcggcag cggcggcggc ggatccggcg gaggaggcag cggaggagga   1980

ggaagcggag gaggctccat tacatgccct ccccccatgt ccgtggaaca tgccgacatc   2040

tgggtgaagt cctactctct gtactcgcgt gaacgttata tctgcaacag cggctttaag   2100

aggaaggccg gaacctcctc tctgaccgaa tgtgtgctga acaaggccac caatgtggct   2160

cactggacca cacctagcct caagtgtatt agggacggcg gcggaggatc cggaggaggc   2220

ggatctagaa gcaatctggg ctggctgtgt ctgctgctgc tccccatccc tctgattgtg   2280

tgggtcaaga ggaaggaggt ccagaaaacc taa                                2313
```

<210> SEQ ID NO 99
<211> LENGTH: 2337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atgcttctcc tggtgacaag ccttctgctc tgtgagttac cacacccagc attcctcctg     60
atcccagaca tccagatgac acagactaca tcctccctgt ctgcctctct gggagacaga    120
gtcaccatca gttgcagggc aagtcaggac attagtaaat atttaaattg gtatcagcag    180
aaaccagatg gaactgttaa actcctgatc taccatacat caagattaca ctcaggagtc    240
ccatcaaggt tcagtggcag tgggtctgga acagattatt ctctcaccat tagcaacctg    300
gagcaagaag atattgccac ttacttttgc caacagggta atacgcttcc gtacacgttc    360
ggaggggga ctaagttgga aataacaggc tccacctctg gatccggcaa gcccggatct    420
ggcgagggat ccaccaaggg cgaggtgaaa ctgcaggagt caggacctgg cctggtggcg    480
ccctcacaga gcctgtccgt cacatgcact gtctcagggg tctcattacc cgactatggt    540
gtaagctgga ttcgccagcc tccacgaaag ggtctggagt ggctgggagt aatatggggt    600
agtgaaacca catactataa ttcagctctc aaatccagac tgaccatcat caaggacaac    660
tccaagagcc aagttttctt aaaaatgaac agtctgcaaa ctgatgacac agccatttac    720
tactgtgcca aacattatta ctacggtggt agctatgcta tggactactg gggtcaagga    780
acctcagtca cagtctcctc agcggccgca attgaagtta tgtatcctcc tccttaccta    840
gacaatgaga agagcaatgg aaccattatc catgtgaaag ggaaacacct ttgtccaagt    900
cccctatttc ccggaccttc taagcccttt tgggtgctgg tggtggttgg gggagtcctg    960
gcttgctata gcttgctagt aacagtggcc tttattattt tctgggtgag gagtaagagg   1020
agcaggctcc tgcacagtga ctacatgaac atgactcccc gccgccccgg gcccacccgc   1080
aagcattacc agccctatgc cccaccacgc gacttcgcag cctatcgctc cagagtgaag   1140
ttcagcagga gcgcagacgc ccccgcgtac cagcagggcc agaaccagct ctataacgag   1200
ctcaatctag gacgaagaga ggagtacgat gttttggaca agaggcgtgg ccgggaccct   1260
gagatggggg gaaagccgag aaggaagaac cctcaggaag gcctgtacaa tgaactgcag   1320
aaagataaga tggcggaggc ctacagtgag attgggatga aaggcgagcg ccggaggggc   1380
aaggggcacg atggccttta ccagggtctc agtacagcca ccaaggacac ctacgacgcc   1440
cttcacatgc aggccctgcc ccctcgcggc tctggagagg gcagaggctc tctgctgacc   1500
tgcggcgacg tggaagagaa cccaggcccc atggactgga catggattct gtttctggtg   1560
gccgccgcca caagagtgca ctccaactgg gtcaacgtga tctccgatct gaagaagatc   1620
gaagatctga tccagtccat gcacatcgat gccacactgt acaccgagag cgacgtgcac   1680
cccagctgca aagttacagc catgaagtgc tttctgctcg aactgcaagt gatttctctg   1740
gagagcggag atgccagcat ccacgacacc gtggagaatc tgatcattct ggccaacaac   1800
tctctgagca gcaacggcaa tgtgacagag tccggctgta aggagtgcga ggagctggag   1860
gagaaaaaca tcaaagagtt tctgcagagc ttcgtccaca ttgtccaaat gttcatcaac   1920
accagcagcg gcggcggctc cggcggcgga ggctccggcg gaggcggatc cggcggcggc   1980
ggatccggcg gaggatccat tacatgcccc cctcccatgt ccgtggaaca cgccgacatc   2040
tgggtgaaga gctactctct gtacagcaga gagcgttaca tctgcaacag cggctttaag   2100
aggaaagccg gcaccagcag cctcacagag tgcgtgctca acaaggccac caacgtcgcc   2160
cattggacca ccccctctct gaagtgtatt agggacggcg gcggaggaag cggaggagga   2220
ggaagcccta ttctgctgac atgccccacc atctccatcc tgtctttttt ttctgttgct   2280
ctgctggtga ttctggcttg cgtgctgtgg aagaagagga tcaagccgat agtttga      2337
```

```
<210> SEQ ID NO 100
<211> LENGTH: 1080
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

atggactgga cctggatact tttcctggtg gccgccgcta ccagagttca ctcaaattgg     60

gtcaatgtaa tttcagactt gaagaagatc gaagatctga tccagtctat gcatatagat    120

gctactctgt acactgagtc cgatgtgcat ccgtcctgta aagtgacagc catgaagtgt    180

ttcctgcttg agctccaagt tatcagtctc gaatccggcg atgcctcaat acatgatact    240

gtagagaacc tcatcattct cgcaaacaat tccctgtcaa gcaatggaaa tgttacggag    300

tcaggttgta aagaatgtga ggaattggaa gaaaagaaca taaaagagtt cttgcagagt    360

ttcgtgcaca tcgtacaaat gttcatcaat acgagtagtg gtggtggttc cggaggagga    420

ggatctggcg gaggcggtag tggtggagga ggatccggag gtgggagtat aacttgtccg    480

ccgcccatga gtgtggaaca tgctgatata tgggtaaagt cttattcact ttatagcaga    540

gaacgctata tttgtaattc tggcttcaag cgaaaagctg gcacgagcag tctcacggag    600

tgcgtcctga acaaggcaac caacgtcgcg cattggacaa ctcctagcct caaatgcata    660

agggaccctg cactggtgca ccaacgccct gcgccaccgt caacggtcac tacagctggc    720

gttacaccgc agccagaatc tttgagtcca tcaggcaagg aacccgcggc gtcttccccg    780

tcttctaaca ataccgccgc aacgacggcg gcaatcgtgc cgggatcaca actcatgcct    840

tccaaaagtc cctcaacggg cacgacagag attagcagcc acgaaagctc ccatggcact    900

ccctcacaaa cgaccgcgaa gaactgggag ctgactgcaa gtgcatctca ccagccaccg    960

ggtggcgggg gtggatcagg tggcggtggc tctcgctcca acctcggttg gctttgcctt   1020

cttttgctgc ccataccgtt gatcgtctgg gttaagcgca aagaagtcca gaaaacttaa   1080


<210> SEQ ID NO 101
<211> LENGTH: 2622
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

atgcttctcc tggtgacaag ccttctgctc tgtgagttac cacacccagc attcctcctg     60

atcccagaca tccagatgac acagactaca tcctccctgt ctgcctctct gggagacaga    120

gtcaccatca gttgcagggc aagtcaggac attagtaaat atttaaattg gtatcagcag    180

aaaccagatg gaactgttaa actcctgatc taccatacat caagattaca ctcaggagtc    240

ccatcaaggt tcagtggcag tgggtctgga acagattatt ctctcaccat tagcaacctg    300

gagcaagaag atattgccac ttacttttgc caacagggta atacgcttcc gtacacgttc    360

ggagggggga ctaagttgga aataacaggc tccacctctg gatccggcaa gcccggatct    420

ggcgagggat ccaccaaggg cgaggtgaaa ctgcaggagt caggacctgg cctggtggcg    480

ccctcacaga gcctgtccgt cacatgcact gtctcagggg tctcattacc cgactatggt    540

gtaagctgga ttcgccagcc tccacgaaag ggtctggagt ggctgggagt aatatggggt    600

agtgaaacca catactataa ttcagctctc aaatccagac tgaccatcat caaggacaac    660
```

```
tccaagagcc aagttttctt aaaaatgaac agtctgcaaa ctgatgacac agccatttac    720
tactgtgcca aacattatta ctacggtggt agctatgcta tggactactg gggtcaagga    780
acctcagtca cagtctcctc agcggccgca attgaagtta tgtatcctcc tccttaccta    840
gacaatgaga agagcaatgg aaccattatc catgtgaaag ggaaacacct ttgtccaagt    900
cccctatttc ccggaccttc taagcccttt tgggtgctgg tggtggttgg gggagtcctg    960
gcttgctata gcttgctagt aacagtggcc tttattattt tctgggtgag gagtaagagg   1020
agcaggctcc tgcacagtga ctacatgaac atgactcccc gccgccccgg gcccacccgc   1080
aagcattacc agccctatgc cccaccacgc gacttcgcag cctatcgctc cagagtgaag   1140
ttcagcagga gcgcagacgc ccccgcgtac cagcagggcc agaaccagct ctataacgag   1200
ctcaatctag gacgaagaga ggagtacgat gttttggaca agaggcgtgg ccgggaccct   1260
gagatggggg gaaagccgag aaggaagaac cctcaggaag gcctgtacaa tgaactgcag   1320
aaagataaga tggcggaggc ctacagtgag attgggatga aaggcgagcg ccggaggggc   1380
aaggggcacg atggccttta ccagggtctc agtacagcca ccaaggacac ctacgacgcc   1440
cttcacatgc aggccctgcc ccctcgcaga gccaagagag gctccggaga gggcagaggc   1500
tctctgctga cctgcggcga cgtggaagag aatccagggc ccatggactg gacctggata   1560
cttttcctgg tggccgccgc taccagagtt cactcaaatt gggtcaatgt aatttcagac   1620
ttgaagaaga tcgaagatct gatccagtct atgcatatag atgctactct gtacactgag   1680
tccgatgtgc atccgtcctg taaagtgaca gccatgaagt gtttcctgct tgagctccaa   1740
gttatcagtc tcgaatccgg cgatgcctca atacatgata ctgtagagaa cctcatcatt   1800
ctcgcaaaca attccctgtc aagcaatgga aatgttacgg agtcaggttg taaagaatgt   1860
gaggaattgg aagaaaagaa cataaaagag ttcttgcaga gtttcgtgca catcgtacaa   1920
atgttcatca atacgagtag tggtggtggt tccggaggag gaggatctgg cggaggcggt   1980
agtggtggag gaggatccgg aggtgggagt ataacttgtc cgccgcccat gagtgtggaa   2040
catgctgata tatgggtaaa gtcttattca ctttatagca gagaacgcta tatttgtaat   2100
tctggcttca agcgaaaagc tggcacgagc agtctcacgg agtgcgtcct gaacaaggca   2160
accaacgtcg cgcattggac aactcctagc ctcaaatgca taagggaccc tgcactggtg   2220
caccaacgcc ctgcgccacc gtcaacggtc actacagctg gcgttacacc gcagccagaa   2280
tctttgagtc catcaggcaa ggaacccgcg gcgtcttccc cgtcttctaa caataccgcc   2340
gcaacgacgg cggcaatcgt gccgggatca caactcatgc cttccaaaag tccctcaacg   2400
ggcacgacag agattagcag ccacgaaagc tcccatggca ctccctcaca aacgaccgcg   2460
aagaactggg agctgactgc aagtgcatct caccagccac cgggtggcgg gggtggatca   2520
ggtggcggtg gctctcgctc caacctcggt tggctttgcc ttcttttgct gcccataccg   2580
ttgatcgtct gggttaagcg caaagaagtc cagaaaactt aa                      2622
```

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

```
Gly Gly Gly Gly Ser Gly Gly Gly Gly Ser Gly Gly Gly Gly Ser
1               5                   10                  15
```

<210> SEQ ID NO 103
<211> LENGTH: 738
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 103
gctggaagca attgggtgaa cgtgatctcc gacctcaaaa agatcgagga tctgatccag 60
tccatgcaca tcgatgccac actctacacc gagtccgatg tgcaccctag ctgcaaagtt 120
acagcaatga aatgctttct gctggagttg caagtaatct ccctggagtc cggagatgct 180
tccatccacg acacagtgga gaatttaatc attctggcta acaattccct ctcgtctaat 240
ggcaatgtca ctgagagcgg ctgtaaagag tgtgaagagc tggaggagaa aaacatcaaa 300
gagtttctgc agagcttcgt ccacatcgtc caaatgttca tcaacacctc gtccgggggc 360
ggctccgggg gaggaggatc gggggggagga ggaagcggag gtggaggaag cggtggaggg 420
tccattacat gccctccccc catgtccgtg gaacatgccg acatatgggt aaagtcctac 480
tctctgtact cgcgggaacg ttatatctgc aacagcggct ttaagagaaa ggccggaaca 540
tcttctctga ccgaatgtgt gctgaacaag gccacaaatg tggctcactg gaccacgcct 600
agcctcaagt gtattaggga cggcggcgga ggttccggtg gcgggggctc tagatcgaat 660
ctgggctggc tgtgtctgct gctgctcccc atccctctga ttgtgtgggt taagcgaaaa 720
gaggtccaga aaacctaa 738

<210> SEQ ID NO 104
<211> LENGTH: 2
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Gly Ser
1

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Gly Gly Gly Ser Gly Gly Gly Ser
1               5

<210> SEQ ID NO 106
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106
agagttaagt tcagcaggag cgccgacgcc cctgcctacc agcaaggaca gaatcaactg 60

```
tacaacgagc tgaacctggg cagacgggag gaatacgatg tgctggacaa gaggagaggc    120

agagaccccg agatgggcgg caaacctaga agaaagaacc cccaggaggg cctgtataac    180

gagctccaga aggacaagat ggccgaggcc tacagcgaga tcggcatgaa gggcgaaaga    240

agaagaggca agggccacga cggcctctac cagggcttaa gcacagctac aaaggacacc    300

tacgacgccc tgcacatgca ggccctgccc cctaga                              336
```

```
<210> SEQ ID NO 107
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Glu Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly His Thr Tyr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Pro His Tyr Asp Asp Trp Ser Gly Phe Ile Ile Trp Phe
            100                 105                 110

Asp Pro Trp Gly Gln Gly Thr Leu Val Thr Val Ser Ser Gly Ser Thr
        115                 120                 125

Ser Gly Ser Gly Lys Pro Gly Ser Gly Glu Gly Ser Thr Lys Gly Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Arg Phe Pro Pro Thr
225                 230                 235                 240

Phe Gly Gln Gly Thr Lys Val Glu Ile Lys Ala Ala Ala Phe Val Pro
                245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
```

```
305                 310                 315                 320

Val Leu Leu Leu Ser Leu Val Ile Thr Leu Tyr Cys Asn His Arg Asn
                325                 330                 335

Arg Phe Ser Val Val Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495


<210> SEQ ID NO 108
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

caggttcagc ttgtgcagag cggagctgaa gttaagaagc ctggcgcctc tgtgaaggtt     60

agctgcaagg ccagcggcta cacattcaag gaatatggca tctcctgggt taggcaggct    120

cccggccaag gcttagaatg gatgggctgg atctccgcct actccggcca cacctactac    180

gcccagaagc ttcagggcag ggttaccatg accaccgaca ccagcacctc taccgcctat    240

atggagctga ggagcctgag atcggacgac acagctgtgt attactgcgc cagaggcccc    300

cactacgacg actggtctgg atttatcatc tggttcgacc cctgggggca gggcaccctg    360

gtcacagttt cttctggctc caccagcgga agcggcaagc caggctcagg cgaaggatct    420

acaaaaggcg acatccaaat gacacagagc cccagcagct tgagcgcctc cgttggcgac    480

agagttacaa tcacctgcag ggcctctcag agcatcagca gctatttgaa ttggtatcaa    540

cagaagccag gaaaggcccc taagctgctc atctacgctg ccagctcgct ccaatctggc    600

gttcctagca gatttagcgg ctccggcagc ggcacagact ttactcttac cattagctcc    660

ctgcagcccg aggacttcgc tacctactat tgccagcaaa gctacagatt ccctcccacc    720

tttggccagg gcacaaaggt tgagatcaag gcagctgctt tcgtgcctgt gttcctgcct    780

gctaagccca ccaccactcc tgctccaaga cctcctaccc ccgctcctac aatcgccagc    840

caacctctga gcctgagacc ggaggcatgc agacctgcgg cagggggagc agttcacaca    900

agaggcttgg acttcgcttg cgacatctac atctgggccc ctctggccgg cacatgcgga    960

gttcttcttc ttagcctggt gatcaccctg tactgcaacc acagaaacag attcagcgtt   1020
```

```
gtgaagagag gccggaagaa gctgctgtac atcttcaagc agcccttcat gagacctgtg   1080

cagaccacac aggaggaaga cggctgcagc tgtagattcc ccgaggaaga ggagggcggc   1140

tgtgagctga gagttaagtt cagcaggagc gccgacgccc ctgcctacca gcaaggacag   1200

aatcaactgt acaacgagct gaacctgggc agacgggagg aatacgatgt gctggacaag   1260

aggagaggca gagaccccga gatgggcggc aaacctagaa gaaagaaccc ccaggagggc   1320

ctgtataacg agctccagaa ggacaagatg gccgaggcct acagcgagat cggcatgaag   1380

ggcgaaagaa gaagaggcaa gggccacgac ggcctctacc agggcttaag cacagctaca   1440

aaggacacct acgacgccct gcacatgcag gccctgcccc ctaga                   1485


<210> SEQ ID NO 109
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(5)
<223> OTHER INFORMATION: This region may encompass 1-5 "Gly" repeating
      units
<220> FEATURE:
<221> NAME/KEY: SITE
<222> LOCATION: (6)..(10)
<223> OTHER INFORMATION: This region may encompass 1-5 "Ser" repeating
      units
<220> FEATURE:
<221> NAME/KEY: SITE
<222> LOCATION: (1)..(50)
<223> OTHER INFORMATION: This sequence may encompass 1-5 "Gly Gly Gly
      Gly Gly Ser Ser Ser Ser Ser" repeating units
<220> FEATURE:
<223> OTHER INFORMATION: See specification as filed for detailed
      description of substitutions and preferred embodiments

<400> SEQUENCE: 109

Gly Gly Gly Gly Gly Ser Ser Ser Ser Ser Gly Gly Gly Gly Gly Ser
1               5                   10                  15

Ser Ser Ser Ser Gly Gly Gly Gly Gly Ser Ser Ser Ser Ser Gly Gly
            20                  25                  30

Gly Gly Gly Ser Ser Ser Ser Ser Gly Gly Gly Gly Gly Ser Ser Ser
        35                  40                  45

Ser Ser
    50
```